US012686717B2

(12) United States Patent
Holmes

(10) Patent No.: US 12,686,717 B2
(45) Date of Patent: Jul. 21, 2026

(54) ANTI-PD-L1 ANTIBODIES

(71) Applicant: CENTESSA PHARMACEUTICALS (UK) LIMITED, Altrincham (GB)

(72) Inventor: Steve Holmes, London (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 1123 days.

(21) Appl. No.: 17/627,517

(22) PCT Filed: Jul. 15, 2020

(86) PCT No.: PCT/EP2020/070065
§ 371 (c)(1),
(2) Date: Jan. 14, 2022

(87) PCT Pub. No.: WO2021/009267
PCT Pub. Date: Jan. 21, 2021

(65) Prior Publication Data
US 2022/0356255 A1     Nov. 10, 2022

(30) Foreign Application Priority Data

Jul. 15, 2019     (GB) ..................................... 1910138

(51) Int. Cl.
| | |
|---|---|
| C07K 16/28 | (2006.01) |
| A61K 39/00 | (2006.01) |
| A61K 39/395 | (2006.01) |
| A61K 45/06 | (2006.01) |
| A61P 35/00 | (2006.01) |
| A61P 43/00 | (2006.01) |

(52) U.S. Cl.
CPC ........ *C07K 16/2827* (2013.01); *A61K 39/395* (2013.01); *A61K 39/3955* (2013.01); *A61K 45/06* (2013.01); *A61P 35/00* (2018.01); *A61P 43/00* (2018.01); *C07K 16/28* (2013.01); *A61K 2039/505* (2013.01); *A61K 2039/507* (2013.01); *C07K 2317/24* (2013.01); *C07K 2317/31* (2013.01); *C07K 2317/34* (2013.01); *C07K 2317/56* (2013.01); *C07K 2317/565* (2013.01); *C07K 2317/76* (2013.01); *C07K 2317/77* (2013.01); *C07K 2317/92* (2013.01); *C07K 2317/94* (2013.01)

(58) Field of Classification Search
CPC ............ C07K 16/2827; C07K 2317/24; C07K 2317/34; C07K 2317/76; C07K 2317/92; C07K 2317/77; C07K 2317/94; C07K 16/28; C07K 2317/56; C07K 2317/565; C07K 2317/31; A61P 35/00; A61P 43/00; A61K 2039/507; A61K 2039/505; A61K 39/395; A61K 39/3955; A61K 45/06; A61K 2300/00
See application file for complete search history.

(56) References Cited

U.S. PATENT DOCUMENTS

2009/0055944 A1     2/2009   Korman et al.

FOREIGN PATENT DOCUMENTS

| | | |
|---|---|---|
| CN | 105777906 A | 7/2016 |
| CN | 108948193 A | 12/2018 |
| EP | 1537878 A1 | 6/2005 |
| JP | 2008544755 A | 12/2008 |
| JP | 2013511959 A | 4/2013 |
| JP | 2015500207 A | 1/2015 |
| JP | 2015535691 A | 12/2015 |
| JP | 2017507650 A | 3/2017 |
| JP | 2019503687 A | 2/2019 |
| JP | 2019516394 A | 6/2019 |
| WO | 2011066389 A1 | 6/2011 |
| WO | 2014055897 A2 | 4/2014 |
| WO | WO-2017118321 A1 | 7/2017 |
| WO | 2017161976 A1 | 9/2017 |

OTHER PUBLICATIONS

Hall et al. A Single Amino Acid Mutation in CDR3 of the 3-14-9 L Chain abolished expression of the IDA 10-defined Idiotope and Antigen Binding. Journal of immunology (Baltimore, Md. : 1950) (1992). 149 (5):1605-12. (Year: 1992).*
Rabia et al. "Understanding and overcoming trade-offs between antibody affinity, specificity, stability and solubility". Biochem Eng J. Sep. 15, 2018;137:365-374. doi: 10.1016/j.bej.2018.06.003. Epub Jun. 5, 2018. (Year: 2018).*
Vajdos et al. "Comprehensive Functional Maps of the Antigen-binding Site of an Anti-ErbB2 Antibody Obtained with Shotgun Scanning Mutagenesis". J Mol Biol. (2002). 320(2):415-428. (Year: 2002).*
Ribas et al. "What does PD-L1 positive or negative mean?" J Exp Med (2016) 213 (13): 2835-2840. (Year: 2016).*
Shen et al. "Efficacy of PD-1 or PD-L1 inhibitors and PD-L1 expression status in cancer: meta-analysis". BMJ 2018;362:k3529 (Year: 2018).*
International Search Report mailed Nov. 18, 2020 for International Patent Application No. PCT/EP2020/070065.
Written Opinion mailed Nov. 18, 2020 for International Patent Application No. PCT/EP2020/070065.
Combined Search and Examination Report under Sections 17 and 18(3) dated Jan. 10, 2020 for United Kingdom Patent Application No. 1910138.5.

(Continued)

*Primary Examiner* — Mark Halvorson
*Assistant Examiner* — Lea S O'Brien
(74) *Attorney, Agent, or Firm* — WILSON SONSINI GOODRICH & ROSATI

(57) ABSTRACT

The present invention relates to antigen binding molecules, particularly antibodies, fragments and variants thereof, that bind to the programmed death-ligand 1 (PD-L1) in a pH-dependant manner, competing with PD-L1 binding to the inhibitory receptor programmed death 1 polypeptide (PD-1) and co-stimulatory molecule CD80, and the use of said antigen binding molecules in treating and/or preventing diseases such as cancer.

13 Claims, 9 Drawing Sheets

Specification includes a Sequence Listing.

(56)        References Cited

OTHER PUBLICATIONS

Examination Report dated Feb. 2, 2023, for corresponding European Patent Application No. 20 742 695.8, 4 pages.
Kunik, V. et al: "Structural Consensus among Antibodies Defines the Antigen Binding Site", PLoS Computational Biology, vol. 8, No. 2, Feb. 23, 2012 (Feb. 23, 2012), p. e1002388.

* cited by examiner

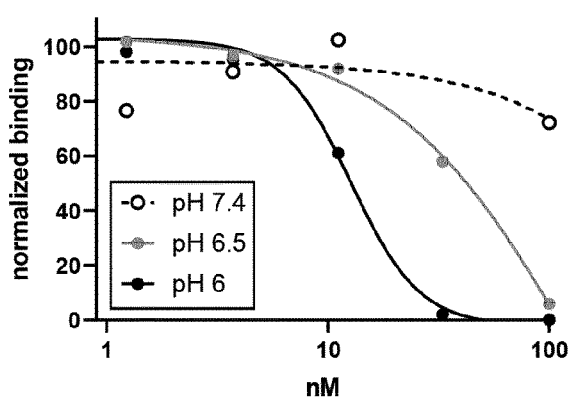
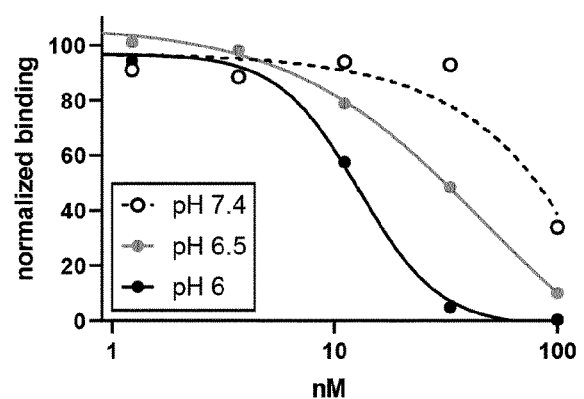
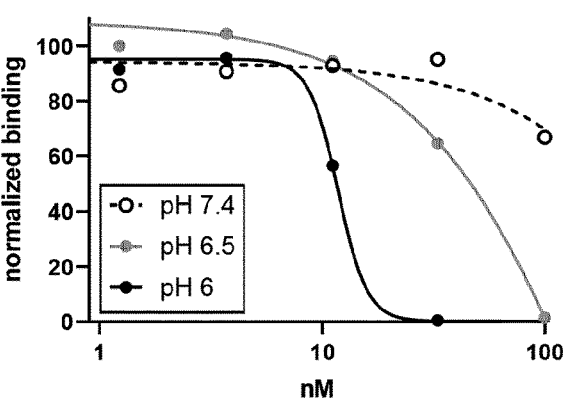
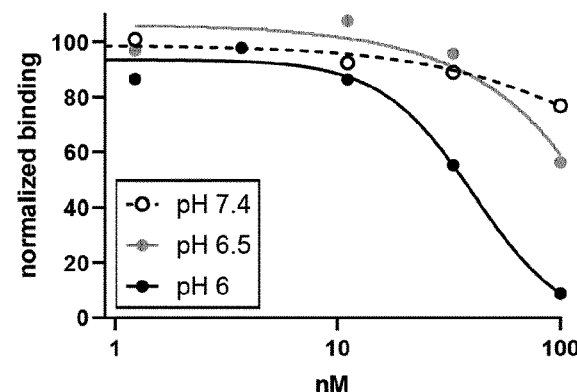
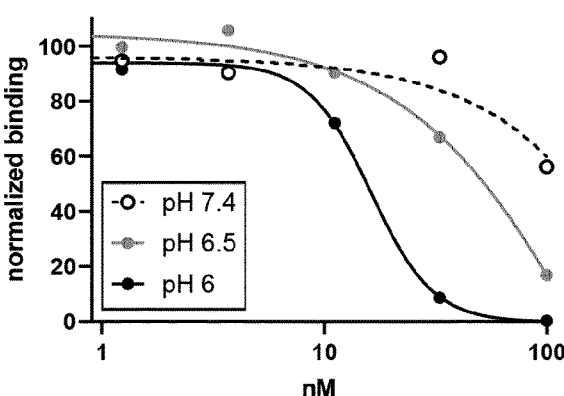
Fig. 5

| Clone nr. | Clone ID | Library ID | Library name | HCDR1 | HCDR1 no. | HCDR2 | HCDR2 no. | HCDR3 |
|---|---|---|---|---|---|---|---|---|
| 47 | FJ1424_P007MP05G06 | 2A09_WT clone | 2A09_WT clone | SYGMY | 1 | VISYDGSNKYYADSVKG | 1 | GALTHWGVVIGDGMDV |
| 351 | FJ1424_P007MP08G08 | FL0675 | AFF2A09_LCDR1 sub lib | SYGMY | 1 | VISYDGSNKYYADSVKG | 1 | GALTHWGVVIGDGMDV |
| 332 | FJ1424_P007MP08D06 | FL0675 | AFF2A09_LCDR1 sub lib | SYGMY | 1 | VISYDGSNKYYADSVKG | 1 | GALTHWGVVIGDGMDV |
| 313 | FJ1424_P007MP08A04 | FL0675 | AFF2A09_LCDR1 sub lib | SYGMY | 1 | VISYDGSNKYYADSVKG | 1 | GALTHWGVVIGDGMDV |
| 330 | FJ1424_P007MP08B06 | FL0675 | AFF2A09_LCDR1 sub lib | SYGMY | 1 | VISYDGSNKYYADSVKG | 1 | GALTHWGVVIGDGMDV |
| 316 | FJ1424_P007MP08D04 | FL0675 | AFF2A09_LCDR1 sub lib | SYGMY | 1 | VISYDGSNKYYADSVKG | 1 | GALTHWGVVIGDGMDV |

| Clone nr. | VH sequence |
|---|---|
| 47 | QVQLVQSGGGVVQPGRSLRLSCAASGFTFSSYGMYWVRQAPGKGLEWVAVISYDGSNKYYADSVKGRFTISRDNSKNTLNLQMNSLRAEDTAVYYCAKGALTHWGVVIGDGMDVWGQGTTVTVSS |
| 351 | QVQLVQSGGGVVQPGRSLRLSCAASGFTFSSYGMYWVRQAPGKGLEWVAVISYDGSNKYYADSVKGRFTISRDNSKNTLNLQMNSLRAEDTAVYYCAKGALTHWGVVIGDGMDVWGQGTTVTVSS |
| 332 | QVQLVQSGGGVVQPGRSLRLSCAASGFTFSSYGMYWVRQAPGKGLEWVAVISYDGSNKYYADSVKGRFTISRDNSKNTLNLQMNSLRAEDTAVYYCAKGALTHWGVVIGDGMDVWGQGTTVTVSS |
| 313 | QVQLVQSGGGVVQPGRSLRLSCAASGFTFSSYGMYWVRQAPGKGLEWVAVISYDGSNKYYADSVKGRFTISRDNSKNTLNLQMNSLRAEDTAVYYCAKGALTHWGVVIGDGMDVWGQGTTVTVSS |
| 330 | QVQLVQSGGGVVQPGRSLRLSCAASGFTFSSYGMYWVRQAPGKGLEWVAVISYDGSNKYYADSVKGRFTISRDNSKNTLNLQMNSLRAEDTAVYYCAKGALTHWGVVIGDGMDVWGQGTTVTVSS |
| 316 | QVQLVQSGGGVVQPGRSLRLSCAASGFTFSSYGMYWVRQAPGKGLEWVAVISYDGSNKYYADSVKGRFTISRDNSKNTLNLQMNSLRAEDTAVYYCAKGALTHWGVVIGDGMDVWGQGTTVTVSS |

Fig. 7

| Clone nr. | Clone ID | Library ID | Library name | LCDR1 | LCDR2 | LCDR3 |
|---|---|---|---|---|---|---|
| 47 | FJ1424_P007MP05G06 | 2A09_WT clone | 2A09_WT clone | TRSSGSIASNYVQ | EDDQRPS | QSFDSTNPWV |
| 351 | FJ1424_P007MP08G08 | FL0675 | AFF2A09_LCDR1 sub lib | ISNDVPASGHYHR | EDDQRPS | QSFDSTNPWV |
| 332 | FJ1424_P007MP08D06 | FL0675 | AFF2A09_LCDR1 sub lib | VLSPRTHAGHYYR | EDDQRPS | QSFDSTNPWV |
| 313 | FJ1424_P007MP08A04 | FL0675 | AFF2A09_LCDR1 sub lib | MRTGTGNKGHYTR | EDDQRPS | QSFDSTNPWV |
| 330 | FJ1424_P007MP08B06 | FL0675 | AFF2A09_LCDR1 sub lib | RETELSRRLHYVR | EDDQRPS | QSFDSTNPWV |
| 316 | FJ1424_P007MP08D04 | FL0675 | AFF2A09_LCDR1 sub lib | RGTGSSFHHKYVR | EDDQRPS | QSFDSTNPWV |

| Clone nr. | VL sequence |
|---|---|
| 47 | NFMLTQPHSVSESPGKTVTISCTRSSGSIASNVVQWYQQRPGSSPTTVIYEDDQRPSGVPDRFSGSIDSSSNSASLTISGLKTEDEADYYCQSFDSTNPWVFGGGTKLTVL |
| 351 | NFMLTQPHSVSESPGKTVTISCISNDVPASGHYHRWYQQRPGSSPTTVIYEDDQRPSGVPDRFSGSIDSSSNSASLTISGLKTEDEADYYCQSFDSTNPWVFGGGTKLTVL |
| 332 | NFMLTQPHSVSESPGKTVTISCVLSPRTHAGHYYRWYQQRPGSSPTTVIYEDDQRPSGVPDRFSGSIDSSSNSASLTISGLKTEDEADYYCQSFDSTNPWVFGGGTKLTVL |
| 313 | NFMLTQPHSVSESPGKTVTISCMRTGTGNKGHYTRWYQQRPGSSPTTVIYEDDQRPSGVPDRFSGSIDSSSNSASLTISGLKTEDEADYYCQSFDSTNPWVFGGGTKLTVL |
| 330 | NFMLTQPHSVSESPGKTVTISCRETELSRRLHYVRWYQQRPGSSPTTVIYEDDQRPSGVPDRFSGSIDSSSNSASLTISGLKTEDEADYYCQSFDSTNPWVFGGGTKLTVL |
| 316 | NFMLTQPHSVSESPGKTVTISCRGTGSSFHHKYVRWYQQRPGSSPTTVIYEDDQRPSGVPDRFSGSIDSSSNSASLTISGLKTEDEADYYCQSFDSTNPWVFGGGTKLTVL |

Fig. 7 (continued)

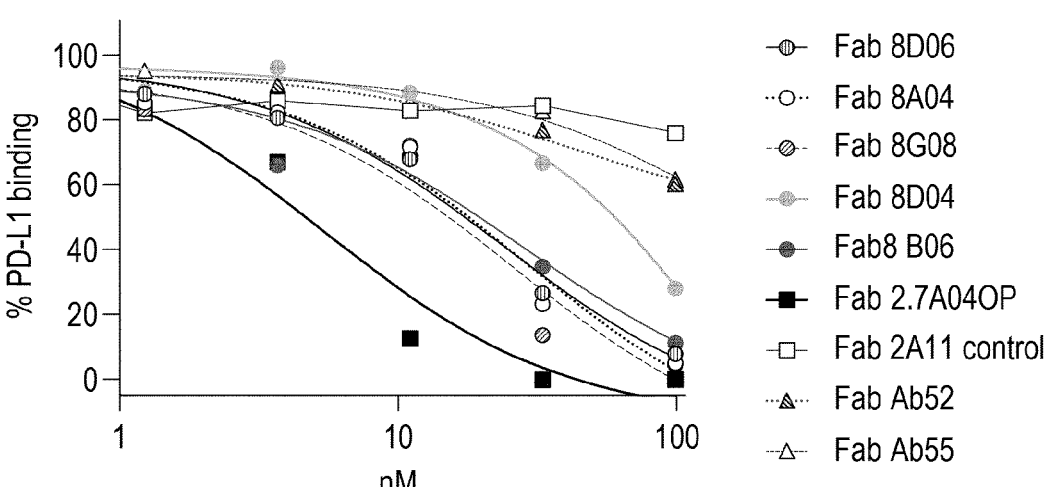
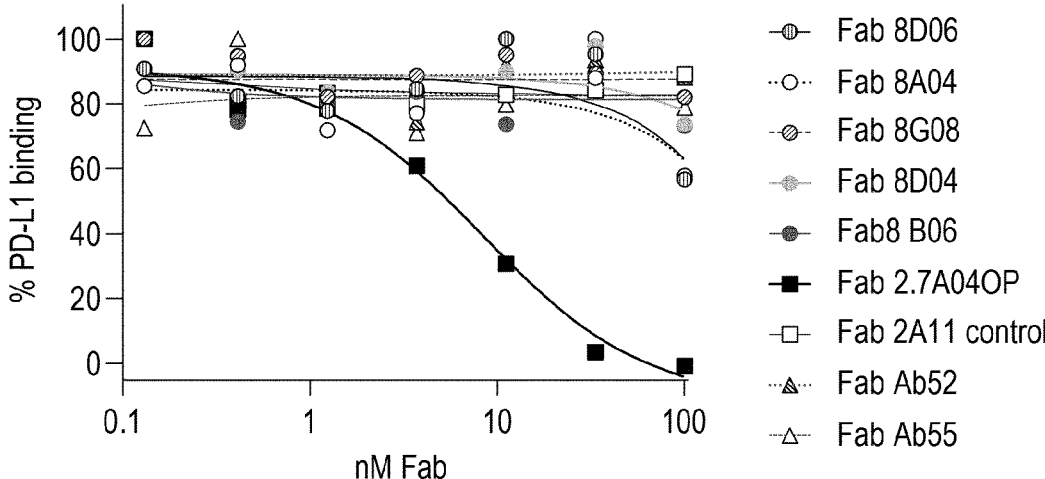
Fig. 8

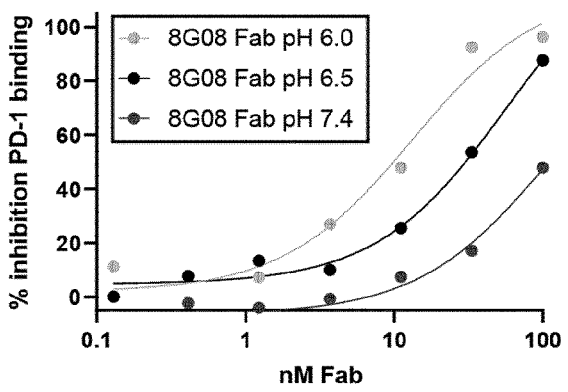
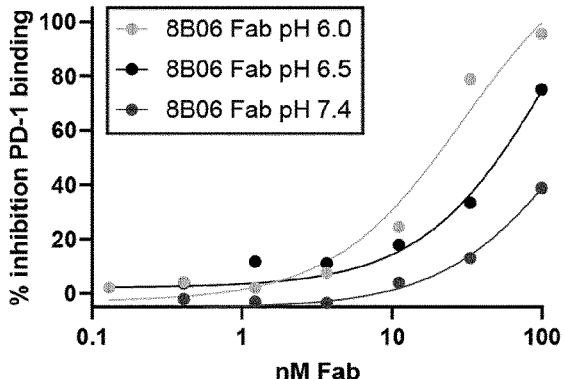
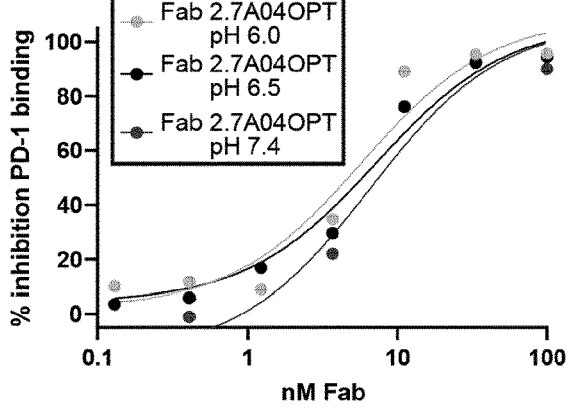
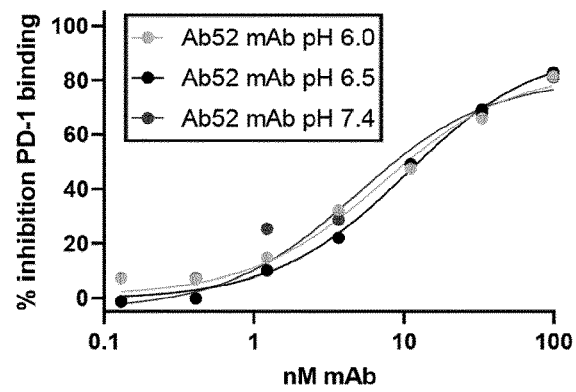
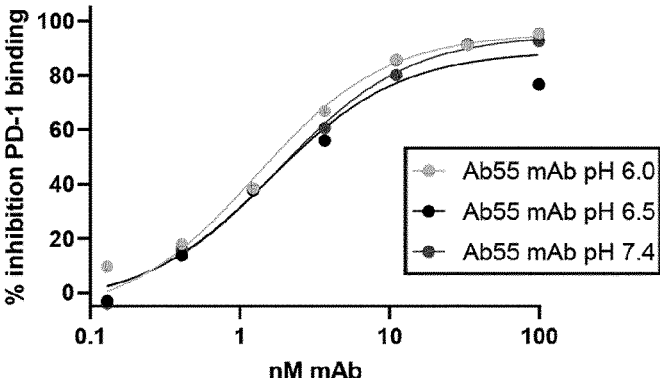
Fig. 9

ANTI-PD-L1 ANTIBODIES

FIELD OF THE INVENTION

The present invention relates to antigen binding molecules, particularly antibodies, fragments and variants thereof, that bind to the programmed death-ligand 1 (PD-L1) in a pH-dependant manner, competing with PD-L1 binding to the inhibitory receptor programmed death 1 polypeptide (PD-1) and co-stimulatory molecule CD80, and the use of said antigen binding molecules in treating and/or preventing diseases such as cancer.

BACKGROUND TO THE INVENTION

Co-stimulation with two distinct signals to T-cells is an important mechanism for coordinating and tightly regulating immune response activation of resting T lymphocytes by antigen-presenting cells (Mondino and Jenkins, J Leukoc Biol. 1994; 55:805-15). The initial antigen specific signal is transduced through the T-cell receptor (TCR) following recognition of foreign peptide antigens presented by MHC. The second signal is delivered to T-cells by co-stimulatory molecules expressed on antigen-presenting cells (APCs) and induce T-cells to clonally expand, secrete cytokines and effector function (Lenschow et al., Ann. Rev. Immunol. 1996; 14:233). In the absence of co-stimulation, T-cells can become refractory to antigen stimulation, do not mount an effective immune response and may result in exhaustion or tolerance to foreign antigens.

T-cells receive both positive and negative secondary co-stimulatory signals and the regulation of such signals is critical to maximize the host's protective immune responses, while maintaining immune tolerance and preventing auto-immunity. Negative secondary signals seem necessary for induction of T-cell tolerance, while positive signals promote T-cell activation. While the simple two-signal model still provides a valid explanation for naïve lymphocytes, a host's immune response is a dynamic process and co-stimulatory signals can also be provided to antigen-exposed T-cells.

The mechanism of co-stimulation therapeutically relevant as the manipulation of co-stimulatory signals has shown to provide a means to either enhance or terminate cell-based immune response. It has been discovered that T cell dysfunction or anergy occurs concurrently with an induced and sustained expression of the inhibitory receptor, programmed death 1 polypeptide (PD-1). Two PD-1 ligands have been described, PD-L1/B7H1/CD274 and PD-L2/B7-DC/CD273. PD-L1 is expressed at low levels on immune cells such as B cells, dendritic cells, macrophages and T cells and is up regulated following activation. PD-L1 is also expressed on non-lymphoid organs such as endothelial cells, heart, lung, pancreas, muscle, keratinocytes and placenta. The expression within non lymphoid tissues suggests that PD-L1 may regulate the function of self-reactive T and B cells as well as myeloid cells in peripheral tissues or may regulate inflammatory responses in the target organs. PD-L1 expression is mainly regulated by type 1 and 2 interferon which are major regulators of PD-L1 on endothelial and epithelial cells. PD-L1 is expressed in tumor samples and is associated with poor prognosis (Wang et al. Medicine 2017; 96:e6369). PD-L2/B7-DC cell surface expression is mainly restricted to macrophages and dendritic cells. PD-L1 is abundant in a variety of human cancers (Dong et al. Nat. Med 2002; 8:787) and the interaction between PD-1 and PD-L1 results in a decrease in tumor infiltrating lymphocytes, a decrease in T-cell receptor mediated proliferation, and immune evasion by the cancerous cells (Dong et al. J. Mol. Med. 2003; 81:281; Blank et al. Cancer Immunol. Immunother. 2005; 54:307; Konishi et. al. Clin. Cancer Res. 2004; 10:5094). Immune suppression can be reversed by inhibiting the local interaction of PD-1 with PD-L1 (Iwai et al. J Biomed. Sci. 2017; 24: 26). The inhibition of PD-L1 signalling has been shown to enhance T cell immunity for the treatment of cancer (Alsaab et al. Front. Pharmacol. 2017; 8:561).

Immunotherapy through checkpoint inhibitors is now standard practice for a growing number of cancer types. One anti-CTLA-4 antibody (ipilimumab), two anti-PD-1 antibodies (pembrolizumab and nivolumab) and three anti-PD-L1 antibodies (atezolizumab, avelumab and durvalumab) have been approved to date showing clear benefits through many clinical trials. Adverse events of an immune nature associated with these agents frequently affect the skin, colon, endocrine glands, lungs and liver. These immune related adverse events (AEs) occur across different tumor types: events of any grade happen in about 90% of patients treated with anti-CTLA-4 ipilimumab and approximately 70% of those treated with any anti-PD-1 or anti-PD-L1 antibody (Michot et al. Eur J Cancer 2016; 54:139). For combined checkpoint inhibitor treatment, the rates of grades 3-4 immune related AEs are significantly higher (Wolchok et al. N Engl J Med 2017; 377:1345).

Warburg first reported that cancer cells limit their energy metabolism largely to glycolysis, even in the presence of oxygen (Warburg Science 1956; 123:309). Increased glycolysis allows the diversion of glycolytic intermediates into various biosynthetic pathways, including those generating nucleosides and amino acids and this facilitates the biosynthesis of the macromolecules and organelles required for assembling new cells and supporting the active cell proliferation in neoplastic disease (Heiden et al. Science 2009; 324:1029). The consequence of increased intracellular production of lactic acid is extracellular tumor acidosis. To maintain an intracellular pH (pHi) that is slightly alkaline (~pH 7.4), tumor cells upregulate several proton extrusion mechanisms such as the Na+/H+ exchanger, HCO3-transporter and carbonic anhydrase IX (Gillies et al. J Magnetic Resonance Imaging 2002; 16:430). Excess protons are excreted into the extracellular matrix, causing the extracellular pH (pHe) of the tumor microenvironment to become acidic. In certain tumor types the pH has been measured to be as low as pH 6 to 6.5 (Gatenby and Gillies Nature Rev. Cancer 2004; 4:891; Muller-Klieser and Vaupel Adv. Physiol. Sci. 1981 25:253).

SUMMARY OF THE INVENTION

In order to reduce peripheral checkpoint inhibitor treatment toxicity as described above while enhancing tumor neutralization, the inventors have generated anti-PD-L1 Fabs that have reduced activity at physiological pH of 7.4 and have maximum activity at pH 6-6.5, the acidic pH of a tumor. The present invention is particularly useful in reducing pneumonitis, which is broadly defined as inflammation of the lung parenchyma, has been described in patients receiving anti-PD-1 or PD-L1 therapy either alone or in combination, and does occur more commonly in patients with lung cancer (Brahmer J et al. N Engl J Med 2015; 373: 123-135; Rivzi N A et a. J Clin Oncol 2015; 33: 15s).

The antigen binding molecules of the invention demonstrated significantly higher affinity for PD-L1 at acidic pH (pH 6.0) compared to physiological pH (pH 7.4). This contrasts with other PD-L1 binding molecules known in the art, which do not demonstrate pH specific binding and many in fact show lower affinity at pH 6.0 compared to pH 7.4.

The antigen binding molecules of the invention therefore have a much lower peripheral toxicity than PD-L1 antibodies known in the art. This means a tumour cell killing strategy (Fc mediated or toxic drug conjugate) can be employed against only tumour positive PD-L1 cells, without destruction of healthy cells. This reduces the significant side effects and peripheral checkpoint inhibitor treatment toxicity.

These anti-PD-L1 Fabs can be formatted as single agents or as bispecific formats with other relevant cancer or immune-oncology targets. In some embodiments, the antigen binding molecules are monovalent for PD-L1 binding.

The PD-L1 antibody or composition could be combined with a treatment regimen further comprising a traditional therapy selected from the group consisting of: radiation therapy, chemotherapy, targeted therapy, immunotherapy, hormonal therapy, angiogenesis inhibition and palliative care for cancer therapy. The chemotherapy treatment may be selected from the group consisting of: gemcitabine, cyclophosphamide, doxorubicin, paclitaxel, cisplatin.

The present inventors have identified antigen binding molecules that specifically bind PD-L1.

In one aspect the invention provides an anti-PD-L1 antigen binding molecule comprising:

a VLCDR1 having at least 80% identity to the amino acid sequence of any one of SEQ ID NOs 16, 12, 10, 14, 18, or 2.

In a further aspect the invention provides an antigen-binding molecule that specifically binds to PD-L1 and inhibits the binding of PD-L1 to an antigen-binding molecule of the invention.

In a further aspect the invention provides an antigen-binding molecule that specifically binds to an epitope of human PD-L1 wherein the epitope is comprised in SEQ ID NO: 19.

In a further aspect the invention provides an antigen-binding molecule that specifically binds to an epitope of cynomolgus PD-L1.

In a further aspect the invention provides an anti-PD-L1 antigen binding molecule, wherein the anti-PD-L1 antigen binding molecule is an affinity matured mutant of the antibody 2A09.

In a still further aspect the invention provides a pharmaceutical composition comprising an antigen binding molecule of the invention.

In a further aspect the invention provides a kit comprising an antigen binding molecule of the invention or a pharmaceutical composition of the invention, further comprising an additional therapeutically active agent.

In a further aspect the invention provides an antigen binding molecule of the invention, or a pharmaceutical composition of the invention, for use in the treatment or prevention of cancer.

In a still further aspect the invention provides a method for the treatment or prevention of a PD-L1-mediated disease or disorder comprising administering to the subject an antigen binding molecule or pharmaceutical composition of the invention, wherein the PD-L1-mediated disease or disorder is a cancer.

In a further aspect the invention provides a method of inhibiting the binding of human PD-L1 to PD-1 and/or CD80 or the binding of PD-L1 expressing cells to PD-1 and/or CD80, comprising contacting the human PD-L1 or PD-L1 expressing cell with an antigen-binding molecule of the invention.

In a further aspect the invention provides a nucleic acid encoding an antigen binding molecule of the invention.

In a further aspect of the invention, there is provided a vector or plasmid comprising a nucleic acid encoding an antigen binding molecule of the invention.

In a further aspect of the invention, there is provided a host cell comprising a vector or plasmid comprising a nucleic acid encoding an antigen binding molecule of the invention.

In a further aspect the invention provides a method of producing a cell that expresses an anti-PD-L1 antigen binding molecule, comprising transfecting said cell with a plasmid or vector comprising a nucleic acid of the invention.

In a further aspect the invention provides a method for the production of an anti-PD-L1 antigen binding molecule, comprising culturing a host cell in accordance with the invention in a cell culture medium under conditions to express the encoding nucleic acid sequence of the plasmid or vector inside the cell.

BRIEF DESCRIPTION OF FIGURES

FIG. 5 shows affinity matured anti-PD-L1 Fabs inhibition of PD-L1:PD-1 binding by ELISA at pH 7.4, 6.5 and 6.0 in KRB buffer. The OD was normalized to the negative control Fab 2A11 (anti-HEL).

FIG. 7 provides the heavy and light chain variable regions and CDRs of some of the antigen binding molecules of the invention.

FIG. 8 shows Fabs of Ab-52 and Ab-55 were compared in their ability to neutralise PD-L1 at pH 6 or pH 7.4 versus each of the 5 Fabs of the present invention (8B06, 8D06, 8G08, 8A04, 8D04).

FIG. 9 shows pH dependence neutralising activity of Ab-52 and Ab-55 mAbs.

DETAILED DESCRIPTION

Figure 1A:
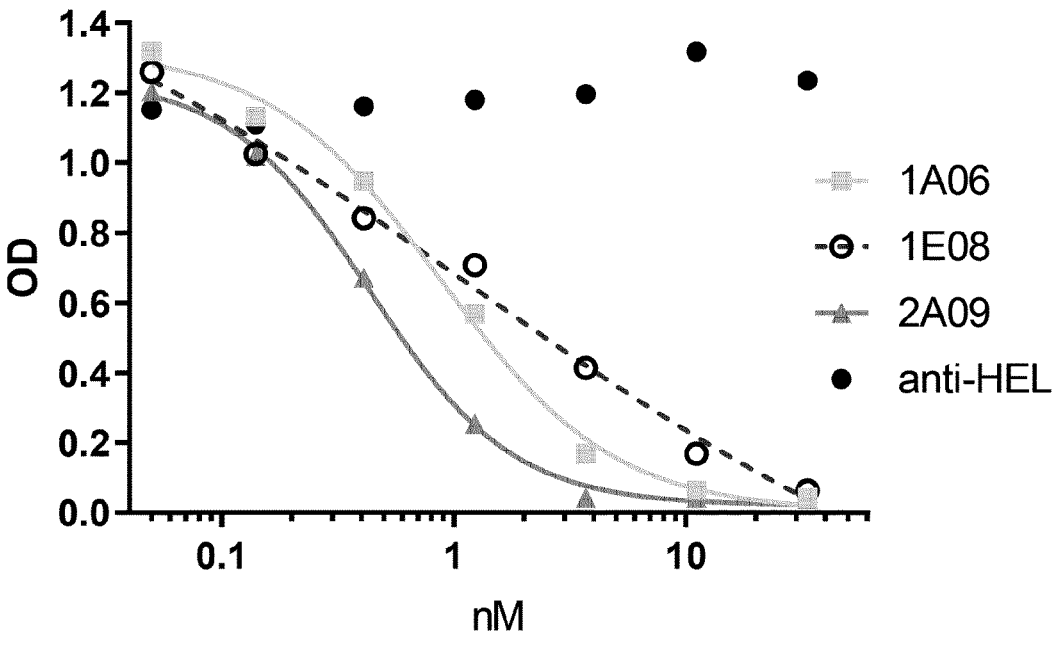
FIG. 1A shows the results of a PD-L1 neutralising ELISA of the three lead mAbs 1A06, 1E08 and 2A09. An anti-HEL mAb was used as a negative control

As used herein, an "antigen binding molecule" is a member of a pair of molecules which have binding specificity for one another. The members of an antigen binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of antigen binding pairs are antigen-antibody, biotin-avidin, hormone-hormone receptor, receptor-ligand and enzyme-substrate. The present invention is generally concerned with antigen-antibody type interactions. The antigen binding molecule used in the present invention binds with greater affinity to PD-L1, human PD-L1, cynomolgus PD-L1, an epitope of PD-L1, an epitope of hPD-L1 or an epitope of cynomolgus PD-L1 than to other molecules, i.e. It binds specifically to PD-L1, hPD-L1, cynomolgus PD-L1 an epitope of PD-L1, an epitope of hPD-L1 and/or an epitope of cynomolgus PD-L1. The binding affinity of the antigen binding molecule PD-L1, hPD-L1, cynomolgus PD-L1, an epitope of PD-L1, an epitope of hPD-L1 or an epitope of cynomolgus PD-L1 can be measured using the dissociation constant ($K_D$). The binding affinity of the antigen binding molecule to PD-L1, hPD-L1, cynomolgus PD-L1, an epitope of PD-L1, an epitope of hPD-L1 or an epitope of cynomolgus PD-L1 can also be measured using the association constant (Ka). The $K_D$ value of the antigen binding molecule for PD-L1 described herein will be lower than the $K_D$ value of the antigen binding molecule for non-PD-L1.

Antigen binding molecules which bind to PD-L1 and/or hPD-L1 include anti-PD-L1 antibodies. The antigen binding molecule used in the present invention is typically an antibody (including fragments thereof).

As used herein, PD-L1 may refer to human PD-L1 and/or cynomolgus PD-L1.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. Antibodies may be polyclonal or monoclonal. These can be derived from natural sources, or they may be partly or wholly synthetically produced. Antibodies are polypeptides that typically contain two identical heavy chains and two identical light chains, which are smaller than the heavy chains. In mammals there are two types of light chain, which are called lambda (λ) and kappa (κ). Each of the heavy chains and each of the light chains are composed of a variable region and a constant region. The heavy chain variable region is referred to as the VH region and the light chain variable region is referred to as the VL region. For kappa light chains, the VL region can also be referred to as the Vκ region. Each of the variable regions of the light and heavy chains comprise three complementarity determining regions (CDRs), CDR1, CDR2 and CDR3. These are named VLCDR1, VLCDR2, VLCDR3, VHCDR1, VHCDR2 and VHCDR3 respectively. Examples of antibodies are the immunoglobulin isotypes (e.g., IgG, IgE, IgM, IgD and IgA) and their isotypic subclasses; fragments which comprise an antigen binding domain, such as Fab, F(ab')2, Fv, scFv, dAb, Fd; and diabodies, are also contemplated in the present invention.

The antigen binding molecule of the invention is typically an antibody, more typically a monoclonal antibody. In a preferred embodiment, the antibody is a fully-human monoclonal antibody, in which the human constant region is employed. In some embodiments, the monoclonal antibody of the present invention is a humanised antibody.

Methods for the production of monoclonal antibodies are well known to the skilled person, for examples as described in Frenzel et al., "Expression of Recombinant Antibodies", *Front Immunol,* 2013, 4:217, the contents of which is hereby incorporated by reference.

The monoclonal antibodies of the present invention can be humanised by modifying the amino acid sequence of the antibody. Methods to reduce the immunogenicity of the antigen binding molecules of the invention include CDR grafting on to a suitable antibody framework scaffold or variable surface residues remodelling, e.g. by site-directed mutagenesis or other commonly used molecular biological techniques (Roguska et al Protein Eng. 9 895-904 (1996)).

Other methods applicable can include the identification of potential T-cell epitopes within the molecule, and the subsequent removal of these e.g. by site-directed mutagenesis (de-immunisation). Humanisation of the antigen binding molecule may be desired where the molecule is to be used as a therapeutic agent. Humanisation of the CDR regions or of the surrounding framework sequence can be carried out as desired.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced.

In one embodiment, the heavy chain variable region and/or the light chain variable region are at least 85% humanised, at least 90% humanized, at least 95% humanized, at least 96% humanized, at least 97% humanized, at least 98% humanized or at least 99% humanized. In some embodiments, the antibodies are conservatively humanised, for example to retain better antigen binding. In such conservatively humanised antibodies, fewer antibody substitutions may be made, compared to humanised antibodies.

The antigen binding molecules of the invention are, in some embodiments, deimmunised, for example using methods described in Jones et al., "Deimmunization of monoclonal antibodies", *Methods Mol Biol,* 2009, 525:405-23, the contents of which are hereby incorporated by reference. Deimmunisation removes T-cell epitopes from the sequences using a combined immunological and molecular biology technique.

In some embodiments of the invention, there is therefore provided a deimmunised anti-PD-L1 antigen binding molecule or antigen binding fragment thereof, wherein the anti-PD-L1 antigen binding molecule or antigen binding fragment thereof comprises deimmunised variants of the 6 CDR regions of an antibody selected from the group consisting of 2A09, 8G08, 8D06, 8A04, 8B06 and 8D04. In a further embodiment of the invention, there is provided a deimmunised anti-PD-L1 antigen binding molecule or antigen binding fragment thereof, wherein the anti-PD-L1 antigen binding molecule or antigen binding fragment thereof comprises deimmunised variants of the VH and/or VL sequences from an antibody selected from the group consisting of 2A09, 8G08, 8D06, 8A04, 8B06 and 8D04. In a still further embodiment of the invention, there is provided a deimmunised anti-PD-L1 antibody, wherein the anti-PD-L1 antibody is a deimmunised variant of an antibody selected from the group consisting of 2A09, 8G08, 8D06, 8A04, 8B06 and 8D04.

The antigen binding molecules and antigen binding fragments thereof are based on 1 parental antibody 2A09. In addition to the parental antibody, the invention is particularly concerned with affinity matured variants of the parental antibody. The invention is also based on antibody-fragments comprising one or more antigen binding domains from the antibodies of the invention, as well as further variants such as antibodies or antigen-binding fragments thereof having antigen binding domains containing 1 or more conservative amino acid substitutions. In one embodiment antibodies or antigen-binding fragments thereof having antigen binding domains containing from 1 to 10 conservative amino acid substitutions. In one embodiment antibodies or antigen-binding fragments thereof having antigen binding domains containing from 1 to 5 conservative amino acid substitutions. In one embodiment antibodies or antigen-binding fragments thereof having antigen binding domains containing from 1 to 2 conservative amino acid substitutions. All of the antigen binding molecules of the invention specifically bind PD-L1.

The antigen binding molecules of the invention, in particular antibodies, may be of any suitable type, including IgA, IgD, IgE, IgG, IgM and IgY, although IgG may be preferred. IgG1 backbones may be most preferred. In relevant embodiments, the constant region of the antibodies of the invention may be modified for advantageous effect, for example to increase stability and reduce Fc gamma receptor interaction.

Such advantageous modifications include modifications or substitutions in the Fc region, for example those that enhance effector cell killing function. Effector cell killing function refers to antibody dependant cell mediated cytotoxicity (ADCC), antibody dependant cellular phagocytosis (ADCP) and/or complement dependant cytotoxicity (CDC).

In one embodiment the Fc region is modified to enhance ADCC and/or ADCP and/or CDC activity. Enhancement refers to stronger ADCC and/or ADCP and/or CDC activity compared to the antibody before modification.

In one embodiment the Fc region is modified by protein engineering to enhance ADCC and/or ADCP and/or CDC activity. In one embodiment Fc receptor affinity can be increased by amino acid mutations that increase the affinity for C1q, which enhances CDC.

In another embodiment Fc receptor affinity can be increased by changing the glycosylation profile of the Fc region. In one embodiment the Fc region is modified by acfucosylation or under fucosylation to increase ADCC activity.

Fragments of antibodies and antigen binding molecules

The antigen binding molecule of the invention can be a fragment of an antibody, specifically an antigen-binding fragment of an antibody. The antigen binding fragments comprise one or more antigen binding regions. It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) 'diabodies', multivalent or multispecific fragments constructed by gene fusion (WO94/13804; P. Hollinger et al., Proc. Natl. Acad. Sci. USA 90: 6444-6448 (1993)). Typically, the fragment is a Fab, F(ab')2 or Fv fragment or an scFv molecule. In some embodiments, the fragment may be a Fab fragment.

A bispecific antibody is one which can bind to two target molecules simultaneously, such as two antigens or two epitopes. Bispecific antibodies may also be referred to as dual binding antibodies. Examples of bispecific antibody formats include, but are not limited to; (mAb)2, Fcab, F(mAb')2, quadromas, scFv (single chain variable fragments), bsDb (bispecific diabodies), scBsDb (single chain bispecific diabodies), BITE (bispecific T cell engagers), DART (dual affinity re-targeting antibodies), charge pairs, tandem antibodies, tandem scFv-Fc, Fab-scFv-Fc, Fab-scFv, minibodies, zybodies, DNL-F(ab)3 (dock-and-lock trivalent Fabs), bssdAb (bispecific single domain antibodies) and knobs-in-holes.

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, Current Opinion Biotechnol. 4:446-449 (1993)), e.g. prepared chemically or from hybrid hybridomas, or may be any of the bispecific antibody fragments mentioned below. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991).

Bispecific diabodies, as opposed to bispecific whole antibodies, may also be useful because they can be readily constructed and expressed in *E. coli*. Diabodies (and many other polypeptides such as antibody fragments) of appropriate binding specificities can be readily selected using phage display (WO94/13804) from libraries. If an arm of the diabody is to be kept constant, for instance, with a specificity directed against antigen X, then a library can be made where another arm is varied and an antibody of appropriate specificity selected.

In some embodiments, the antigen binding molecules of the invention are monovalent for PD-L1, for example a monovalent antibody fragment. A monovalent antigen binding molecule (also known as a monomeric antigen binding molecule) is an antigen binding molecule with only one binding site for an epitope or antigen. For example, a Fab, knob-in-hole, 1 arm IgG, scFv exhibit monovalent binding, whereas a complete monoclonal antibody with two Fab regions exhibits bivalent binding. When the antigen binding molecule is monovalent, the antigen binding molecule and the antigen bind in a 1:1 ratio. The present invention therefore provides monovalent antibodies or antibody fragments that specifically bind to PD-L1 in a pH-dependent manner.

In some embodiments, the antigen binding molecule is monovalent for PD-L1. This means the antigen binding molecule has a maximum of 1 binding site for PD-L1. Therefore, the antigen binding molecule binds a PD-L1 molecule in a ratio of 1:1. Monovalent antigen binding molecules are also generally monospecific. In such embodiments, the monovalent antigen binding molecule specifically binds to PD-L1 only. In some embodiments, the antibody binding molecule may comprise a monovalent binding site that specifically binds to PD-L1 in a ratio of 1:1, and one or more additional binding sites that specifically bind to an antigen that is different to PD-L1. For example, in some embodiments, the antigen binding molecule is a bispecific antigen binding molecule comprising a first binding site that is monovalent for PD-L1 (specifically binds PD-L1 in a ratio of 1:1) and a second binding site that specifically binds to a second, different, antigen. In another embodiments, the antigen binding molecule may be a bispecific antigen binding molecule comprising a first binding site that is monovalent for PD-L1 (specifically binds PD-L1 in a ratio of 1:1) and a second binding site that is monovalent for a second, different, antigen (specifically binds to the second, different antigen, in a ratio of 1:1). In such embodiments, the antigen binding molecules binds its antigens in a ratio of 1 antigen binding molecule to 2 antigen molecules, but still in a ratio of 1 antigen binding molecule to 1 PD-L1 molecule. Multi- and bispecific configurations are discussed elsewhere and it is directly contemplated the multi- and bispecific antigen binding molecules disclosed herein may be monovalent for PD-L1 (i.e. bind PD-L1 in a ratio of 1 bispecific antigen binding molecule to 1 PD-L1 molecule).

In some embodiments, the antigen binding molecules or antibodies of the invention may be bispecific for PD-L1 and another antigen or epitope. In one embodiment, the other antigen may be selected from the group consisting of a T cell costimulatory agonist or a T cell costimulatory antagonist. In one embodiment, the other antigen may be selected from the group consisting of CD47, SIRP alpha, CD25, TIGIT, ICOS, CD70, BTLA, GITR, LAG-3, TIM-3, CTLA-4, CD137, OX40, EGFR, TGF, VEGF and CD40.

In one embodiment the bispecific antigen binding molecule or antibody of the invention specifically binds to PD-L1 and specifically binds to an immune checkpoint inhibitor. In a further embodiment the bispecific antigen binding molecule or antibody of the invention specifically binds to PD-L1 and specifically binds to an immune checkpoint inhibitor. In a further embodiment the bispecific antigen binding molecule or antibody of the invention specifically binds to PD-L1 and specifically binds to an immune checkpoint inhibitor wherein the immune checkpoint inhibitor is selected from the group consisting of PD-1, CTLA-4, TIM-3, CD137, CD40, LAG-3, VISTA, ICOS, BTLA, GITR and TIGIT.

In one embodiment the bispecific antigen binding molecule or antibody of the invention specifically binds to PD-L1 and specifically binds to an immune effector. In a further embodiment the bispecific antigen binding molecule or antibody of the invention specifically binds to PD-L1 and specifically binds to an immune effector selected from the group consisting of OX40, EGFR, TGF, VEGF, CD40, CD137, GITR, CXCR3, BTLA, CD3, CD70, CD25, CD47, SIRP alpha and CD27.

In one embodiment the bispecific antigen binding molecule or antibody of the invention specifically binds to PD-L1 and also acts to recruit and engage other cells, such as T cells. The dual-antigen specificity of bispecific antigen binding molecules or antibodies enables simultaneous binding to a PD-L1 specific antigen along with an antigen present on a cytotoxic T-cell. This directs the cytotoxic activity of the T cell to the tumour cell via the engaging activity of the bispecific antigen binding molecule or antibody. In a further embodiment the bispecific antigen binding molecule or antibody of the invention specifically binds to PD-L1 and specifically binds to a T cell recruiter. T cell recruiter molecules include but are not limited to CD3 and CD137.

Antibodies or antigen binding molecules of the invention may also be trispecific. Trispecific antigen binding molecules or antibodies of the invention comprise a binding site specific for PD-L1, and a binding site to recruit T cells. In one embodiment such antigen binding molecules or antibodies comprise a binding site specific for PD-L1, and a binding site specific for CD3. Additionally, in these embodiments the Fc region of the trispecific antigen binding molecule or antibody can also bind to a Fc receptor on an accessory cell. The recruitment of additional accessory cells such as monocytes, macrophage, NK cells and/or dendritic cells makes trispecific antigen binding molecules or antibodies more potent at destroying tumour cells than other antibodies since the trispecific antibodies enable the linking of T cells, accessory cells and tumour cells. In one embodiment, the trispecific antigen binding molecule or antibody comprises one binding site specific for PD-L1, one binding site specific for CD3 and an intact Fc region that can interact with Fc receptors on monocytes, macrophage, NK cells and dendritic cells.

Antibodies or antigen binding molecules of the invention may also be conjugated to other molecules such as drugs, prodrugs or toxic moieties. This serves to target these molecules to the tumour cell. Since the antibodies or antigen binding molecules of the invention have a much lower peripheral toxicity than other PD-L1 antibodies, a tumour cell killing strategy can be employed against only tumour positive PD-L1 cells, without destruction of healthy cells. In one embodiment a PD-L1 specific antigen binding molecule of the invention is conjugated to a molecule selected from the group consisting of cytotoxins (e.g. maytansanoid, auristatin, dolastatin, cryptophycin, calicheamicin, duocarmycin, pyrolobenodiazepine), protein toxins (e.g. *Pseudomonas* exotoxin, diphtheria toxin, ribosome-inactivating proteins), and radionuclides (e.g. $^{90}$Y, $^{111}$In).

Identity and Homology

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptides or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic add sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100). Generally, references to % identity herein refer to % identity along the entire length of the molecule, unless the context specifies or implies otherwise.

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Typically, the amino acid sequence of the CDRs of the antigen binding molecules provided in the invention have at least 70% identity, for example using the default parameters of the BLAST computer program (Atschul et al., J. Mol. Biol. 215, 403-410 (1990)) provided by HGMP (Human Genome Mapping Project), at the amino acid level, to the amino acid sequences of the CDRs described below. More typically, the CDR sequence has at least 75%, 80%, 85%, 90%, 91%, 92%, 93%, 94%, 95%, 96%, 97%, 98% or at least 99% identity, at the amino acid level, to the sequences shown below. Typically, each of the CDR sequences of the antigen binding molecule used in the invention has this level of identity to the amino acid sequences of the CDRs set out below. Alternatively, any 1, 2, 3, 4 or 5 of the CDRs of the antigen binding molecule used in the invention has this level of identity to the amino acid sequences of the CDRs set out below.

The amino acid sequence of the VH and VL regions of the antigen binding molecules provided in the invention have at least 70% identity, for example using the default parameters of the BLAST computer program (Atschul et al., J. Mol. Biol. 215, 403-410 (1990)) provided by HGMP (Human Genome Mapping Project), at the amino acid level, to the amino acid sequences of the VH and VL regions described below. More typically, the VH and VL regions have at least 75%, 80%, 85%, 90%, 91%, 92%, 93%, 94%, 95%, 96%, 97%, 98% or at least 99% identity, at the amino acid level, to the sequences shown below. Typically, each of the VH and VL regions of the antigen binding molecule used in the invention has this level of identity to the amino acid sequences of the VH and VL regions set out below. Alternatively, only one of the VH and VL regions of the antigen binding molecule used in the invention has this level of identity to the amino acid sequences of the VH and VL regions set out below.

Identity, as used herein, may be used interchangeably with "homology" and "similarity". References to particular % identities apply equally to % homology and % similarity. Homology and similarity may be determined using appropriate algorithms, such as FASTA, BLAST and Gapped BLAST. Software for performing these analyses are publicly available.

Variants

The present invention also extends to variants of peptide sequences referred to below. As used herein the term "variant" relates to proteins that have a similar amino acid sequence and/or that retain the same function. For instance, the term "variant" encompasses proteins or polypeptides which include one or more amino acid additions, deletions, substitutions or the like. An example of a variant of the present invention is a protein comprising a peptide as defined below, apart from the substitution of one or more amino acids with one or more other amino acids. Amino acid substitutions may be made to, for example, reduce or eliminate liabilities in the amino acid sequences. Alternatively, amino acid substitutions may be made to improve antigen affinity or to humanise or deimmunise the antibodies, if required. Affinity matured variants, humanised variants and deimmunised variants of the specified antibodies are provided herein, as well as variants comprising amino add substitutions to reduce or eliminate any liabilities in the sequences of the antibodies.

Substitutions

The skilled person is aware that various amino acids have similar properties. One or more such amino acids of a substance can often be substituted by one or more other such amino acids without eliminating a desired activity of that substance.

Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Using the three letter and one letter codes the naturally occurring amino acids may be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

Amino acid deletions or insertions can also be made relative to the amino acid sequence for the fusion protein referred to below. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

In some embodiments, the following amino acids can be exchange for each other for conservative amino acid substitutions:

| Class | Exchangeable amino acids |
|---|---|
| Aliphatic | Glycine, Alanine, Valine, Leucine, Isoleucine |
| Hydroxyl or Sulfur/ Selenium-containing | Serine, Cysteine, Threonine, Methionine |
| Aromatic | Phenylalanine, Tyrosine, Tryptophan |
| Basic | Histidine, Lysine, Arginine |
| Acidic and their Amide | Aspartate, Glutamate, Asparagine, Glutamine |

Therefore, references to "conservative" amino acid substitutions refer to amino acid substitutions in which one or more of the amino acids in the sequence of the antibody (e.g. In the CDRs or in the VH or VL sequences) is substituted with another amino acid in the same class as indicated above. Conservative amino acid substitutions may be preferred in the CDR regions to minimise adverse effects on the function of the antibody. However, conservative amino acid substitutions may also occur in the framework regions.

Amino acid changes relative to the sequence given below can be made using any suitable technique e.g. by using site-directed mutagenesis or solid-state synthesis.

It should be appreciated that amino acid substitutions or insertions within the scope of the present invention can be made using naturally occurring or non-naturally occurring amino acids, although naturally occurring amino acids may be preferred. Whether or not natural or synthetic amino acids are used, it is preferred that only L-amino acids are present.

In one embodiment of the invention there is provided an antigen binding molecule, or antigen binding fragment thereof, of the invention comprising from 1 to 10, preferably from 1 to 5, more preferably from 1 to 2 amino acid substitutions in the antibody binding domain or antigen binding domains. For example, in one embodiment of the invention, there is provided an anti-PD-L1 antibody or antigen binding fragment thereof, wherein the anti-PD-L1 antibody antigen binding fragment thereof comprises the 6 CDR regions of an antibody selected from the group consisting of 2A09, 8G08, 8D06, 8A04, 8B06 and 8D04, optionally wherein the antigen binding molecule has from 1 to 10 amino acid substitutions across all of its CDR regions, preferably from 1 to 5 amino acid substitutions across all of its CDR regions. In a further embodiment of the invention, there is provided an anti-PD-L1 antigen binding molecule or antigen binding fragment thereof, wherein the anti-PD-L1 antibody antigen binding fragment thereof comprises the VH and VL sequences of an antibody selected from the group consisting of 2A09, 8G08, 8D06, 8A04, 8B06 and 8D04, optionally wherein the antigen binding molecule has from 1 to 10 amino acid substitutions across its VH and VL sequences, preferably from 1 to 5 amino acid substitutions across its VH and VL sequences. In a still further embodiment of the invention, there is provided an anti-PD-L1 antibody, wherein the anti-PD-L1 antibody is an antibody selected from the group consisting of 2A09, 8G08, 8D06, 8A04, 8B06 and 8D04, wherein the antibody has from 1 to 10 amino acid substitutions, preferably from 1 to 5 amino acid substitutions. Substitutions are of course substitutions with reference to the original CDR or variable chain sequences of the starting antibody.

In some embodiments, the one or more amino acid substitutions are in the CDR region or regions. In other embodiments, the one or more amino acid substitutions are in the framework regions, i.e. in the variable heavy and light chains but not in the CDR region or regions. In other embodiments, the one or more amino acid substitutions may be at any position in the variable heavy and/or variable light regions. In some embodiments, the amino acid substitutions do not adversely affect the binding specificity and/or affinity of the antibody. Accordingly, the variant antibody may have the same or superior functional profile as the antibody from which is it derived.

For example, in some embodiments there is provided an anti-PD-L1 antibody, wherein the anti-PD-L1 antibody is an antibody selected from the group consisting of 2A09, 8G08, 8D06, 8A04, 8B06 and 8D04, wherein the antibody has from 1 to 10 amino acid substitutions across its all of its framework regions, preferably from 1 to 5 amino acid substitutions across its all of its framework regions (i.e. the substitutions appear in the framework regions relative to reference antibody, and the CDR sequences are unchanged).

Affinity Matured Variants

Other variants that are within the scope of the present invention include antigen binding molecules of the invention that are modified to have increased affinity for PD-L1 or epitopes of PD-L1. In one embodiment, the antigen binding molecule of the invention is an affinity-matured antibody. In one embodiment, the antigen binding molecules of the invention are fully human affinity matured antibodies.

Any known methods can be used to increase the affinity of the antigen binding molecules of the invention to generate affinity-matured antibodies or fully human affinity matured antibodies with an increased affinity for PD-L1 or epitopes of PD-L1.

The present invention provides affinity matured variants of the provided antigen binding agents. The affinity matured variants bind to PD-L1 with greater affinity than the parental antibody. Preferably the produced antibody binds to PD-L1 with at least 20%, at least 30%, at least 40%, more preferably at least 50% greater affinity than the parental antibody binds to PD-L1, for example as measured by the Kd.

In some embodiments the invention provides a method of preparing antigen binding molecules of the invention comprising providing an antigen binding molecule as herein described (e.g., anti-PD-L1 binding molecule or antibody or an antigen binding fragment or variant thereof), and subjecting the antibody to affinity maturation, wherein the antibody produced binds to PD-L1 with greater affinity than the parental antibody. Preferably the produced antibody binds to PD-L1 with at least 20%, at least 30%, at least 40%, more preferably at least 50% greater affinity than the parental antibody binds to PD-L1, for example as measured by the Kd. Methods for measuring affinity are known in the art and described in the Examples below. The affinity matured antibodies produced by such methods can be formulated and used as described herein for the other anti-PD-L1 binding molecules.

Affinity maturation may be carried out according to any suitable method known to the skilled person. For example, in vitro antibody display systems are widely used for the generation of specific antibodies with high affinity. In these systems, the phenotype (i.e., the antibody fragment) is coupled to the genotype (i.e., the antibody gene) allowing the direct determination of the sequence of the antibody. Several systems have been developed to achieve display of antibody repertoires to allow subsequent selection of binders and by increasing the stringency of selection allows for the selection of higher and higher affinity variants. The antibody fragments can be expressed in yeast, ribosomes, phage display particles or by direct coupling to DNA.

Current antibody affinity maturation methods belong to two mutagenesis categories: stochastic and non-stochastic. Error-prone polymerase chain reaction (PCR), mutator bacterial strains, and saturation mutagenesis are typical examples of stochastic mutagenesis methods. Non-stochastic techniques often use alanine-scanning or site-directed mutagenesis to generate limited collections of specific variants. In addition, shuffling approaches to obtain shuffled variants of the parent antibody can also be used to improve antibodies affinity further.

Accordingly, in one embodiment of the invention, the method of affinity maturation is selected from the group consisting of stochastic mutagenesis (for example error-prone polymerase chain reaction (PCR), mutator bacterial strains, or saturation mutagenesis), non-stochastic mutagenesis (for example alanine-scanning or site-directed mutagenesis), shuffling (for example DNA shuffling, chain shuffling or CDR shuffling) and the use of the CRISPR-Cas9 system to introduce modifications.

Affinity maturation methods are described in, for example, Rajpal et al., Proc Natl Acad Sci USA, 2005, 102(24):8466-71, Steinwand et al., MAbs, 2014, 6(1):204-

18, as well as in Handbook of Therapeutic Antibodies, Wiley, 2014, Chapter 6, Antibody Affinity (pages 115-140).

In some embodiments there is provided a method of preparing a pharmaceutical composition comprising providing an antibody prepared according to a method above, (i.e. for producing an antibody by affinity maturation) and co-formulating the antibody with at least one or more pharmaceutically acceptable excipients. The antibody used in the preparation of the pharmaceutical composition can be an affinity matured variant of 2A09. The antibody used in the preparation of the pharmaceutical composition can be an affinity matured variant of 8G08, 8D06, 8A04, 8B06 or 8D04. The pharmaceutical compositions produced by such methods can be used in the methods of treatment of the present invention as described herein for the other anti-PD-L1 binding molecules. There are therefore provided antigen binding molecules that are affinity matured mutants or variants of the antigen binding molecules of the invention. For example, in one embodiment there is provided an affinity-matured variant of an antibody selected from the group consisting of 2A09, 8G08, 8D06, 8A04, 8B06 and 8D04. Generally, the affinity matured mutants have a higher affinity for PD-L1 than the parent antibody (the antibody from which the mutant is derived). Also provided by the present invention are antigen binding molecules and antibodies obtainable or obtained by affinity maturation of an antigen binding molecule or antibody of the invention.

Manufacturing Liabilities

Therapeutic proteins such as antibodies are heterogenous and complex by nature due to chemical modifications and post-translational modifications (PTMs). Modifications can be caused by a number of factors such as the host cell system, processes used in manufacture or conditions during storage or manufacture. Modifications can relate to the chemical stability of the molecule itself or the aggregation potential and the effect this has on intrinsic physical stability of the antibody. Amino acid motifs or residues in a given antibody sequence that may undergo spontaneous modification during manufacture or storage are referred to as liabilities. Accordingly, mutations may be made to the antibody sequence to address the liabilities to reduce the susceptibility of the antibody to modification and degradation.

Such modifications as a result of liabilities in the antibody sequences may include glycosylation, deamidation, oxidation and variations of C- and N-termini. Such modifications may arise during manufacture. Certain residues and structural or sequence motifs are more liable to certain modifications. Examples of such liabilities to modification include Asn N-linked glycosylation, Ser/Thr O-linked glycosylation, Asn deamidation, Asp isomerisation/fragmentation, Lys glycation, Met/Trp oxidation, free thiol groups, pyro-glutamates, C-terminal Lys.

A skilled person is aware that computational tools can be used to predict and identify structural and sequence liabilities which could potentially result in modifications. To minimise the occurrence of modifications alterations to the manufacturing process can be made. Protein engineering may also be considered to reduce the risk. For example, selective mutation of these liabilities can help to identify and reduce the risk of a modification endangering the stability of an antibody.

Aspartic acid residues (Asp) may undergo spontaneous modification. Asp containing motifs, such as Asp-Gly sequences may undergo spontaneous isomerization to form isoaspartic acid. Formation of isoaspartate may debilitate or completely abrogate the binding of the antibody. This is of additional importance if the Asp residue appears in the CDR of an antibody.

Aspartic acid residues (Asp) can therefore be substituted with any naturally occurring amino acid to reduce this liability to modification. Optionally, aspartic acid residues (Asp) can be substituted with alanine (Ala), glutamine (Gin) or glutamic acid (Glu) to reduce this liability to modification. Optimization of production/formulation can also be investigated to reduce isomerization. Alternatively, Asp-Gly motifs may be modified by substituting the glycine residue with another naturally occurring amino acid to inhibit deamidation, rather than by substitution of the Asp residue.

Methionine residues (Met) may undergo spontaneous modification. The presence of methionine (Met) in a CDR, especially if exposed to solvent, can create a problem if the methionine is oxidized and this interferes with binding. Methionine residues can therefore be substituted with any other naturally occurring amino acid to reduce this liability to modification. Methionine residues may preferably be substituted with Ala or Leu. Optimization of production/formulation can also be investigated to reduce oxidation.

TABLE 1

Non-limiting list of potential targets for sequence modification
in the antigen binding molecules of the invention:

|  | 8A04 | 8B06 | 8G08 | 8D06 | 2A09 | 8D04 |
|---|---|---|---|---|---|---|
| VLCDR1 | Met 23 | — | — | — | — | — |
| VLCDR2 | — | — | — | — | — | — |

TABLE 1-continued

Non-limiting list of potential targets for sequence modification
in the antigen binding molecules of the invention:

|  | 8A04 | 8B06 | 8G08 | 8D06 | 2A09 | 8D04 |
|---|---|---|---|---|---|---|
| VLCDR3 | Asp 95 | Asp 95 | Asp 95 | Asp 95 | Asp 95 | Asp 95 |
| VHCDR1 | — | — | — | — | — | — |
| VHCDR2 | Asp 54, Asp 62 | Asp 54, Asp 62 | Asp 54, Asp 62 | Asp 54, Asp 62 | Asp 54, Asp 62 | Asp 54, Asp 62 |
| VHCDR3 | Asp 110 | Asp 110 | Asp 110 | Asp 110 | Asp 110 | Asp 110 |
| VL (FR1) | Met 3 | Met 3 | Met 3 | Met 3 | Met 3 | Met 3 |

Therefore, variant antibodies derived from any of 8A04, 8B06, 8G08, 8D06, 8D04 and 2A09 but comprising one or more amino substitutions to address one or more of the liabilities summarised above are also provided herein.

For example, for any antigen binding molecules defined by one or more amino acid sequences herein, if there are one or more Met residues present, the one or more Met residues may each and independently be substituted with an Ala residue or a Leu residue. If there are one or more Asp residues present, the one or more Asp residues may each and independently be substituted with an Ala residue, a Gln residue, or a Glu residue.

Summary of Antigen Binding Molecules Provided

A summary of the antigen binding molecules provided by the present invention is provided below, with identification of the assigned SEQ ID NO. in the accompanying sequence listing. Antigen binding variants, derivatives and fragments thereof are also provided as part of the present invention:

TABLE 2

Summary of parental fully human antibody 2A09_WT and
fully human affinity matured versions of this antibody

| Antibody | SEQ ID NOs | | | | | | | |
|---|---|---|---|---|---|---|---|---|
|  | VL | VLCDR1 | VLCDR2 | VLCDR3 | VH | VHCDR1 | VHCDR2 | VHCDR3 |
| 2A09_WT | 1 | 2 | 3 | 4 | 5 | 6 | 7 | 8 |
| 8G08 | 9 | 10 | 3 | 4 | 5 | 6 | 7 | 8 |
| 8D06 | 11 | 12 | 3 | 4 | 5 | 6 | 7 | 8 |
| 8A04 | 13 | 14 | 3 | 4 | 5 | 6 | 7 | 8 |
| 8B06 | 15 | 16 | 3 | 4 | 5 | 6 | 7 | 8 |
| 8D04 | 17 | 18 | 3 | 4 | 5 | 6 | 7 | 8 |

Variants are Also Provided, Including at Least the Following Variants:

TABLE 3

Summary of variant antibodies derived from any of 8A04, 8B06, 8G08, 8D06, 8D04 and 2A09_WT comprising
one or more amino substitutions to address one or more of the liabilities summarised below.

| Antibody | SEQ ID NOs | | | | | | | | | |
|---|---|---|---|---|---|---|---|---|---|---|
|  | VL | VL_substi-tution1 | VL_substi-tution2 | VL_substi-tution3 | VLCDR1 | VLCDR1_substi-tution1 | VLCDR1_substi-tution2 | VLCDR1_substi-tution3 | VLCDR2 | VLCDR3 |
| 2A09_WT | 1 | 20 | 21 | 22 | 2 | — | — | — | 3 | 4 |
| 8G08 | 9 | 35 | 36 | 37 | 10 | — | — | — | 3 | 4 |
| 8D06 | 11 | 38 | 39 | 40 | 12 | — | — | — | 3 | 4 |
| 8A04 | 13 | 41 | 42 | 43 | 14 | 44 | 45 | 46 | 3 | 4 |
| 8B06 | 15 | 47 | 48 | 49 | 16 | — | — | — | 3 | 4 |
| 8D04 | 17 | 50 | 51 | 52 | 18 | — | — | — | 3 | 4 |

TABLE 3-continued

Summary of variant antibodies derived from any of 8A04, 8B06, 8G08, 8D06, 8D04 and 2A09_WT comprising
one or more amino substitutions to address one or more of the liabilities summarised below.

| | SEQ ID NOs | | | | | | | | |
|---|---|---|---|---|---|---|---|---|---|
| Antibody | VLCDR3_substitution1 | VLCDR3_substitution2 | VLCDR3_substitution3 | VH | VH_substitution1 | VH_substitution2 | VH_substitution3 | VHCDR1 | VHCDR2 |
| 2A09_WT | 23 | 24 | 25 | 5 | 26 | 27 | 28 | 6 | 7 |
| 8G08 | 23 | 24 | 25 | 5 | 26 | 27 | 28 | 6 | 7 |
| 8D06 | 23 | 24 | 25 | 5 | 26 | 27 | 28 | 6 | 7 |
| 8A04 | 23 | 24 | 25 | 5 | 26 | 27 | 28 | 6 | 7 |
| 8B06 | 23 | 24 | 25 | 5 | 26 | 27 | 28 | 6 | 7 |
| 8D04 | 23 | 24 | 25 | 5 | 26 | 27 | 28 | 6 | 7 |

| | SEQ ID NOs | | | | | | |
|---|---|---|---|---|---|---|---|
| Antibody | VHCDR2_substitution1 | VHCDR2_substitution2 | VHCDR2_substitution3 | VHCDR3 | VHCDR3_substitution1 | VHCDR3_substitution2 | VHCDR3_substitution2 |
| 2A09_WT | 29 | 30 | 31 | 8 | 32 | 33 | 34 |
| 8G08 | 29 | 30 | 31 | 8 | 32 | 33 | 34 |
| 8D06 | 29 | 30 | 31 | 8 | 32 | 33 | 34 |
| 8A04 | 29 | 30 | 31 | 8 | 32 | 33 | 34 |
| 8B06 | 29 | 30 | 31 | 8 | 32 | 33 | 34 |
| 8D04 | 29 | 30 | 31 | 8 | 32 | 33 | 34 |

For example, variants of 8G08 provided herein include variants having a VL of SEQ ID NO: 35 and a VH of SEQ ID NO: 26, or a VL of SEQ ID NO: 36 and a VH of SEQ ID NO: 27, or a VL of SEQ ID NO: 37 and a VH of SEQ ID NO: 28. Variants of 8D06 provided herein include variants having a VL of SEQ ID NO: 38 and a VH of SEQ ID NO: 26, or a VL of SEQ ID NO: 39 and a VH of SEQ ID NO: 27, or a VL of SEQ ID NO: 40 and a VH of SEQ ID NO: 28. Variants of 8A04 provided herein include variants having a VL of SEQ ID NO: 41 and a VH of SEQ ID NO: 26, or a VL of SEQ ID NO: 42 and a VH of SEQ ID NO: 27, or a VL of SEQ ID NO: 43 and a VH of SEQ ID NO: 28. Variants of 8506 provided herein include variants having a VL of SEQ ID NO: 47 and a VH of SEQ ID NO: 26, or a VL of SEQ ID NO: 48 and a VH of SEQ ID NO: 27, or a VL of SEQ ID NO: 49 and a VH of SEQ ID NO: 28. Variants of 8A04 provided herein include variants having a VL of SEQ ID NO: 50 and a VH of SEQ ID NO: 26, or a VL of SEQ ID NO: 51 and a VH of SEQ ID NO: 27, or a VL of SEQ ID NO: 52 and a VH of SEQ ID NO: 28. Variants of 2A09 provided herein include variants having a VL of SEQ ID NO: 20 and a VH of SEQ ID NO: 26, or a VL of SEQ ID NO: 21 and a VH of SEQ ID NO: 27, or a VL of SEQ ID NO: 22 and a VH of SEQ ID NO: 28.

Other variants of 8G08 provided herein include variants having:

a VLCDR1 of SEQ ID NO: 10, a VLCDR2 of SEQ ID NO: 3, a VLCDR3 of SEQ ID NO: 23, a VHCDR1 of SEQ ID NO: 6, a VHCDR2 of SEQ ID NO: 29, and a VHCDR3 of SEQ ID NO: 32;

a VLCDR1 of SEQ ID NO: 10, a VLCDR2 of SEQ ID NO: 3, a VLCDR3 of SEQ ID NO: 24, a VHCDR1 of SEQ ID NO: 6, a VHCDR2 of SEQ ID NO: 30, and a VHCDR3 of SEQ ID NO: 33; or a VLCDR1 of SEQ ID NO: 10, a VLCDR2 of SEQ ID NO: 3, a VLCDR3 of SEQ ID NO: 25, a VHCDR1 of SEQ ID NO: 6, a VHCDR2 of SEQ ID NO: 31, and a VHCDR3 of SEQ ID NO: 34.

Other variants of 8D06 provided herein include variants having:

a VLCDR1 of SEQ ID NO: 12, a VLCDR2 of SEQ ID NO: 3, a VLCDR3 of SEQ ID NO: 23, a VHCDR1 of SEQ ID NO: 6, a VHCDR2 of SEQ ID NO: 29, and a VHCDR3 of SEQ ID NO: 32;

a VLCDR1 of SEQ ID NO: 12, a VLCDR2 of SEQ ID NO: 3, a VLCDR3 of SEQ ID NO: 24, a VHCDR1 of SEQ ID NO: 6, a VHCDR2 of SEQ ID NO: 30, and a VHCDR3 of SEQ ID NO: 33; or a VLCDR1 of SEQ ID NO: 12, a VLCDR2 of SEQ ID NO: 3, a VLCDR3 of SEQ ID NO: 25, a VHCDR1 of SEQ ID NO: 6, a VHCDR2 of SEQ ID NO: 31, and a VHCDR3 of SEQ ID NO: 34.

Other variants of 8A04 provided herein include variants having:

a VLCDR1 of SEQ ID NO: 44, a VLCDR2 of SEQ ID NO: 3, a VLCDR3 of SEQ ID NO: 23, a VHCDR1 of SEQ ID NO: 6, a VHCDR2 of SEQ ID NO: 29, and a VHCDR3 of SEQ ID NO: 32;

a VLCDR1 of SEQ ID NO: 45, a VLCDR2 of SEQ ID NO: 3, a VLCDR3 of SEQ ID NO: 24, a VHCDR1 of SEQ ID NO: 6, a VHCDR2 of SEQ ID NO: 30, and a VHCDR3 of SEQ ID NO: 33; or a VLCDR1 of SEQ ID NO: 46, a VLCDR2 of SEQ ID NO: 3, a VLCDR3 of SEQ ID NO: 25, a VHCDR1 of SEQ ID NO: 6, a VHCDR2 of SEQ ID NO: 31, and a VHCDR3 of SEQ ID NO: 34.

Other variants of 8506 provided herein include variants having:

a VLCDR1 of SEQ ID NO: 16, a VLCDR2 of SEQ ID NO: 3, a VLCDR3 of SEQ ID NO: 23, a VHCDR1 of SEQ ID NO: 6, a VHCDR2 of SEQ ID NO: 29, and a VHCDR3 of SEQ ID NO: 32;

a VLCDR1 of SEQ ID NO: 16, a VLCDR2 of SEQ ID NO: 3, a VLCDR3 of SEQ ID NO: 24, a VHCDR1 of SEQ ID NO: 6, a VHCDR2 of SEQ ID NO: 30, and a VHCDR3 of SEQ ID NO: 33; or a VLCDR1 of SEQ ID NO: 16, a VLCDR2 of SEQ ID NO: 3, a VLCDR3 of SEQ ID NO: 25, a VHCDR1 of SEQ ID NO: 6, a VHCDR2 of SEQ ID NO: 31, and a VHCDR3 of SEQ ID NO: 34.

Other variants of 8D04 provided herein include variants having:

a VLCDR1 of SEQ ID NO: 16, a VLCDR2 of SEQ ID NO: 3, a VLCDR3 of SEQ ID NO: 23, a VHCDR1 of SEQ ID NO: 6, a VHCDR2 of SEQ ID NO: 29, and a VHCDR3 of SEQ ID NO: 32;

a VLCDR1 of SEQ ID NO: 16, a VLCDR2 of SEQ ID NO: 3, a VLCDR3 of SEQ ID NO: 24, a VHCDR1 of SEQ ID NO: 6, a VHCDR2 of SEQ ID NO: 30, and a VHCDR3 of SEQ ID NO: 33; or a VLCDR1 of SEQ ID NO: 16, a VLCDR2 of SEQ ID NO: 3, a VLCDR3 of SEQ ID NO: 25, a VHCDR1 of SEQ ID NO: 6, a VHCDR2 of SEQ ID NO: 31, and a VHCDR3 of SEQ ID NO: 34.

Other variants of 2A09 provided herein include variants having:

a VLCDR1 of SEQ ID NO: 2, a VLCDR2 of SEQ ID NO: 3, a VLCDR3 of SEQ ID NO: 23, a VHCDR1 of SEQ ID NO: 6, a VHCDR2 of SEQ ID NO: 29, and a VHCDR3 of SEQ ID NO: 32;

a VLCDR1 of SEQ ID NO: 2, a VLCDR2 of SEQ ID NO: 3, a VLCDR3 of SEQ ID NO: 24, a VHCDR1 of SEQ ID NO: 6, a VHCDR2 of SEQ ID NO: 30, and a VHCDR3 of SEQ ID NO: 33; or a VLCDR1 of SEQ ID NO: 2, a VLCDR2 of SEQ ID NO: 3, a VLCDR3 of SEQ ID NO: 25, a VHCDR1 of SEQ ID NO: 6, a VHCDR2 of SEQ ID NO: 31, and a VHCDR3 of SEQ ID NO: 34.

The various embodiments of the invention are now discussed in more detail.

Antigen Binding Molecules Comprising a VLCDR1 Region

8B06

In one embodiment, an antigen binding molecule, for example an antibody, fragment or variant thereof is provided comprising a light chain variable region comprising an amino acid sequence having at least 70%, 75%, 80%, 85%, 90%, 91%, 92%, 93%, 94%, 95%, 96%, 97%, 98% or 99% identity to the amino acid sequence RETELSRRLHYVR (SEQ ID NO: 16). In one embodiment, an antigen binding molecule, for example an antibody, fragment or variant thereof is provided comprising a light chain variable region comprising an amino acid sequence having at least 90% identity to the amino acid sequence RETELSRRLHYVR (SEQ ID NO: 16).

In one embodiment, an antigen binding molecule, for example an antibody, fragment or variant thereof is provided comprising a light chain variable region comprising the amino acid sequence RETELSRRLHYVR (SEQ ID NO: 16). In a particular embodiment, the antigen binding molecule is an antibody or fragment or variant thereof, wherein the VLCDR1 region of said antibody or fragment or variant thereof is RETELSRRLHYVR (SEQ ID NO: 16).

In some embodiments, an antigen binding molecule derived from the 8B06 antibody, for example an antibody, fragment or variant thereof, is provided which may have a pH 6.0:7.4 EC50 ratio of at least 30.

Amino acid substitutions may be made, for example to reduce or eliminate liabilities in the 8B06 VLCDR1 region.

8D06

In one embodiment, an antigen binding molecule, for example an antibody, fragment or variant thereof is provided comprising a light chain variable region comprising an amino acid sequence having at least 70%, 75%, 80%, 85%, 90%, 91%, 92%, 93%, 94%, 95%, 96%, 97%, 98% or 99% identity to the amino acid sequence VLSPRTHAGHYYR (SEQ ID NO: 12). In one embodiment, an antigen binding molecule, for example an antibody, fragment or variant thereof is provided comprising a light chain variable region comprising an amino acid sequence having at least 90% identity to the amino acid sequence VLSPRTHAGHYYR (SEQ ID NO: 12).

In one embodiment, an antigen binding molecule, for example an antibody, fragment or variant thereof is provided comprising a light chain variable region comprising the amino acid sequence VLSPRTHAGHYYR (SEQ ID NO: 12). In a particular embodiment, the antigen binding molecule is an antibody or fragment or variant thereof, wherein the VLCDR1 region of said antibody or fragment or variant thereof is VLSPRTHAGHYYR (SEQ ID NO: 12).

In some embodiments, an antigen binding molecule derived from the 8D06 antibody, for example an antibody, fragment or variant thereof, is provided which may have a pH 6.0:7.4 EC50 ratio of at least about 5.

Amino acid substitutions may be made, for example to reduce or eliminate liabilities in the 8D06 VLCDR1 region.

8G08

In one embodiment, an antigen binding molecule, for example an antibody, fragment or variant thereof is provided comprising a light chain variable region comprising an amino acid sequence having at least 70%, 75%, 80%, 85%, 90%, 91%, 92%, 93%, 94%, 95%, 96%, 97%, 98% or 99% identity to the amino acid sequence ISNDVPASGHYHR (SEQ ID NO: 10). In one embodiment, an antigen binding molecule, for example an antibody, fragment or variant thereof is provided comprising a light chain variable region comprising an amino acid sequence having at least 90% identity to the amino acid sequence ISNDVPASGHYHR (SEQ ID NO: 10).

In one embodiment, an antigen binding molecule, for example an antibody, fragment or variant thereof is provided comprising a light chain variable region comprising the amino acid sequence ISNDVPASGHYHR (SEQ ID NO: 10). In a particular embodiment, the antigen binding molecule is an antibody or fragment or variant thereof, wherein the VLCDR1 region of said antibody or fragment or variant thereof is ISNDVPASGHYHR (SEQ ID NO: 10).

In some embodiments, an antigen binding molecule derived from the 8G08 antibody, for example an antibody, fragment or variant thereof, is provided which may have a pH 6.0:7.4 EC50 ratio of at least about 5.

Amino acid substitutions may be made, for example to reduce or eliminate liabilities in the 8G08 VLCDR1 region.

8A04

In one embodiment, an antigen binding molecule, for example an antibody, fragment or variant thereof is provided comprising a light chain variable region comprising an amino acid sequence having at least 70%, 75%, 80%, 85%, 90%, 91%, 92%, 93%, 94%, 95%, 96%, 97%, 98% or 99% identity to the amino acid sequence MRTGTGNKGHYTR (SEQ ID NO: 14). In one embodiment, an antigen binding molecule, for example an antibody, fragment or variant thereof is provided comprising a light chain variable region comprising an amino acid sequence having at least 90% identity to the amino acid sequence MRTGTGNKGHYTR (SEQ ID NO: 14).

In one embodiment, an antigen binding molecule, for example an antibody, fragment or variant thereof is provided comprising a light chain variable region comprising the amino acid sequence MRTGTGNKGHYTR (SEQ ID NO: 14). In a particular embodiment, the antigen binding molecule is an antibody or fragment or variant thereof, wherein the VLCDR1 region of said antibody or fragment or variant thereof is MRTGTGNKGHYTR (SEQ ID NO: 14).

In some embodiments, an antigen binding molecule derived from the 8A04 antibody, for example an antibody, fragment or variant thereof is provided which may have a pH 6.0:7.4 EC50 ratio of at least about 30.

Amino acid substitutions may be made, for example to reduce or eliminate liabilities in the 8A04 VLCDR1 region.

For example, in one embodiment, an antigen binding molecule, for example an antibody, fragment or variant thereof is provided comprising a VLCDR1 comprising the amino acid sequence XRTGTGNKGHYTR (SEQ ID NO: 44) wherein X can be any naturally occurring amino acid.

In one embodiment, an antigen binding molecule, for example an antibody, fragment or variant thereof is provided comprising a VLCDR1 comprising the amino acid sequence XRTGTGNKGHYTR (SEQ ID NO: 45) wherein X is selected from the group consisting of Met, Ala or Leu.

In one embodiment, an antigen binding molecule, for example an antibody, fragment or variant thereof is provided comprising a VLCDR1 comprising the amino acid sequence XRTGTGNKGHYTR (SEQ ID NO: 46) wherein X is selected from the group consisting of Ala or Leu.

8D04

In one embodiment, an antigen binding molecule, for example an antibody, fragment or variant thereof is provided comprising a light chain variable region comprising an amino acid sequence having at least 70%, 75%, 80%, 85%, 90%, 91%, 92%, 93%, 94%, 95%, 96%, 97%, 98% or 99% identity to the amino acid sequence RGTGSSFHHKYVR (SEQ ID NO: 18). In one embodiment, an antigen binding molecule, for example an antibody, fragment or variant thereof is provided comprising a light chain variable region comprising an amino acid sequence having at least 90% identity to the amino acid sequence RGTGSSFHHKYVR (SEQ ID NO: 18).

In one embodiment, an antigen binding molecule, for example an antibody, fragment or variant thereof is provided comprising a light chain variable region comprising the amino acid sequence RGTGSSFHHKYVR (SEQ ID NO: 18). In a particular embodiment, the antigen binding molecule is an antibody or fragment or variant thereof, wherein the VLCDR1 region of said antibody or fragment or variant thereof is RGTGSSFHHKYVR (SEQ ID NO: 18).

Amino acid substitutions may be made, for example to reduce or eliminate liabilities in the 8D04 VLCDR1 region.

In some embodiments, an antigen binding molecule derived from the 8D04 antibody, for example an antibody, fragment or variant thereof, is provided which may have a pH 6.0:7.4 EC50 ratio of at least about 5.

2A09_WT

In one embodiment, an antigen binding molecule, for example an antibody, fragment or variant thereof is provided comprising a light chain variable region comprising an amino acid sequence having at least 70%, 75%, 80%, 85%, 90%, 91%, 92%, 93%, 94%, 95%, 96%, 97%, 98% or 99% identity to the amino acid sequence TRSSGSIASNYVQ (SEQ ID NO: 2). In one embodiment, an antigen binding molecule, for example an antibody, fragment or variant thereof is provided comprising a light chain variable region comprising an amino acid sequence having at least 90% identity to the amino acid sequence TRSSGSIASNYVQ (SEQ ID NO: 2).

In one embodiment, an antigen binding molecule, for example an antibody, fragment or variant thereof is provided comprising a light chain variable region comprising the amino acid sequence TRSSGSIASNYVQ (SEQ ID NO: 2). In a particular embodiment, the antigen binding molecule is an antibody or fragment or variant thereof, wherein the VLCDR1 region of said antibody or fragment or variant thereof is TRSSGSIASNYVQ (SEQ ID NO: 2).

Amino acid substitutions may be made, for example to reduce or eliminate liabilities in the 2A09_WT VLCDR1 region.

Heavy and/or Light Chain CDRs

8B06

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYGMY (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence VISYDG-SNKYYADSVKG (SEQ ID NO: 7), a VHCDR3 comprising at least 70%, 75%, 80%, 85%, 90%, 91%, 92%, 93%, 94%, 95%, 96%, 97%, 98% or 99% identity to the amino acid sequence GALTHWGVVIGDGMDV (SEQ ID NO: 8); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence RETELSRRLHYVR (SEQ ID NO: 16), a VLCDR2 comprising at least 70%, 75%, 80%, 85%, 90%, 91%, 92%, 93%, 94%, 95%, 96%, 97%, 98% or 99% identity to the amino add sequence EDDQRPS (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QSFDSTNPWV (SEQ ID NO: 4).

In one embodiment, an antibody, fragment or variant thereof, is provided comprising:

a heavy chain variable region comprising a VHCDR1 comprising at least 90% identity to the amino acid sequence SYGMY (SEQ ID NO: 6), a VHCDR2 comprising at least 90% identity to the amino acid sequence VISYDGSNKYYADSVKG (SEQ ID NO: 7), a VHCDR3 comprising at least 90% Identity to the amino acid sequence GALTHWGVVIGDGMDV (SEQ ID NO: 8); and/or a light chain variable region comprising a VLCDR1 comprising at least 90% identity to amino acid sequence RETELSRRLHYVR (SEQ ID NO: 16), a VLCDR2 comprising at least 90% identity to the amino acid sequence EDDQRPS (SEQ ID NO: 3) and a VLCDR3 comprising at least 90% identity to the amino acid sequence QSFDSTNPWV (SEQ ID NO: 4).

In some embodiments, an antigen binding molecule derived from the 8B06 antibody, for example an antibody, fragment or variant thereof, is provided which may have a pH 6.0:7.4 EC50 ratio of at least about 30.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence RETELSRRLHYVR (SEQ ID NO: 16), a VLCDR2 comprising at the amino acid sequence EDDQRPS (SEQ ID NO: 3) and a VLCDR3 comprising the amino acid sequence QSFDSTNPWV (SEQ ID NO: 4).

Amino acid substitutions may be made, for example to reduce or eliminate liabilities in the 8B06 CDRs.

For example, in one embodiment, an antibody, fragment or variant thereof, is provided comprising:
a heavy chain variable region comprising:
a VHCDR1 comprising the amino acid sequence SYGMY (SEQ ID NO: 6);
a VHCDR2 comprising the amino acid sequence VISYX$_1$GSNKYYAX$_2$SVKG (SEQ ID NO: 29), wherein X$_1$ and X$_2$ can be any naturally occurring amino acid; and
a VHCDR3 comprising the amino acid sequence GALTHWGVVIGXGMDV (SEQ ID NO: 32) wherein X can be any naturally occurring amino acid; and/or
a light chain variable region comprising:
a VLCDR1 comprising the amino acid sequence RETELSRRLHYVR (SEQ ID NO: 16);
a VLCDR2 comprising at the amino acid sequence EDDQRPS (SEQ ID NO: 3); and
a VLCDR3 comprising the amino acid sequence QSFXSTNPWV (SEQ ID NO: 23), wherein X can be any naturally occurring amino acid.

In one embodiment, an antibody, fragment or variant thereof, is provided comprising:
a heavy chain variable region comprising:
a VHCDR1 comprising the amino acid sequence SYGMY (SEQ ID NO: 6);
a VHCDR2 comprising the amino acid sequence VISYX$_1$GSNKYYAX$_2$SVKG (SEQ ID NO: 30), wherein X$_1$ and X$_2$ are each independently selected from the group consisting of Asp, Gin, Glu and Ala; and
a VHCDR3 comprising the amino acid sequence GALTHWGVVIGXGMDV (SEQ ID NO: 33) wherein X is selected from the group consisting of Asp, Gin, Glu and Ala; and/or
a light chain variable region comprising:
a VLCDR1 comprising the amino acid sequence RETELSRRLHYVR (SEQ ID NO: 16);
a VLCDR2 comprising at the amino acid sequence EDDQRPS (SEQ ID NO: 3); and
a VLCDR3 comprising the amino acid sequence QSFXSTNPWV (SEQ ID NO: 24), wherein X is selected from the group consisting of Asp, Gln, Glu and Ala.

In one embodiment, an antibody, fragment or variant thereof, is provided comprising:
a heavy chain variable region comprising:
a VHCDR1 comprising the amino acid sequence SYGMY (SEQ ID NO: 6);
a VHCDR2 comprising the amino acid sequence VISYX$_1$GSNKYYAX$_2$SVKG (SEQ ID NO: 31), wherein X$_1$ and X$_2$ are each independently selected from the group consisting of Gln, Glu and Ala; and
a VHCDR3 comprising the amino acid sequence GALTHWGVVIGXGMDV (SEQ ID NO: 34) wherein X is selected from the group consisting of Gln, Glu and Ala; and/or
a light chain variable region comprising:
a VLCDR1 comprising the amino acid sequence RETELSRRLHYVR (SEQ ID NO: 16);
a VLCDR2 comprising at the amino acid sequence EDDQRPS (SEQ ID NO: 3); and a VLCDR3 comprising the amino acid sequence QSFXSTNPWV (SEQ ID NO: 25), wherein X is selected from the group consisting of Gln, Glu and Ala.

In one embodiment, an antibody, fragment or variant thereof, is provided comprising:
a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or
a light chain variable region comprising a VLCDR1 comprising the amino acid sequence RETELSRRLHYVR (SEQ ID NO: 16), a VLCDR2 comprising at the amino acid sequence EDDQRPS (SEQ ID NO: 3) and a VLCDR3 comprising the amino acid sequence QSFDSTNPWV (SEQ ID NO: 4);
optionally wherein the Met residues are each independently substituted with an amino acid selected from the group consisting of Ala and Leu, and the Asp residues are each independently substituted with an amino acid selected from the group consisting of Ala, Gln and Glu.

8D06

In one embodiment, an antibody, fragment or variant thereof, is provided comprising:
a heavy chain variable region comprising a VHCDR1 comprising at least 70%, 75%, 80%, 85%, 90%, 91%, 92%, 93%, 94%, 95%, 96%, 97%, 98% or 99% Identity to the amino acid sequence SYGMY (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence VISYDGSNKYYADSVKG (SEQ ID NO: 7), a VHCDR3 comprising at least 70%, 75%, 80%, 85%, 90%, 91%, 92%, 93%, 94%, 95%, 96%, 97%, 98% or 99% identity to the amino acid sequence GALTHWGVVIGDGMDV (SEQ ID NO: 8); and/or
a light chain variable region comprising a VLCDR1 comprising the at least 70%, 75%, 80%, 85%, 90%, 91%, 92%, 93%, 94%, 95%, 96%, 97%, 98% or 99% identity to amino acid sequence VLSPRTHAGHYYR (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence EDDQRPS (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QSFDSTNPWV (SEQ ID NO: 4).

In one embodiment, an antibody, fragment or variant thereof, is provided comprising:
a heavy chain variable region comprising a VHCDR1 comprising at least 90% identity to the amino acid sequence SYGMY (SEQ ID NO: 6), a VHCDR2 comprising at least 90% identity to the amino acid sequence VISYDGSNKYYADSVKG (SEQ ID NO: 7), a VHCDR3 comprising at least 90% identity to the amino acid sequence GALTHWGVVIGDGMDV (SEQ ID NO: 8); and/or
a light chain variable region comprising a VLCDR1 comprising at least 90% identity to amino acid sequence VLSPRTHAGHYYR (SEQ ID NO: 12), a VLCDR2 comprising at least 90% identity to the amino acid sequence EDDQRPS (SEQ ID NO: 3) and a VLCDR3 comprising at least 90% identity to the amino acid sequence QSFDSTNPWV (SEQ ID NO: 4).

In some embodiments, an antigen binding molecule derived from the 8D06 antibody, for example an antibody, fragment or variant thereof, is provided which may have a pH 6.0:7.4 EC50 ratio of at least about 5.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence VLSPRTHAGHYYR (SEQ ID NO: 12), a VLCDR2 comprising at the amino acid sequence EDDQRPS (SEQ ID NO: 3) and a VLCDR3 comprising the amino acid sequence QSFDSTNPWV (SEQ ID NO: 4).

Amino acid substitutions may be made, for example to reduce or eliminate liabilities in the 8D06 CDRs.

For example, in one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 29), wherein X$_1$ and X$_2$ can be any naturally occurring amino acid; and a VHCDR3 comprising the amino acid sequence GALTHWGVVIGXGMDV (SEQ ID NO: 32) wherein X can be any naturally occurring amino acid; and/or a light chain variable region comprising:

a VLCDR1 comprising the amino acid sequence VLSPRTHAGHYYR (SEQ ID NO: 12);

a VLCDR2 comprising at the amino acid sequence EDDQRPS (SEQ ID NO: 3); and a VLCDR3 comprising the amino acid sequence QSFXSTNPWV (SEQ ID NO: 23), wherein X can be any naturally occurring amino acid In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 30), wherein X$_1$ and X$_2$ are each independently selected from the group consisting of Asp, Gin, Glu and Ala; and a VHCDR3 comprising the amino acid sequence GALTHWGVVIGXGMDV (SEQ ID NO: 33) wherein X is selected from the group consisting of Asp, Gin, Glu and Ala; and/or a light chain variable region comprising:

a VLCDR1 comprising the amino acid sequence VLSPRTHAGHYYR (SEQ ID NO: 12);

a VLCDR2 comprising at the amino acid sequence EDDQRPS (SEQ ID NO: 3); and a VLCDR3 comprising the amino acid sequence QSFXSTNPWV (SEQ ID NO: 24), wherein X is selected from the group consisting of Asp, Gin, Glu and Ala.

In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_2$GSNKYYAX$_2$SVKG (SEQ ID NO: 31), wherein X$_1$ and X$_2$ are each independently selected from the group consisting of Gln, Glu and Ala; and a VHCDR3 comprising the amino acid sequence GALTHWGVVIGXGMDV (SEQ ID NO: 34) wherein X is selected from the group consisting of Gln, Glu and Ala; and/or a light chain variable region comprising:

a VLCDR1 comprising the amino acid sequence VLSPRTHAGHYYR (SEQ ID NO: 12);

a VLCDR2 comprising at the amino acid sequence EDDQRPS (SEQ ID NO: 3); and a VLCDR3 comprising the amino acid sequence QSFXSTNPWV (SEQ ID NO: 25), wherein X is selected from the group consisting of Gin, Glu and Ala.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence VLSPRTHAGHYYR (SEQ ID NO: 12), a VLCDR2 comprising at the amino acid sequence EDDQRPS (SEQ ID NO: 3) and a VLCDR3 comprising the amino acid sequence QSFDSTNPWV (SEQ ID NO: 4). optionally wherein the Met residues are each independently substituted with an amino acid selected from the group consisting of Ala and Leu, and the Asp residues are each independently substituted with an amino acid selected from the group consisting of Ala, Gin and Glu.

8G08

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYGMY (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence VISYDG-SNKYYADSVKG (SEQ ID NO: 7), a VHCDR3 comprising at least 70%, 75%, 80%, 85%, 90%, 91%, 92%, 93%, 94%, 95%, 96%, 97%, 98% or 99% identity to the amino acid sequence GALTHWGVVIGDGMDV (SEQ ID NO: 8); and/or a light chain variable region comprising a VLCDR1 comprising the at least 70%, 75%, 80%, 85%, 90%, 91%, 92%, 93%, 94%, 95%, 96%, 97%, 98% or 99% Identity to amino acid sequence ISNDVPASGHYHR (SEQ ID NO: 10), a VLCDR2 comprising at least 70%, 75%, 80%, 85%, 90%, 91%, 92%, 93%, 94%, 95%, 96%, 97%, 98% or 99% identity to the amino acid sequence EDDQRPS (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QSFDSTNPWV (SEQ ID NO: 4).

In one embodiment, an antibody, fragment or variant thereof, is provided comprising:

a heavy chain variable region comprising a VHCDR1 comprising at least 90% identity to the amino acid sequence SYGMY (SEQ ID NO: 6), a VHCDR2 comprising at least 90% identity to the amino acid sequence VISYDGSNKYYADSVKG (SEQ ID NO: 7), a VHCDR3 comprising at least 90% identity to the amino acid sequence GALTHWGVVIGDGMDV (SEQ ID NO: 8); and/or a light chain variable region comprising a VLCDR1 comprising at least 90% identity to amino acid sequence ISNDVPASGHYHR (SEQ ID NO: 10), a VLCDR2 comprising at least 90% identity to the amino acid sequence EDDQRPS (SEQ ID NO: 3) and a VLCDR3 comprising at least 90% identity to the amino acid sequence QSFDSTNPWV (SEQ ID NO: 4).

In some embodiments, an antigen binding molecule derived from the 8G08 antibody, for example an antibody, fragment or variant thereof, is provided which may have a pH 6.0:7.4 EC50 ratio of at least about 5.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence ISNDVPASGHYHR (SEQ ID NO: 10), a VLCDR2 comprising at the amino acid sequence EDDQRPS (SEQ ID NO: 3) and a VLCDR3 comprising the amino acid sequence QSFDSTNPWV (SEQ ID NO: 4).

Amino acid substitutions may be made to reduce or eliminate liabilities in the 8G08 CDRs.

For example, in one embodiment, an antibody, fragment or variant thereof, is provided comprising:

a heavy chain variable region comprising:
a VHCDR1 comprising the amino acid sequence SYGMY (SEQ ID NO: 6);
a VHCDR2 comprising the amino acid sequence VISYX$_1$GSNKYYAX$_2$SVKG (SEQ ID NO: 29), wherein X$_1$ and X$_2$ can be any naturally occurring amino acid; and a VHCDR3 comprising the amino acid sequence GALTHWGVVIGXGMDV (SEQ ID NO: 32) wherein X can be any naturally occurring amino acid; and/or a light chain variable region comprising:
a VLCDR1 comprising the amino acid sequence ISNDVPASGHYHR (SEQ ID NO: 10);
a VLCDR2 comprising at the amino acid sequence EDDQRPS (SEQ ID NO: 3); and
a VLCDR3 comprising the amino acid sequence QSFXSTNPWV (SEQ ID NO: 23), wherein X can be any naturally occurring amino acid In one embodiment, an antibody, fragment or variant thereof, is provided comprising:

a heavy chain variable region comprising:
a VHCDR1 comprising the amino acid sequence SYGMY (SEQ ID NO: 6);
a VHCDR2 comprising the amino acid sequence VISYX$_1$GSNKYYAX$_2$SVKG (SEQ ID NO: 30), wherein X$_1$ and X$_2$ are each independently selected from the group consisting of Asp, Gln, Glu and Ala; and a VHCDR3 comprising the amino acid sequence GALTHWGVVIGXGMDV (SEQ ID NO: 33) wherein X is selected from the group consisting of Asp, Gln, Glu and Ala; and/or a light chain variable region comprising:
a VLCDR1 comprising the amino acid sequence ISNDVPASGHYHR (SEQ ID NO: 10);
a VLCDR2 comprising at the amino acid sequence EDDQRPS (SEQ ID NO: 3); and
a VLCDR3 comprising the amino acid sequence QSFXSTNPWV (SEQ ID NO: 24), wherein X is selected from the group consisting of Asp, Gin, Glu and Ala.

In one embodiment, an antibody, fragment or variant thereof, is provided comprising:

a heavy chain variable region comprising:
a VHCDR1 comprising the amino acid sequence SYGMY (SEQ ID NO: 6);
a VHCDR2 comprising the amino acid sequence VISYX$_1$GSNKYYAX$_2$SVKG (SEQ ID NO: 31), wherein X$_1$ and X$_2$ are each independently selected from the group consisting of Gln, Glu and Ala; and
a VHCDR3 comprising the amino acid sequence GALTHWGVVIGXGMDV (SEQ ID NO: 34) wherein X is selected from the group consisting of Gln, Glu and Ala; and/or a light chain variable region comprising:
a VLCDR1 comprising the amino acid sequence ISNDVPASGHYHR (SEQ ID NO: 10);
a VLCDR2 comprising at the amino acid sequence EDOQRPS (SEQ ID NO: 3); and
a VLCDR3 comprising the amino acid sequence QSFXSTNPWV (SEQ ID NO: 25), wherein X is selected from the group consisting of Gln, Glu and Ala.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence ISNDVPASGHYHR (SEQ ID NO: 10), a VLCDR2 comprising at the amino acid sequence EDDQRPS (SEQ ID NO: 3) and a VLCDR3 comprising the amino acid sequence QSFDSTNPWV (SEQ ID NO: 4);

optionally wherein the Met residues are each independently substituted with an amino acid selected from the group consisting of Ala and Leu, and the Asp residues are each independently substituted with an amino acid selected from the group consisting of Ala, Gin and Glu.

8A04

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYGMY (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence VISYDG- SNKYYADSVKG (SEQ ID NO: 7), a VHCDR3 comprising at least 70%, 75%, 80%, 85%, 90%, 91%, 92%, 93%, 94%, 95%, 96%, 97%, 98% or 99% identity to the amino acid sequence GALTHWGVVIGDGMDV (SEQ ID NO: 8); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence MRTGTGNKGHYTR (SEQ ID NO: 14), a VLCDR2 comprising at least 70%, 75%, 80%, 85%, 90%, 91%, 92%, 93%, 94%, 95%, 96%, 97%, 98% or 99% Identity to the amino add sequence EDDQRPS (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QSFDSTNPWV (SEQ ID NO: 4).

In one embodiment, an antibody, fragment or variant thereof, is provided comprising:

a heavy chain variable region comprising a VHCDR1 comprising at least 90% Identity to the amino acid sequence SYGMY (SEQ ID NO: 6), a VHCDR2 comprising at least 90% identity to the amino acid sequence VISYDGSNKYYADSVKG (SEQ ID NO: 7), a VHCDR3 comprising at least 90% Identity to the amino acid sequence GALTHWGVVIGDGMDV (SEQ ID NO: 8); and/or a light chain variable region comprising a VLCDR1 comprising at least 90% identity to amino acid sequence MRTGTGNKGHYTR (SEQ ID NO: 14), a VLCDR2 comprising at least 90% identity to the amino acid sequence EDDQRPS (SEQ ID NO: 3) and a VLCDR3 comprising at least 90% identity to the amino acid sequence QSFDSTNPWV (SEQ ID NO: 4).

In some embodiments, an antigen binding molecule derived from the 8A04 antibody, for example an antibody, fragment or variant thereof is provided which may have a pH 6.0:7.4 EC50 ratio of at least about 30.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence MRTGTGNKGHYTR (SEQ ID NO: 14), a VLCDR2 comprising at the amino acid sequence EDDQRPS (SEQ ID NO: 3) and a VLCDR3 comprising the amino acid sequence QSFDSTNPWV (SEQ ID NO: 4).

Amino acid substitutions may be made, for example to reduce or eliminate liabilities in the 8A04 CDRs.

For example, in one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 29), wherein X$_1$ and X$_2$ can be any naturally occurring amino acid; and a VHCDR3 comprising the amino acid sequence GALTHWGVVIGXGMDV (SEQ ID NO: 32) wherein X can be any naturally occurring amino acid; and/or a light chain variable region comprising:

a VLCDR1 comprising the amino acid sequence XRTGTGNKGHYTR (SEQ ID NO: 44), wherein X can be any naturally occurring amino acid;

a VLCDR2 comprising at the amino acid sequence EDDQRPS (SEQ ID NO: 3); and a VLCDR3 comprising the amino acid sequence QSFXSTNPWV (SEQ ID NO: 23), wherein X can be any naturally occurring amino acid In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 30), wherein X$_1$ and X$_2$ are each independently selected from the group consisting of Asp, Gln, Glu and Ala; and a VHCDR3 comprising the amino acid sequence GALTHWGVVIGXGMDV (SEQ ID NO: 33) wherein X is selected from the group consisting of Asp, Gln, Glu and Ala; and/or a light chain variable region comprising:

a VLCDR1 comprising the amino acid sequence XRTGTGNKGHYTR (SEQ ID NO: 45), wherein X is selected from the group consisting of Met, Ala or Leu;

a VLCDR2 comprising the amino acid sequence EDDQRPS (SEQ ID NO: 3); and a VLCDR3 comprising the amino acid sequence QSFXSTNPWV (SEQ ID NO: 24), wherein X is selected from the group consisting of Asp, Gin, Glu and Ala.

In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 31), wherein X$_1$ and X$_2$ are each independently selected from the group consisting of Gin, Glu and Ala; and a VHCDR3 comprising the amino acid sequence GALTHWGVVIGXGMDV (SEQ ID NO: 34) wherein X is selected from the group consisting of Gin, Glu and Ala; and/or a light chain variable region comprising:

a VLCDR1 comprising the amino acid sequence XRTGTGNKGHYTR (SEQ ID NO: 46), wherein X is selected from the group consisting of Ala or Leu;

a VLCDR2 comprising at the amino acid sequence EDDQRPS (SEQ ID NO: 3); and a VLCDR3 comprising the amino acid sequence QSFXSTNPWV (SEQ ID NO: 25), wherein X is selected from the group consisting of Gln, Glu and Ala.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence MRTGTGNKGHYTR (SEQ ID NO: 14), a VLCDR2 comprising at the amino acid sequence EDDQRPS (SEQ ID NO: 3) and a VLCDR3 comprising the amino acid sequence QSFDSTNPWV (SEQ ID NO: 4);

optionally wherein the Met residues are each independently substituted with an amino acid selected from the group consisting of Ala and Leu, and the Asp residues are each independently substituted with an amino acid selected from the group consisting of Ala, Gln and Glu.

8D04

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYGMY (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence VISYDGSNKYYADSVKG (SEQ ID NO: 7), a VHCDR3 comprising at least 70%, 75%, 80%, 85%, 90%, 91%, 92%, 93%, 94%, 95%, 96%, 97%, 98% or 99% identity to the amino acid sequence GALTHWGVVIGDGMDV (SEQ ID NO: 8); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence RGTGSSFHHKYVR (SEQ ID NO: 18), a VLCDR2 comprising at least 70%, 75%, 80%, 85%, 90%, 91%, 92%, 93%, 94%, 95%, 96%, 97%, 98% or 99% identity to the amino acid sequence EDDQRPS (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QSFDSTNPWV (SEQ ID NO: 4).

In one embodiment, an antibody, fragment or variant thereof, is provided comprising:

a heavy chain variable region comprising a VHCDR1 comprising at least 90% identity to the amino acid sequence SYGMY (SEQ ID NO: 6), a VHCDR2 comprising at least 90% identity to the amino acid sequence VISYDGSNKYYADSVKG (SEQ ID NO: 7), a VHCDR3 comprising at least 90% identity to the amino acid sequence GALTHWGVVIGDGMDV (SEQ ID NO: 8); and/or a light chain variable region comprising a VLCDR1 comprising at least 90% identity to amino acid sequence RGTGSSFHHKYVR (SEQ ID NO: 18), a VLCDR2 comprising at least 90% identity to the amino acid sequence EDDQRPS (SEQ ID NO: 3) and a VLCDR3 comprising at least 90% identity to the amino acid sequence QSFDSTNPWV (SEQ ID NO: 4).

In some embodiments, an antigen binding molecule derived from the 8D04 antibody, for example an antibody, fragment or variant thereof, is provided which may have a pH 6.0:7.4 EC50 ratio of at least about 5.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence RGTGSSFHHKYVR (SEQ ID NO: 18), a VLCDR2 comprising at the amino acid sequence EDDQRPS (SEQ ID NO: 3) and a VLCDR3 comprising the amino acid sequence QSFDSTNPWV (SEQ ID NO: 4).

Amino acid substitutions may be made, for example to reduce or eliminate liabilities in the 8D04 CDRs.

For example, in one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 29), wherein X$_1$ and X$_2$ can be any naturally occurring amino acid; and a VHCDR3 comprising the amino acid sequence GALTHWGVVIGXGMDV (SEQ ID NO: 32) wherein X can be any naturally occurring amino acid; and/or a light chain variable region comprising:

a VLCDR1 comprising the amino acid sequence RGTGSSFHHKYVR (SEQ ID NO: 18);

a VLCDR2 comprising at the amino acid sequence EDDQRPS (SEQ ID NO: 3); and a VLCDR3 comprising the amino acid sequence QSFXSTNPWV (SEQ ID NO: 24), wherein X can be any naturally occurring amino acid.

In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 30), wherein X$_1$ and X$_2$ are each independently selected from the group consisting of Asp, Gln, Glu and Ala; and a VHCDR3 comprising the amino acid sequence GALTHWGVVIGXGMDV (SEQ ID NO: 33) wherein X is selected from the group consisting of Asp, Gin, Glu and Ala; and/or a light chain variable region comprising:

a VLCDR1 comprising the amino acid sequence RGTGSSFHHKYVR (SEQ ID NO: 18);

a VLCDR2 comprising at the amino acid sequence EDDQRPS (SEQ ID NO: 3); and a VLCDR3 comprising the amino acid sequence QSFXSTNPWV (SEQ ID NO: 25), wherein X is selected from the group consisting of Asp, Gin, Glu and Ala.

In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 31), wherein X$_1$ and X$_2$ are each independently selected from the group consisting of Gin, Glu and Ala; and a VHCDR3 comprising the amino acid sequence GALTHWGVVIGXGMDV (SEQ ID NO: 34) wherein X is selected from the group consisting of Gin, Glu and Ala; and/or a light chain variable region comprising:

a VLCDR1 comprising the amino acid sequence RGTGSSFHHKYVR (SEQ ID NO: 18);

a VLCDR2 comprising at the amino acid sequence EDDQRPS (SEQ ID NO: 3); and a VLCDR3 comprising the amino acid sequence QSFXSTNPWV (SEQ ID NO: 26), wherein X is selected from the group consisting of Gln, Glu and Ala.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence RGTGSSFHHKYVR (SEQ ID NO: 18), a VLCDR2 comprising at the amino acid sequence EDDQRPS (SEQ ID NO: 3) and a VLCDR3 comprising the amino acid sequence QSFDSTNPWV (SEQ ID NO: 4);

optionally wherein the Met residues are each independently substituted with an amino acid selected from the group consisting of Ala and Leu, and the Asp residues are each independently substituted with an amino acid selected from the group consisting of Ala, Gln and Glu.

2A09_WT

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYGMY (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence VISYDG-SNKYYADSVKG (SEQ ID NO: 7), a VHCDR3 comprising at least 70%, 75%, 80%, 85%, 90%, 91%, 92%, 93%, 94%, 95%, 96%, 97%, 98% or 99% identity to the amino acid sequence GALTHWGVVIGDGMDV (SEQ ID NO: 8); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence TRSSGSIASNYVQ (SEQ ID NO: 2), a VLCDR2 comprising at least 70%, 75%, 80%, 85%, 90%, 91%, 92%, 93%, 94%, 95%, 96%, 97%, 98% or 99% identity to the amino acid sequence EDDQRPS (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QSFDSTNPWV (SEQ ID NO: 4).

In one embodiment, an antibody, fragment or variant thereof, is provided comprising:

a heavy chain variable region comprising a VHCDR1 comprising at least 90% identity to the amino acid sequence SYGMY (SEQ ID NO: 6), a VHCDR2 comprising at least 90% identity to the amino acid sequence VISYDGSNKYYADSVKG (SEQ ID NO: 7), a VHCDR3 comprising at least 90% identity to the amino acid sequence GALTHWGVVIGDGMDV (SEQ ID NO: 8); and/or a light chain variable region comprising a VLCDR1 comprising at least 90% identity to amino acid sequence TRSSGSIASNYVQ (SEQ ID NO: 2), a VLCDR2 comprising at least 90% identity to the amino acid sequence EDDQRPS (SEQ ID NO: 3) and a VLCDR3 comprising at least 90% identity to the amino acid sequence QSFDSTNPWV (SEQ ID NO: 4).

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence TRSSG-SIASNYVQ (SEQ ID NO: 2), a VLCDR2 comprising at the amino acid sequence EDDQRPS (SEQ ID NO: 3) and a VLCDR3 comprising the amino acid sequence QSFDSTNPWV (SEQ ID NO: 4).

Amino acid substitutions may be made, for example, to reduce or eliminate liabilities in the 2A09_WT CDRs.

For example, in one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 29), wherein X$_1$ and X$_2$ can be any naturally occurring amino acid; and a VHCDR3 comprising the amino acid sequence GALTHWGVVIGXGMDV (SEQ ID NO: 32) wherein X can be any naturally occurring amino acid; and/or a light chain variable region comprising:

a VLCDR1 comprising the amino acid sequence TRSSGSIASNYVQ (SEQ ID NO: 2);

a VLCDR2 comprising at the amino acid sequence EDDQRPS (SEQ ID NO: 3); and a VLCDR3 comprising the amino acid sequence QSFXSTNPWV (SEQ ID NO: 23), wherein X can be any naturally occurring amino acid.

In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX$_1$GSNKYYAX$_2$SVKG (SEQ ID NO: 30), wherein X$_1$ and X$_2$ are each independently selected from the group consisting of Asp, Gln, Glu and Ala; and a VHCDR3 comprising the amino acid sequence GALTHWGVVIGXGMDV (SEQ ID NO: 33) wherein X is selected from the group consisting of Asp, Gln, Glu and Ala; and/or a light chain variable region comprising:

a VLCDR1 comprising the amino acid sequence TRSSGSIASNYVQ (SEQ ID NO: 2);

a VLCDR2 comprising at the amino acid sequence EDDQRPS (SEQ ID NO: 3); and a VLCDR3 comprising the amino acid sequence QSFXSTNPWV (SEQ ID NO:24), wherein X is selected from the group consisting of Asp, Gln, Glu and Ala.

In one embodiment, an antibody, fragment or variant thereof, is provided comprising:

a heavy chain variable region comprising:

a VHCDR1 comprising the amino acid sequence SYGMY (SEQ ID NO: 6);

a VHCDR2 comprising the amino acid sequence VISYX₁GSNKYYAX₂SVKG (SEQ ID NO: 31), wherein $X_1$ and $X_2$ are each independently selected from the group consisting of Gln, Glu and Ala; and a VHCDR3 comprising the amino acid sequence GALTHWGVVIGXGMDV (SEQ ID NO: 34) wherein X is selected from the group consisting of Gln, Glu and Ala; and/or a light chain variable region comprising:

a VLCDR1 comprising the amino acid sequence TRSSGSIASNYVQ (SEQ ID NO: 2);

a VLCDR2 comprising at the amino acid sequence EDDQRPS (SEQ ID NO: 3); and a VLCDR3 comprising the amino acid sequence QSFXSTNPWV (SEQ ID NO: 25), wherein X is selected from the group consisting of Gln, Glu and Ala.

In one embodiment, an antibody, fragment or variant thereof, is provided comprising:

a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and/or a light chain variable region comprising a VLCDR1 comprising the amino acid sequence TRSSG-SIASNYVQ (SEQ ID NO: 2), a VLCDR2 comprising at the amino acid sequence EDDQRPS (SEQ ID NO: 3) and a VLCDR3 comprising the amino acid sequence QSFDSTNPWV (SEQ ID NO: 4);

optionally wherein the Met residues are each independently substituted with an amino acid selected from the group consisting of Ala and Leu, and the Asp residues are each independently substituted with an amino acid selected from the group consisting of Ala, Gln and Glu.

Heavy and/or Light Chain Variable Regions

In one embodiment, the invention provides an antigen-binding molecule, in particular an antibody that binds to PD-L1, comprising a heavy chain variable region having at least 70%, 75%, 80%, 85%, 90%, 91%, 92%, 93%, 94%, 95%, 96%, 97%, 98% or 99% identity to the amino acid sequence SEQ ID NO: 5, and/or a light chain variable region having at least 70%, 75%, 80%, 85%, 90%, 91%, 92%, 93%, 94%, 95%, 96%, 97%, 98% or 99% identity to the amino acid sequence selected from the group consisting of SEQ ID NO: 15, SEQ ID NO: 11, SEQ ID NO: 9, SEQ ID NO: 13, SEQ ID NO: 17, SEQ ID NO: 1.

In such embodiments, an antigen binding molecule, for example an antibody, fragment or variant thereof is provided which has a pH 6.0:7.4 EC50 ratio of at least about 5.

In one embodiment, the antibody binds to PD-L1 and comprises a heavy chain variable region having the amino acid sequence SEQ ID NO: 5, and/or a light chain variable region having the amino acid sequence selected from the group consisting of SEQ ID NO: 15, SEQ ID NO: 11, SEQ ID NO: 9, SEQ ID NO: 13, SEQ ID NO: 17, SEQ ID NO: 1.

In one embodiment, an antigen-binding molecule, for example an antibody, variant or fragment thereof is provided, wherein the antigen-binding molecule comprises a heavy chain variable region and a light chain variable region selected from the group consisting of:

a) a VH comprising the amino acid sequence of SEQ ID NO: 5 and a VL comprising the amino acid sequence of SEQ ID NO: 15 (or comprising VH and VL sequences that are at least 90% identical to SEQ ID NO: 5 and SEQ ID NO: 15, respectively);

b) a VH comprising the amino acid sequence of SEQ ID NO: 5 and a VL comprising the amino acid sequence of SEQ ID NO: 11 (or comprising VH and VL sequences that are at least 90% identical to SEQ ID NO: 5 and SEQ ID NO: 11, respectively);

c) a VH comprising the amino acid sequence of SEQ ID NO: 5 and a VL comprising the amino acid sequence of SEQ ID NO: 9 (or comprising VH and VL sequences that are at least 90% identical to SEQ ID NO: 5 and SEQ ID NO: 9, respectively);

d) a VH comprising the amino acid sequence of SEQ ID NO: 5 and a VL comprising the amino acid sequence of SEQ ID NO: 13 (or comprising VH and VL sequences that are at least 90% identical to SEQ ID NO: 5 and SEQ ID NO: 13, respectively);

e) a VH comprising the amino acid sequence of SEQ ID NO: 5 and a VL comprising the amino acid sequence of SEQ ID NO: 17 (or comprising VH and VL sequences that are at least 90% identical to SEQ ID NO: 5 and SEQ ID NO: 17, respectively).

f) a VH comprising the amino acid sequence of SEQ ID NO: 5 and a VL comprising the amino acid sequence of SEQ ID NO: 1 (or comprising VH and VL sequences that are at least 90% identical to SEQ ID NO: 5 and SEQ ID NO: 1, respectively).

In one embodiment, an antigen-binding molecule, for example an antibody, variant or fragment thereof is provided, wherein the antigen-binding molecule comprises a heavy chain variable region and a light chain variable region selected from the group consisting of:

a) a VH comprising the amino acid sequence SEQ ID NO: 5 or a VH having up to 5 amino acid substitutions compared to the VH sequence of SEQ ID NO: 5 (or a variant thereof, such as an affinity matured variant thereof); and/or a VL comprising the amino acid sequence SEQ ID NO: 15 or a VL sequence having up to 5 amino acid substitutions compared to the VL of SEQ ID NO: 15 (or a variant thereof, such as an affinity matured variant thereof).

b) a VH comprising the amino acid sequence SEQ ID NO: 5 or a VH having up to 5 amino acid substitutions compared to the VH sequence of SEQ ID NO: 5 (or a variant thereof, such as an affinity matured variant thereof); and/or a VL comprising the amino acid sequence SEQ ID NO: 11 or a VL sequence having up to 5 amino acid substitutions compared to the VL of SEQ ID NO: 11 (or a variant thereof, such as an affinity matured variant thereof).

c) a VH comprising the amino acid sequence SEQ ID NO: 5 or a VH having up to 5 amino acid substitutions compared to the VH sequence of SEQ ID NO: 5 (or a variant thereof, such as an affinity matured variant thereof); and/or a VL comprising the amino acid sequence SEQ ID NO: 9 or a VL sequence having up to 5 amino acid substitutions compared to the VL of SEQ ID NO: 9 (or a variant thereof, such as an affinity matured variant thereof).

d) a VH comprising the amino acid sequence SEQ ID NO: 5 or a VH having up to 5 amino acid substitutions compared to the VH sequence of SEQ ID NO: 5 (or a variant thereof, such as an affinity matured variant thereof); and/or a VL comprising the amino acid sequence SEQ ID NO: 13 or a VL sequence having up to 5 amino acid substitutions compared to the VL of SEQ ID NO: 13 (or a variant thereof, such as an affinity matured variant thereof).

e) a VH comprising the amino acid sequence SEQ ID NO: 5 or a VH having up to 5 amino acid substitutions compared to the VH sequence of SEQ ID NO: 5 (or a variant thereof, such as an affinity matured variant thereof); and/or a VL comprising the amino acid sequence SEQ ID NO: 17 or a VL sequence having up to 5 amino acid substitutions compared to the VL of SEQ ID NO: 17 (or a variant thereof, such as an affinity matured variant thereof).

f) a VH comprising the amino acid sequence SEQ ID NO: 5 or a VH having up to 5 amino acid substitutions compared to the VH sequence of SEQ ID NO: 5 (or a variant thereof, such as an affinity matured variant thereof); and/or a VL comprising the amino acid sequence SEQ ID NO: 1 or a VL sequence having up to 5 amino acid substitutions compared to the VL of SEQ ID NO: 1 (or a variant thereof, such as an affinity matured variant thereof).

In some embodiments, the amino acid substitutions all occur in the CDRs of the variable regions. In some embodiments, all the amino acid substitutions occur in the framework regions of the variable regions.

In some embodiments, the amino acid substitutions may be conservative amino acid substitutions. In some embodiments, the amino acid substitutions may be to address one or more potential liabilities in the sequences. Some variant antibodies may have one or more amino acid substitutions to address one or more liabilities and may comprise one or more further amino acid substitutions that are conservative amino acid substitutions.

In one embodiment, an antigen binding molecule, for example an antibody, fragment or variant thereof is provided which has a pH 6.0:7.4 EC50 ratio of at least 5.

Variants therefore are also provided, as discussed above, including humanised and affinity matured variants thereof, and variants having smaller or greater % identities or homologies, for example at least 70%, 75%, 80%, 85%, 90%, 91%, 92%, 93%, 94%, 95%, 96%, 97%, 98% or 99% identity or homology to the specified sequence(s). Variants having one or more amino acid substitutions are also provided.

In one embodiment of the invention, there is provided an anti-PD-L1 antigen binding molecule comprising a heavy chain variable region comprising the amino acid sequence of SEQ ID NO: 5 and a light chain variable region that is at least 89% identical to SEQ ID NO: 1. Such antigen-binding molecules may retain the functional activity (for example preferential pH binding, EC50, IC50 and/or Kd) of the antigen-binding molecule from which the variant antigen-binding molecule is derived.

In some embodiments, the % sequence identity is calculated without the sequence of all 6 CDRs of the specified heavy or light chain variable region. In such embodiments, the variations in sequence occur only in the framework regions. For example, the anti-PDL1 antigen binding molecule may comprise a variable heavy chain region having at least 95% identity to the variable heavy chain region of SEQ ID NO: 5, and/or a variable light chain region having at least 95% identity to the variable light chain region of SEQ ID NOs: 15, 11, 9, 13, 17 or 1, wherein any amino acid variations occur only in the framework regions of the variable heavy and light chain sequences. In such embodiments, the anti-PD-L1 antigen binding molecules having the specified sequence identities comprise the complete heavy chain CDR1, CDR2 and CDR3 sequences of SEQ ID NO: 5, and the complete light chain CDR1, CDR2 and CDR3 sequences of SEQ ID NOs: 15, 11, 9, 13, 17 or 1 (i.e. the complete heavy and light chain CDR sequences of the antibodies from which the variants are derived).

As noted above, amino acid substitutions may be made to reduce or eliminate liabilities in the heavy chain variable regions and/or light chain variable regions of the antigen-binding molecules of the invention. Such substitutions to reduce or eliminate liabilities may occur in the CDRs. Such substitutions to reduce or eliminate liabilities may occur in framework regions of the variable regions.

For example, in one embodiment, there is provided an antigen binding molecule (for example an antibody or antigen-binding fragment thereof) that binds to PD-L1 and comprises a heavy chain variable region having the amino acid sequence:

(SEQ ID NO: 26)

QVQLVQSGGGVVQPGRSLRLSCAASGFTFSSYGMYWVRQAPGKGLEWVAV

ISYX$_1$GSNKYYAX$_2$SVKGRFTISRDNSKNTLNLQMNSLRAEDTAVYYCAK

GALTHWGVVIGX$_3$GMDVWGQGTTVTVSS, wherein $X_1$, $X_2$ and $X_3$ can each independently be any naturally occurring amino acid; and/or a light chain variable region having the amino acid sequence selected from the group consisting of;

a) NFX$_1$LTQPHSVSESPGKTVTISCTRSSGSIASNYV QWYQQRPGSSPTTVI-YEDDQRPSGVPDRFSGSIDSSSNSASLTiSGLK TEDEADYYCQSFX$_2$STNPWVFGGGTKLTVL (SEQ ID NO: 20) wherein $X_1$ and $X_2$ can be any naturally occurring amino acid;

b) NFX$_1$LTQPHSVSESPGKTVTISCISNDVPASGHYH RWYQQRPGSSPTTVI-YEDDQRPSGVPDRFSGSIDSSSNSASLTISGLK TEDEADYYCQSFX$_2$STNPWVFGGGTKLTVL (SEQ ID NO: 35) wherein $X_2$ and $X_2$ can each independently be any naturally occurring amino acid;

c) NFX$_1$LTQPHSVSESPGKTVTISCVLSPRTHAGHY YRWYQQRPGSSPTTVIY-EDDQRPSGVPDRFSGSIDSSSNSASLTISGLK TEDEADYYCQSFX$_2$STNPWVFGGGTKLTVL (SEQ ID NO: 38), wherein $X_1$ and $X_2$ can each independently be any naturally occurring amino acid;

d) NFX$_1$LTQPHSVSESPGKTVTISCX$_2$RTGTGNKGH YTRWYQQRPGSSPTTVI-YEDDQRPSGVPDRFSGSIDSSSNSASLTISGL KTEDEADYYCQSFXSSTNPWVFGGGTKLTVL (SEQ ID NO: 41), wherein $X_1$, $X_2$ and $X_3$ can each independently be any naturally occurring amino acid;

e) NFX$_1$LTQPHSVSESPGKTVTiSCRETELSRRLHYV RWYQQRPGSSPTTVI-YEDDQRPSGVPDRFSGSIDSSSNSASLTISGLKT EDEADYYCQSFX$_2$STNPWVFGGGTKLTVL (SEQ ID NO: 47), wherein $X_1$ and $X_2$ can each independently be any naturally occurring amino acid; and f) NFX$_1$LTQPHSVSESPGKTVTISCRGTGSSFHHKY VRWYQQRPGSSPTTVI-YEDDQRPSGVPDRFSGSIDSSSNSASLTISGLK TEDEADYYCQSFX$_2$STNPWVFGGGTKLTVL (SEQ ID NO: 50), wherein $X_1$ and $X_2$ can each independently be any naturally occurring amino acid.

In one embodiment, there is provided an antigen binding molecule (for example an antibody or antigen-binding fragment thereof) that binds to PD-L1 and comprises a heavy chain variable region having the amino acid sequence:

(SEQ ID NO: 27)
QVQLVQSGGGVVQPGRSLRLSCAASGFTFSSYGMYWVRQAPGKGLEWVAV

ISYX$_1$GSNKYYAX$_2$SVKGRFTISRDNSKNTLNLQMNSLRAEDTAVYYCAK

GALTHWGVVIGX$_3$GMDVWGQGTTVTVSS, wherein $X_1$, $X_2$ and $X_3$ are each independently selected from the group consisting of Asp, Gln, Glu and Ala; and/or a light chain variable region having the amino acid sequence selected from the group consisting of;

a) NFX$_1$LTQPHSVSESPGKTVTISCTRSSGSIASNYV QWYQQRPGSSPTTVI-
YEDDQRPSGVPDRFSGSIDSSSNSASLTiSGLK
TEDEADYYCQSFX$_2$STNPWVFGGGTKLTVL
(SEQ ID NO: 21) wherein $X_1$ is selected from the group consisting of Met or Leu, and $X_2$ is selected from the group consisting of Asp, Gln, Glu and Ala;

b) NFX$_1$LTQPHSVSESPGKTVTISCISNDVPASGHYH RWYQQRPGSSPTTVI-
YEDDQRPSGVPDRFSGSIDSSSNSASLTISGLK
TEDEADYYCQSFX$_2$STNPWVFGGGTKLTVL
(SEQ ID NO: 36) wherein $X_1$ is selected from the group consisting of Met or Leu, and $X_2$ is selected from the group consisting of Asp, Gln, Glu and Ala;

c) NFX$_1$LTQPHSVSESPGKTVTISCVLSPRTHAGHY YRWYQQRPGSSPTTVIY-
EDDQRPSGVPDRFSGSIDSSSNSASLTISGLK
TEDEADYYCQSFX$_2$STNPWVFGGGTKLTVL
(SEQ ID NO: 39), wherein $X_1$ is selected from the group consisting of Met or Leu and $X_2$ is selected from the group consisting of Asp, Gln, Glu and Ala;

d) NFX$_1$LTQPHSVSESPGKTVTISCX$_2$RTGTGNKGH YTRWYQQRPGSSPTTVI-
YEDDQRPSGVPDRFSGSIDSSSNSASLTISGL
KTEDEADYYCQSFX$_3$STNPWVFGGGTKLTVL
(SEQ ID NO: 42), wherein $X_1$ is selected from the group consisting of Met or Leu; $X_2$ is selected from the group consisting of Met, Ala and Leu, and $X_3$ is selected from the group consisting of Asp, Gln, Glu and Ala;

e) NFX$_1$LTQPHSVSESPGKTVTISCRETELSRRLHYV RWYQQRPGSSPTTVI-
YEDDQRPSGVPDRFSGSIDSSSNSASLTISGLKT
EDEADYYCQSFX$_2$STNPWVFGGGTKLTVL (SEQ ID NO: 48), wherein $X_1$ is selected from the group consisting of Met or Leu, and $X_2$ is selected from the group consisting of Asp, Gln, Glu and Ala; and f) NFX$_1$LTQPHSVSESPGKTVTISCRGTGSSFHHKY VRWYQQRPGSSPTTVI-
YEDDQRPSGVPDRFSGSIDSSSNSASLTISGLK
TEDEADYYCQSFX$_2$STNPWVFGGGTKLTVL
(SEQ ID NO: 51) wherein $X_1$ is selected from the group consisting of Met or Leu, and $X_2$ is selected from the group consisting of Asp, Gin, Glu and Ala.

In one embodiment, there is provided an antigen binding molecule (for example an antibody or antigen-binding fragment thereof) that binds to PD-L1 and comprises a heavy chain variable region having the amino acid sequence:

(SEQ ID NO: 28)
QVQLVQSGGGVVQPGRSLRLSCAASGFTFSSYGMYWVRQAPGKGLEWVAV

ISYX$_1$GSNKYYAX$_2$SVKGRFTISRDNSKNTLNLQMNSLRAEDTAVYYCAK

GALTHWGVVIGX$_3$GMDVWGQGTTVTVSS, wherein $X_1$, $X_2$ and $X_3$ are each independently selected from the group consisting of Gln, Glu and Ala; and/or a light chain variable region having the amino acid sequence selected from the group consisting of;

a) NFX$_1$LTQPHSVSESPGKTVTiSCTRSSGSIASNYV QWYQQRPGSSPTTVIY-
EDDQRPSGVPDRFSGSIDSSSNSASLTiSGLK
TEDEADYYCQSFX$_2$STNPWVFGGGTKLTVL
(SEQ ID NO: 22) wherein $X_1$ is Leu, and $X_2$ is selected from the group consisting of Gln, Glu and Ala;

b) NFX$_1$LTQPHSVSESPGKTVTISCISNDVPASGHY HRWYQQRPGSSPTTVI-
YEDDQRPSGVPDRFSGSIDSSSNSASLTISGLK
TEDEADYYCQSFX$_2$STNPWVFGGGTKLTVL
(SEQ ID NO: 37) wherein $X_1$ is Leu, and $X_2$ is selected from the group consisting of Gln, Glu and Ala;

c) NFX$_1$LTQPHSVSESPGKTVTISCVLSPRTHAGHY YRWYQQRPGSSPTTVYEDDQRPSGVPDRFSGSI DSSSNSASLTISGLK
TEDEADYYCQSFX$_2$STNPWVFGGGTKLTVL
(SEQ ID NO: 40), wherein $X_1$ is Leu and $X_2$ is selected from the group consisting of Gln, Glu and Ala;

d) NFX$_1$LTQPHSVSESPGKTVTISCX$_2$RTGTGNKGH YTRWYQQRPGSSPTTVI-
YEDDQRPSGVPDRFSGSIDSSSNSASLTISGL
KTEDEADYYCQSFX$_3$STNPWVFGGGTKLTVL
(SEQ ID NO: 43), wherein $X_1$ is Leu; $X_2$ is selected from the group consisting of Ala and Leu, and $X_3$ is selected from the group consisting of Gln, Glu and Ala;

e) NFX$_1$LTQPHSVSESPGKTVTISCRETELSRRLHYV RWYQQRPGSSPTTVI-
YEDDQRPSGVPDRFSGSIDSSSNSASLTISGLKT
EDEADYYCQSFX$_2$STNPWVFGGGTKLTVL (SEQ ID NO: 49), wherein $X_1$ is Leu, and $X_2$ is selected from the group consisting of Gln, Glu and Ala; and f) NFX$_1$LTQPHSVSESPGKTVTISCRGTGSSFHHKY VRWYQQRPGSSPTTVI-
YEDDQRPSGVPDRFSGSIDSSSNSASLTISGLK
TEDEADYYCOSFX$_2$STNPWVFGGGTKLTVL
(SEQ ID NO: 52) wherein $X_1$ is Leu, and $X_2$ is selected from the group consisting of Gln, Glu and Ala.

In one embodiment, an antigen-binding molecule, for example an antibody, variant or fragment thereof is provided, wherein the antigen-binding molecule comprises a heavy chain variable region and a light chain variable region selected from the group consisting of:

a) a VH comprising the amino acid sequence of SEQ ID NO: 5 and a VL comprising the amino acid sequence of SEQ ID NO: 15;

b) a VH comprising the amino acid sequence of SEQ ID NO: 5 and a VL comprising the amino acid sequence of SEQ ID NO: 11;

c) a VH comprising the amino acid sequence of SEQ ID NO: 5 and a VL comprising the amino acid sequence of SEQ ID NO: 9;

d) a VH comprising the amino acid sequence of SEQ ID NO: 5 and a VL comprising the amino acid sequence of SEQ ID NO: 13;

e) a VH comprising the amino acid sequence of SEQ ID NO: 5 and a VL comprising the amino acid sequence of SEQ ID NO: 17;

f) a VH comprising the amino acid sequence of SEQ ID NO: 5 and a VL comprising the amino acid sequence of SEQ ID NO: 1;

optionally wherein the Met residues are each independently substituted with an amino acid selected from the group consisting of Ala and Leu, and the Asp residues are each independently substituted with an amino acid selected from the group consisting of Ala, Gln and Glu.

Variant antigen-binding molecules having the one or more amino acid substitutions may retain the functional activity (for example preferential pH binding, EC50, IC50 and/or Kd) of the antigen-binding molecule from which the variant antigen-binding molecule is derived. Variant antigen-binding molecules of the invention can be used and formulated in the same ways as described for the antigen-binding molecules from which they are derived.

Other Antigen Binding Molecules of the Invention

The invention also provides an anti-PD-L1 antigen binding molecule having the following CDRH and CDRL sequences:

| Light | CDR1 | $X_1X_2X_3X_4X_5X_6X_7X_8X_9X_{10}YX_{11}X_{12}$ |
|-------|------|------|
|       | CDR2 | EDDQRPS |
|       | CDR3 | QSFX$_{13}$STNPWV |
| Heavy | CDR1 | SYGMY |
|       | CDR2 | VISYX$_{14}$GSNKYYAX$_{15}$SVKG |
|       | CDR3 | GALTHWGVVIGX$_{16}$GMDV | wherein each of $X_1$ to $X_{16}$ may be any amino acid, preferably any naturally occurring amino acid.

In preferred embodiments, each of $X_1$ to $X_{16}$ are independently selected from the group consisting of T, I, V, M, R, S, L, E, G, N, D, P, A, H, F, K, Y, Q.

In one embodiment:

$X_1$ is selected from the group consisting of A, L, T, I, V, M, R or a conservative amino acid substitution thereof;

$X_2$ is selected from the group consisting of R, S, L, E, G or a conservative amino acid substitution thereof;

$X_3$ is selected from the group consisting of S, N, T or a conservative amino acid substitution thereof;

$X_4$ is selected from the group consisting of S, D, P, G, E or a conservative amino acid substitution thereof;

$X_5$ is selected from the group consisting of G, V, R, T, L and S or a conservative amino acid substitution thereof;

$X_6$ is selected from the group consisting of S, P, T, G or a conservative amino acid substitution thereof;

$X_7$ is selected from the group consisting of I, A, H, N, R, F or a conservative amino acid substitution thereof;

$X_8$ is selected from the group consisting of A, S, K, R, H or a conservative amino acid substitution thereof;

$X_9$ is selected from the group consisting of S, G, L, H or a conservative amino acid substitution thereof;

$X_{10}$ is selected from the group consisting of N, H, K or a conservative amino acid substitution thereof;

$X_{11}$ is selected from the group consisting of V, H, Y, T or a conservative amino acid substitution thereof;

$X_{12}$ is selected from the group consisting of Q, R or a conservative amino acid substitution thereof;

$X_{13}$ is selected from the group consisting of D, Q E, A or a conservative amino acid substitution thereof;

$X_{14}$ is selected from the group consisting of D, Q, E, A or a conservative amino acid substitution thereof;

$X_{15}$ is selected from the group consisting of D, Q, E, A or a conservative amino acid substitution thereof; and $X_{16}$ is selected from the group consisting of D, Q, E, A or a conservative amino acid substitution thereof.

In one embodiment:

$X_1$ is selected from the group consisting of A, L, T, I, V, M and R;

$X_2$ is selected from the group consisting of R, S, L, E and G;

$X_3$ is selected from the group consisting of S, N and T;

$X_4$ is selected from the group consisting of S, D, P, G and E;

$X_5$ is selected from the group consisting of G, V, R, T, L and S;

$X_6$ is selected from the group consisting of S, P, T and G;

$X_7$ is selected from the group consisting of I, A, H, N, R and F;

$X_8$ is selected from the group consisting of A, S, K, R and H;

$X_9$ is selected from the group consisting of S, G, L and H;

$X_{10}$ is selected from the group consisting of N, H and K;

$X_{11}$ is selected from the group consisting of V, H, Y and T;

$X_{12}$ is selected from the group consisting of Q and R;

$X_{13}$ is selected from the group consisting of D, Q, E and A(;

$X_{14}$ is selected from the group consisting of D, Q, E and A;

$X_{15}$ is selected from the group consisting of D, Q, E and A; and $X_{16}$ is selected from the group consisting of D, Q E and A.

In one embodiment (SEQ ID NO: 57):

$X_1$ is selected from the group consisting of A, L, T, I, V and R;

$X_2$ is selected from the group consisting of R, S, L, E and G;

$X_3$ is selected from the group consisting of S, N and T;

$X_4$ is selected from the group consisting of S, D, P, G and E;

$X_5$ is selected from the group consisting of G, V, R, T, L and S;

$X_6$ is selected from the group consisting of S, P, T and G;

$X_7$ is selected from the group consisting of I, A, H, N, R and F;

$X_8$ is selected from the group consisting of A, S, K, R and H;

$X_9$ is selected from the group consisting of S, G, L and H;

$X_{10}$ is selected from the group consisting of N, H and K;

$X_{11}$ is selected from the group consisting of V, H, Y and T;

$X_{12}$ is selected from the group consisting of Q and R;

$X_{13}$ is selected from the group consisting of Q, E and A;

$X_{14}$ is selected from the group consisting of Q, E and A;

$X_{15}$ is selected from the group consisting of Q, E and A; and $X_{16}$ is selected from the group consisting of Q, E and A.

Such antibodies may preferably have the functional profile of one or more of 8B06, 8D06, 8G08, 8A04, 8D04 or 2A09.

The invention also provides an anti-PD-L1 antigen binding molecule having the following VH and VL sequences

```
VH:
QVQLVQSGGGVVQPGRSLRLSCAASGFTFSSYGMYWVRQAPGKGLEWVAV

ISYX₁GSNKYYAX₂SVKGRFTISRDNSKNTLNLQMNSLRAEDTAVYYCAK

GALTHWGVVIGX₃GMDVWGQGTTVTVSS

VL:
NFX₄LTQPHSVSESPGKTVTISCX₅X₆X₇X₈X₉X₁₀X₁₁X₁₂X₁₃X₁₄Y

X₁₅X₁₆WYQQRPGSSPTTVIYEDDQRPSGVPDRFSGSIDSSSNSASLTI

SGLKTEDEADYYCQSFX₁₇STNPWVFGGGTKLTVL
``` wherein each of $X_1$ to $X_{17}$ may be any amino acid, preferably any naturally occurring amino acid (i.e. the VH sequence comprises SEQ ID NO: 53 and the VL sequence comprises SEQ ID NO: 58).

In preferred embodiments, each of $X_1$ to $X_{17}$ are independently selected from the group consisting of T, I, V, M, R, S, L, E, G, N, D, P, A, H, F, K, Y, Q (i.e. the VH sequence comprises SEQ ID NO: 54 and the VL sequence comprises SEQ ID NO: 59).

In one embodiment:

$X_1$ is selected from the group consisting of D, Q, E, A or a conservative amino acid substitution thereof;

$X_2$ is selected from the group consisting of D, Q, E, A or a conservative amino acid substitution thereof;

$X_3$ is selected from the group consisting of D, Q, E, A or a conservative amino acid substitution thereof;

$X_4$ is selected from the group consisting of M, L, or a conservative amino acid substitution thereof;

$X_5$ is selected from the group consisting of A, L, T, I, V, M, R or a conservative amino acid substitution thereof;

$X_6$ is selected from the group consisting of R, S, L, E, G or a conservative amino acid substitution thereof;

$X_7$ is selected from the group consisting of S, N, T or a conservative amino acid substitution thereof;

$X_8$ is selected from the group consisting of S, D, P, G, E or a conservative amino acid substitution thereof;

$X_9$ is selected from the group consisting of G, V, R, T, L and S or a conservative amino acid substitution thereof;

$X_{10}$ is selected from the group consisting of S, P, T, G or a conservative amino acid substitution thereof;

$X_{11}$ is selected from the group consisting of I, A, H, N, R, F or a conservative amino acid substitution thereof;

$X_{12}$ is selected from the group consisting of A, S, K, R, H or a conservative amino acid substitution thereof;

$X_{13}$ is selected from the group consisting of S, G, L, H or a conservative amino acid substitution thereof;

$X_{14}$ is selected from the group consisting of N, H, K or a conservative amino acid substitution thereof;

$X_{15}$ is selected from the group consisting of V, H, Y, T or a conservative amino acid substitution thereof;

$X_{16}$ is selected from the group consisting of Q, R or a conservative amino acid substitution thereof; and $X_{17}$ is selected from the group consisting of D, Q, E, A or a conservative amino acid substitution thereof (i.e. the VH sequence comprises SEQ ID NO: 55 and the VL sequence comprises SEQ ID NO: 60)

In one embodiment:

$X_1$ is selected from the group consisting of D, Q, E and A;

$X_2$ is selected from the group consisting of D, Q, E and A;

$X_3$ is selected from the group consisting of D, Q, E, and A;

$X_4$ is selected from the group consisting of M and L;

$X_5$ is selected from the group consisting of A, L, T, I, V, M and R;

$X_6$ is selected from the group consisting of R, S, L, E and G;

$X_7$ is selected from the group consisting of S, N and T;

$X_8$ is selected from the group consisting of S, D, P, G and E;

$X_9$ is selected from the group consisting of G, V, R, T, L and S $X_{10}$ is selected from the group consisting of S, P, T and G;

$X_{11}$ is selected from the group consisting of I, A, H, N, R and F;

$X_{12}$ is selected from the group consisting of A, S, K, R and H;

$X_{13}$ is selected from the group consisting of S, G, L and H;

$X_{14}$ is selected from the group consisting of N, H and K;

$X_{15}$ is selected from the group consisting of V, H, Y and T;

$X_{16}$ is selected from the group consisting of Q and R; and $X_{17}$ is selected from the group consisting of D, Q, E and A (i.e. the VH sequence comprises SEQ ID NOs 56 and the VL sequence comprises SEQ ID NO: 61)

In one embodiment:

$X_1$ is selected from the group consisting of Q, E and A;

$X_2$ is selected from the group consisting of Q, E and A;

$X_3$ is selected from the group consisting of Q, E, and A;

$X_4$ is L;

$X_5$ is selected from the group consisting of L, T, I, V, M and R;

$X_6$ is selected from the group consisting of S, L, E and G;

$X_7$ is selected from the group consisting of N and T;

$X_8$ is selected from the group consisting of D, P, G and E;

$X_9$ is selected from the group consisting of V, R, T, L and S $X_{10}$ is selected from the group consisting of P, T and G;

$X_{11}$ is selected from the group consisting of A, H, N, R and F;

$X_{12}$ is selected from the group consisting of S, K, R and H;

$X_{13}$ is selected from the group consisting of G, L and H;

$X_{14}$ is selected from the group consisting of H and K;

$X_{15}$ is selected from the group consisting of H, Y and T;

$X_{16}$ is R; and $X_{17}$ is selected from the group consisting of E and A (i.e. the VH sequence comprises SEQ ID NO: 57 and the VL sequence comprises SEQ ID NO: 62)

Nucleic Acid Sequences Encoding Antigen-Binding Molecules

In one aspect of the invention, there is provided nucleic acid sequences that encode the antigen binding molecules of the invention, including fragments and variants thereof.

In one embodiment, nucleotides encoding an antigen binding molecule that binds to PD-L1 comprising a heavy chain variable region having at least 70%, 75%, 80%, 85%, 90%, 91%, 92%, 93%, 94%, 95%, 96%, 97%, 98% or 99% identity to the amino acid sequence SEQ ID NO: 5, and/or a light chain variable region having at least 70%, 75%, 80%, 85%, 90%, 91%, 92%, 93%, 94%, 95%, 96%, 97%, 98% or 99% identity to an amino acid sequence selected from the group consisting of SEQ ID NO: 15, SEQ ID NO: 11, SEQ ID NO: 9, SEQ ID NO: 13, SEQ ID NO: 17, SEQ ID NO: 1 are provided.

In one embodiment, nucleotides encoding an antigen binding molecule that binds to PD-L1 comprising a heavy chain variable region having the amino acid sequence SEQ ID NO: 5, and/or a light chain variable region having an amino acid sequence selected from the group consisting of SEQ ID NO: 15, SEQ ID NO: 11, SEQ ID NO: 9, SEQ ID NO: 13, SEQ ID NO: 17, SEQ ID NO: 1 are provided.

The present invention also provides nucleic acid molecules encoding all of the variant antibody sequences disclosed herein comprising one or more amino acid substitutions.

Also provided are nucleic acid molecules that encode an amino acid sequence according to any one of SEQ ID NOs 1 to 62.

Also provided are plasmid and vectors comprising a nucleic acid sequence encoding an antigen-binding molecule of the invention. The nucleic acids may be incorporated into a plasmid or vector for expression, in particular in a eukaryotic expression systems, more specifically, mammalian cell lines. Accordingly, also provided are host cells transfected with a plasmid or vector of the invention, such as HEK cells, NSO murine myeloma cells or CHO cells.

Also provided is a method for the production of an anti-PD-L1 antigen binding molecule, comprising culturing a host of the invention in a cell culture medium under conditions to express the encoding nuclide acid sequence of the plasmid or vector inside the cell. The method may further comprise obtaining the anti-PD-L1 antigen binding molecule from the cell culture supernatant. Further, there is provided a method of producing cell that expresses an anti-PD-L1 antigen binding molecule, comprising transfecting said cell with a plasmid or vector of the invention. Said cells can then be cultured for the production of the antigen-binding molecule.

Antigens

The antigen-binding molecules of the invention bind specifically to PD-L1, in particular human PD-L1, or hPD-L1. The antigen-binding molecules of the invention also bind specifically to cynomolgus PD-L1. Most preferably, the antigen-binding molecules of the invention specifically bind to human PD-L1.

The antigen binding molecules of the invention generally do not bind to mouse PD-L1.

PD-L1 (programmed death-ligand 1) is one of two described ligands for the inhibitory receptor PD-1 (programmed death 1 polypeptide. PD-L1 is a type 1 transmembrane protein involved in suppressing the adaptive immune system. Upregulation of PD-L1 may allow cancers to evade the immune system.

PD-L1 is expressed at low levels on immune cells such as B cells, dendritic cells, macrophages and T cells and is up regulated following activation. PD-L1 is also expressed on non-lymphoid organs such as endothelial cells, heart, lung, pancreas, muscle, keratinocytes and placenta. The expression within non lymphoid tissues suggests that PD-L1 may regulate the function of self-reactive T and B cells as well as myeloid cells in peripheral tissues or may regulate inflammatory responses in the target organs. PD-L1 expression is mainly regulated by type 1 and 2 interferon which are major regulators of PD-L1 on endothelial and epithelial cells. PD-L1 is abundant in a variety of human cancers and the interaction between PD-1 and PD-L1 results in a decrease in tumor infiltrating lymphocytes, a decrease in T-cell receptor mediated proliferation, and immune evasion by the cancerous cells. PD-L1 is expressed in tumor samples and is associated with poor prognosis. Immune suppression can be reversed by inhibiting the local interaction of PD-1 with PD-L1. The inhibition of PD-L1 signalling has been shown to enhance T cell immunity for the treatment of cancer.

The amino acid sequences of human PD-L1 to which the antigen-binding molecules of the invention bind is provided below.

Human PD-L1 (NCBI Reference Sequence: NP_054862.1)

```
Amino Acid Sequence
                                       (SEQ ID NO: 19)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET
```

The anti-PD-L1 antigen binding molecules of the invention specifically binds to PD-L1 in a pH dependent manner.

In one embodiment the anti-PD-L1 antigen binding molecules of the invention specifically binds to PD-L1 in a pH dependent manner, for example when in a monovalent format. Monovalent formats include formats such as a Fab fragment. It is hypothesised this may be due to the affinity of the Fab being less (for example approximately 100-fold less) than a monoclonal antibody, and/or the presence of histidine residues into the CDRs.

The antigen binding molecules of the invention demonstrated significantly higher affinity for PD-L1 at acidic pH (about pH 6.0) compared to physiological pH (about pH 7.4). This contrasts with other PD-L1 binding molecules known in the art, which do not demonstrate pH specific binding and many in fact show lower affinity at pH 6.0 compared to pH 7.4.

The antigen binding molecules of the invention also demonstrated a clear pH dependence of inhibition. The antigen binding molecules of the invention have significantly more inhibitory activity for PD-L1 at acidic pH (about pH 6.0) compared to physiological pH (about pH 7.4). At pH 7.4 the antigen binding molecules of the invention have very little inhibitory activity for PD-L1. This contrasts with other PD-L1 binding molecules known in the art, which do not demonstrate pH dependence of inhibition.

This pH specific binding is significant, since the tumors and their microenvironments are acidic (for example from about pH 6.0 to about pH 6.5). Anti-PD-L1 binding molecules that have maximum activity at pH 6-6.5, (the acidic pH of a tumor) and reduced activity at physiological pH of 7.4 can therefore reduce peripheral checkpoint inhibitor treatment toxicity and other side effects. Therefore, the antigen-binding molecules of the invention are particularly useful as potential anti-cancer agents.

The antigen-binding molecules of the invention that bind PD-L1 will also therefore bind to cells that express PD-L1.

EC50

In one embodiment, the antigen binding molecules of the present invention have an EC50 value for PD-L1 or PD-L1 positive cells at pH 6.0 of less than about 15 nM. In one embodiment, the antigen binding molecules of the present invention have an EC50 value for PD-L1 at pH 6.0 of from about 1.45 nM to about 15 nM.

In one embodiment, the antigen binding molecules of the present invention have an EC50 value for PD-L1 at pH 7.4 of at least about 10 nM. In one embodiment, the antigen binding molecules of the present invention have an EC50 value for PD-L1 at pH 7.4 of from about 13.2 nM to about 100 nM.

The antigen binding molecules of the present invention have a significantly higher potency (EC50) when binding to PD-L1 at acidic pH (pH 6.0) than physiological pH (pH 7.4). The antigen binding molecules of the present invention have a pH 6.0:7.4 binding ratio of at least about 5, meaning the EC50 at pH 6.0 is at least about 5 times lower than at pH 7.4 and the antigen binding molecules are at least about 5 times more potent at pH 6.0 than at pH 7.4.

In a preferred embodiment the antigen binding molecules of the present invention have an EC50 value for PD-L1 at pH 6.0 of less than about 15 nM and an EC50 value for PD-L1 at pH 7.4 of at least about 10 nM, wherein the antigen binding molecule has a pH 6.0:7.4 binding ratio of at least about 5.

The term EC50 Is well known to the skilled person and refers to the half maximal effective concentration of a drug or substance, or the concentration of that substance which induces a response halfway between the maximum response after a specified exposure time and the baseline. EC50 is a measure of potency. The lower the EC50, the greater the potency of the drug or substance. The EC50 can be measured according to any suitable means known to the skilled person.

In a cell binding assay the EC50 may refer to the concentration of Fab which induces a response (MFI) about halfway between the baseline and maximum after an incubation with 0.60E05 MDA-MB-231 cells for about 60 minutes at about 4° C. In an ELISA assay the EC50 may refer to the concentration of Fab which induces a response (OD) about halfway between the baseline and maximum after an incubation with about 1 μg/ml of human PD-L1-Fc protein coated well for about 2 h at room temperature (for example from about 15° C. to about 25° C.).

IC50

In one embodiment, the antigen binding molecules of the present invention have an IC50 value for inhibiting PD-L1:PD-1 binding at pH 6.0 of less than about 50 nM. In one embodiment, the antigen binding molecules of the present invention have an IC50 value for PD-L1 at pH 6.0 of from about 12.1 nM to about 42.3 nM.

In one embodiment, the antigen binding molecules of the present invention have an IC50 value for inhibiting PD-L1:PD-1 binding at pH 7.4 of at least about 50 nM. In one embodiment, the antigen binding molecules of the present invention have an IC50 value for PD-L1 at pH 7.4 of from about 81.2 nM to about 100 nM.

The antigen binding molecules of the present invention have a significantly higher inhibitory activity (IC50) on PD-L1:PD-1 binding at acidic pH (pH 6.0) than physiological pH (pH 7.4). The antigen binding molecules of the present invention have a pH 6.0:7.4 inhibitory ratio of at least 2, meaning the IC50 at pH 6.0 is at least 2 times lower than at pH 7.4 and the antigen binding molecules are at least 5 times more potent at inhibition at pH 6.0 than at pH 7.4.

In a preferred embodiment the antigen binding molecules of the present invention have an IC50 value for PD-L1 at pH 6.0 of less than about 50 nM and an IC50 value for PD-L1 at pH 7.4 of at least about 50 nM, wherein the antigen binding molecule has a pH 6.0:7.4 inhibitory ratio of at least about 2.

The term IC0 is well known to the skilled person and refers to the half maximal inhibitory concentration of a drug or substance, or the concentration of that substance which induces 50% inhibition. IC50 is a measure of the potency of a substance in inhibiting a specific biological or biochemical function. The lower the IC50, the greater the potency of the antagonist drug or substance as an inhibitor. The IC50 can be measured according to any suitable means known to the skilled person. For example, in a PD-L1-PD-1 inhibition ELISA, the IC50 may be the half maximal inhibitory concentration of a Fab inhibiting about 1 μg/ml PD-L1 biotin binding to a well coated with about 1 μg/mi of PD-1-Fc protein.

Of course, for any of the functional features of the antibodies, comparisons of functional features are conducted under substantially the same experimental conditions, except for pH, since the effect of the change in pH is being measured. Other features of the assay measuring the functional features (such as IC50, EC50 or $K_D$) are kept the same, insofar as this is possible.

In some embodiments of the invention, the inventors have discovered the antigen binding molecules compete with PD-L1 binding to the inhibitory receptor programmed death 1 polypeptide (PD-1) and co-stimulatory molecule CD80. This mechanism is relevant since PD-L1 is abundant in a variety of human cancers and the interaction between PD-1 and PD-L1 results in a decrease in tumor infiltrating lymphocytes, a decrease in T-cell receptor mediated proliferation, and immune evasion by the cancerous cells. Immune suppression can be reversed by inhibiting the local interaction of PD-1 with PD-L1. The inhibition of PD-L1 signalling has been shown to enhance T cell immunity for the treatment of cancer. The antigen binding molecules of the invention inhibit the binding of PD-L1 and its receptors by at least 40%, at least 50% or at least 80%.

The present inventors have also found that the antigen binding molecules of the invention inhibits the binding of PD-L1 expressing cells to PD-1 and/or CD80.

The pH-sensitive binding nature of the antigen binding molecules of the invention may result in the antigen binding molecules having at least 5 fold higher affinity at acidic pH (for example at pH 6) that at physiological pH (for example about pH 7.4). The affinity of an antigen binding molecule of the invention for its epitope can be measured using surface plasmon resonance (SPR). For example, a BIAcore SPR system (BIAcore 3000, GE Healthcare) can be used. The BIAcore system is used to monitor molecular interactions in real time and the detection principle is based on surface plasmon resonance (SPR), that is sensitive to changes in refractive index within about 150 nm from the sensor surface. For example, PD-L1-Fc can be attached to the surface and the test anti-PD-L1 antigen binding molecules can be passed over the surface in a continuous flow of sample solution. The SPR response is directly proportional to the change in mass concentration close to the surface and the kinetic parameters are evaluated from the association and dissociation phases of the sensogram.

In one aspect, an anti-PD-L1 antigen binding molecule, for example an antibody, fragment or variant thereof is provided, wherein the antigen binding molecule competes for binding to PD-L1 with an antigen binding molecule of the invention as defined above.

For example, in one embodiment the invention provides an antigen binding molecule (preferably an antibody) wherein the antigen binding molecule specifically binds to PD-L1, in particular human PD-L1, and competes for binding to PD-L1 with an antibody selected from the group consisting of 8B06, 8D06, 8G08, 8A04, 8D04 and 2A09. Antigen binding molecules that compete with the fragments and variants thereof for binding to PD-L1 are also provided (for example antigen-binding molecules comprising the 6 CDR regions or the VH and VL sequences of the above antibodies, as well as other variants).

To determine if a test antibody can compete for binding to the same epitope as the epitope bound by the antibodies of the present invention, a cross-blocking assay e.g., a competitive ELISA assay can be performed. In an exemplary competitive ELISA assay, PD-L1-coated wells of a microtiter plate, or PD-L1-coated sepharose beads, are pre-incubated with or without candidate competing antibody and then a biotin-labelled anti-PD-L1 antibody of the invention is added. The amount of labelled anti-PD-L1 antibody bound to the PD-L1 antigen in the wells or on the beads can be measured using avidin peroxidase conjugate and appropriate substrate.

Alternatively, the anti-PD-L1 antibody can be labelled, e.g., with a radioactive or fluorescent label or some other detectable and measurable label. The amount of labelled anti-PD-L1 antibody that binds to the antigen will have an inverse correlation to the ability of the candidate competing antibody (test antibody) to compete for binding to the same epitope on the antigen, i.e., the greater the affinity of the test antibody for the same epitope, the less labelled anti-PD-L1 antibody will be bound to the antigen-coated wells. A candidate competing antibody is considered an antibody that binds substantially to the same epitope or that competes for binding to the same epitope as an anti-PD-L1 antibody of the invention if the candidate competing antibody can block binding of the anti-PD-L1 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

There is also provided an antigen-binding molecule that specifically binds to PD-L1 and inhibits the binding of PD-L1 to an antigen-binding molecule of the invention.

For example, in one embodiment, the antigen-binding molecule (preferably an antibody) specifically binds to PD-L1 and inhibits the binding of PD-L1 to an antibody selected from the group consisting of 8B06, 8D06, 8G08, 8A04, 8D04 and 2A09. Antigen binding molecules that specifically bind to PD-L1 and inhibit the binding of PD-L1 to fragments and variants thereof are also provided (for example antigen-binding molecules comprising the 6 CDR regions or the VH and VL sequences of the above antibodies, as well as other variants).

There is also provided an antigen-binding molecule that specifically binds to an epitope of PD-L1 that is bound by an antigen-binding molecule of the invention.

For example, in one embodiment the invention provides an antigen binding molecule (preferably an antibody) wherein the antigen binding molecule specifically binds to an epitope of PD-L1 that is bound by an antibody selected from the group consisting of 8B06, 8D06, 8G08, 8A04, 8D04 and 2A09. Antigen binding molecules that specifically bind to an epitope of PD-L1 that is bound by fragments and variants thereof are also provided (for example antigen-binding molecules comprising the 6 CDR regions or the VH and VL sequences of the above antibodies, as well as other variants).

Compositions

In one aspect of the invention, a pharmaceutical composition comprising an antigen binding molecule of the invention is provided.

The composition in accordance with this aspect of the invention can be formulated for use by any convenient route. The pharmaceutical composition of the invention will normally include a pharmaceutically acceptable carrier, excipient, diluent, adjuvant, vehicle, buffer or stabiliser in addition to an antigen binding molecule of the invention. Such carriers include, but are not limited to, saline, buffered saline, dextrose, liposomes, water, glycerol, polyethylene glycol, ethanol and combinations thereof.

The pharmaceutical composition may be in any suitable form depending upon the desired method of administering it to a patient.

The pharmaceutical compositions of the invention may be presented in unit dose forms containing a predetermined amount of each active ingredient per dose. Such a unit may be adapted to provide 0.5-50 mg/kg of the compound, preferably either 1-10 mg/kg, 1-5 mg/kg, 5-10 mg/kg or 10-50 mg/kg Such doses can be provided in a single dose or as a number of discrete doses. The ultimate dose will of course depend on the condition being treated, the route of administration and the age, weight and condition of the patient and will be at the doctor's discretion.

The pharmaceutical compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. IV administration may be preferred. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical compositions of the invention can also contain one or more other therapeutically active agents in addition to the molecule of the present invention.

In some embodiments, the formulation of the active drug concentrate can comprise a pharmaceutically acceptable tonicity agent, a buffering agent, and a pharmaceutically acceptable surfactant.

Alternatively, the formulation can comprise the active ingredient plus sodium phosphate, monobasic, sodium phosphate dibasic, sodium chloride, polysorbate 80 or polysorbate 20 (surfactant to minimise risk of agitation-induced aggregation) and water (USP/Ph.Eur), optionally with a pH adjusted to about 6.0 to 7.0, e.g. around 6.5.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

Methods of Treatment

The antigen binding molecules of the invention are useful in preventing and/or treating PD-L1-mediated disorders or diseases, in particular cancer. This aspect of the invention therefore also includes a method for the treatment of a PD-L1-mediated disorder or disease (such as cancer) in a subject, comprising administering to the subject an antigen binding molecule of the invention. The invention therefore also extends to the use of an antigen binding molecule of the invention in the manufacture of a medicament for use in the treatment and/or prevention of a PD-L1-mediated disorder or disease (such as cancer), and use of the antigen-binding molecules of the invention in prevention and/or treatment of such conditions.

The method of treatment can be of a human or an animal subject and the invention extends equally to uses in both human and/or veterinary medicine. The antigen binding molecule of the invention is preferably administered to an individual in a "therapeutically effective amount", this being sufficient to show benefit to the individual. As used herein, "treatment" includes any regime that can benefit a human or non-human animal, preferably mammal. The treatment may be in respect of an existing condition or may be prophylactic (preventative treatment). The method may be an in vitro method. The method may be an in vivo method.

In one embodiment, the antigen binding molecules of the invention enhances T cell immunity when administered in vitro or in vivo.

In one embodiment, the antigen binding molecules of the invention reverses immune suppression when administered in vitro or in vivo.

In one embodiment, the antigen binding molecule of the invention is an immune checkpoint inhibitor.

In one embodiment, the antigen binding molecules of the invention are for use in the treatment of prevention of cancer. As used herein "cancer" relates to a disease caused by an uncontrolled division of abnormal cells. These include cardiac, sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangloma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholanglocarcinoma, hepatoblastoma, anglosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre tumor cervical dysplasia), ovaries (ovarian carcinoma [serous cystadenocarcinoma, mucinous cystadenocarcinoma, unclassified carcinoma], granulosa thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. In another embodiment, the cancer is carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Another particular example of cancer includes renal cell carcinoma. Yet another particular example of cancer is non-hodgkin's lymphoma or cutaneous T-cell lymphoma.

Of particular interest is the treatment or prevention of melanoma, metastatic cancer, non-small cell lung cancer, head and neck cancer, Hodgkin's lymphoma, urothelial carcinoma, gastric cancer, cervical cancer, hepatocellular carcinoma and bladder cancer.

In one embodiment the cancer may be selected from a group consisting of melanoma, metastatic cancer, non-small cell lung cancer, head and neck cancer, Hodgkin's lymphoma, urothelial carcinoma, gastric cancer, cervical cancer, hepatocellular carcinoma and bladder cancer.

Depending on the condition being treated, the antigen-binding molecules of the invention may be used in combination with other pharmaceutically active components for simultaneous, separate or sequential use. For example, when treating or preventing cancer, the antigen-binding molecules of the invention may be used in combination with another therapy or additional therapeutically active agent. Suitable therapies or additional therapeutically active agents include radiation therapy, chemotherapy treatment, targeted therapy, immunotherapy, monoclonal antibody therapy, hormonal therapy, angiogenesis inhibition, cancer vaccines, oncolytic virus, toll like receptor agonists, epigenetic modifications, engineered T cells, T cell co-stimulation agonists, tyrosine kinase inhibitors, other anti-cancer chemical agents, palliative care for cancer therapy, an immune checkpoint inhibitor, an immunosuppressant, an anti-inflammatory, an immune modulators, an immune activator and/or an inhibitor such as an IDO inhibitor, a CSF-1R inhibitor, a TGFB inhibitor, a T cell co-stimulation antagonist, a Treg inhibitor, a macrophage modulator, a natural killer cell modulator and a chemokine receptor inhibitor.

Suitable chemotherapy treatments include gemcitabine, cyclophosphamide, doxorubicin, paclitaxel, cisplatin. Suitable T cell co-stimulation agonists include 4-1BB, OX40, CD40, GITR, and ICOS. The immune checkpoint inhibitor may act on a member of the group consisting of PD-1, CTLA-4, TIM-3, LAG-3, VISTA, BTLA, CD70 and TIGIT.

The other therapy or additional therapeutically active agent may be another antigen binding molecule. The additional antigen binding molecule may be selected from the group consisting of anti-PD-L1 antigen binding molecules, anti-PD-1 antigen binding molecules, anti-CTLA-4 antigen binding molecules, anti-OX40 antigen binding molecules, anti-ICOS antigen binding molecules, anti-GITR antigen binding molecules.

The pharmaceutical compositions of the invention may be formulated to include one or more additional pharmaceutically active components, such as those listed above. The antigen-binding molecules of the invention may be provided as part of a kit. Such kits may include instructions for use and/or additional pharmaceutically active components. The antigen-binding molecules and the additional pharmaceutically active components may be disposed separately within the kit, or in some embodiments the antigen-binding molecules may and the additional pharmaceutically active components may be formulated together.

In one embodiment of the invention there is provided an antibody, in particular a monovalent antibody, such as a Fab fragment, that specifically binds to PD-L1. The antibody is selected from the group consisting of 8B06, 8D06, 8G08, 8A04, 8D04 and 2A09. The antibodies are for use in the treatment or prevention of cancer.

The present invention will now be further described with reference to a number of specific examples, which are presented for illustrated purposes and are not to be construed as limiting on the scope of the invention.

EXAMPLES

Human Naïve Library Construction:

RNA was extracted from PBMC of 6 healthy donors (0.51 of blood/donor). 240 μg of RNA was used for cDNA synthesis using random primers. The cDNA was used in a primary PCR amplification using non-tagged primers annealing at the FRI VH, VO and VA and Hinge CH1 regions, followed by a secondary PCR amplification introducing restriction endonuclease sites for cloning of VH, Vλ and Vκ, genes in a pCB3 phagemid vector. The libraries were electroporated into TG1 E. coli cells and bacterial glycerol stock of the human libraries were stored at −80° C. (Human Naïve Fab Library Pool H002κ-H007κ and Human Naïve Fab library pool H002λ-H007λ).

Selections: pH Selective Anti-PD-L1 Fabs

Phage production from the Human Naïve Fab Library Pool H002κ-H007κ and Human Naïve Fab library pool H002λ-H007λ were used in two consecutive rounds of panning phage display selection with human PD-L1 followed by a third-round panning selection with cynomolgus and mouse PD-L1 proteins and a fourth-round panning with mouse PD-L1, to improve the chances of cross-reactivity clones. (Human, and mouse PD-L1 Fc were obtained from R&D Systems and cynomolgus PD-L1 Fc from Sino biological). All selections rounds were performed using 10 μg/ml of recombinant PD-L1 proteins, at pH 6.0 (CPA Buffer; 10 mM sodium citrate, 10 mM sodium phosphate, 10 mM sodium acetate, 115 mM sodium chloride) with washing of non-specific phage, followed by specific phage elution with trypsin (total elution). Serial dilutions of the eluted phages were performed and used to infect exponentially growing TG1. Infected TG1 was plated on LBCarb100Glu2% plates and enrichment values calculated over the background (without antigen for selection).

ELISA Screening:

Individual clones from the third and fourth round of panning selection conditions outputs were picked into 96-well Master Plates and tested as phage and Periplasmic Extract (P.E.) for binding to human, cynomolgus and mouse PD-L1 at pH 6.0 versus pH 7.4, via binding ELISA.

For the Phage binding ELISA, MaxiSorp™ high protein-binding capacity 96 well ELISA plates, were coated with 1 μg/ml of PD-L1-Fc proteins, diluted in PBS, overnight at 4° C. The next day, plates were washed 3× with CPA Tween 0.05% (pH 6.0) and blocked for 1 hour at room temperature with 250 µl/well of 4% Marvel/CPA (pH6.0). After blocking, plates were washed 3× with CPA Tween 0.05% (pH 6.0) and incubated per well with 10 µl of phage in 90 µl of 1% Marvel/CPA (pH 6.0), for 1 hour at RT with shaking. Plates were then washed 3× with CPA Tween 0.05% (pH 6.0) and incubated per well with 100 µl of anti-M13-HRP (GE cat. no. 27-9421-01) in 1% Marvel/CPA (pH 6.0), for 1 hour at RT with shaking. Plates were washed 3× with CPA Tween 0.05% (pH 6.0), the substrate solution (TMB, ThermoFisher) was added and the reaction was stopped with H2SO4 (ThermoFisher) and the absorbance read at 450 nm.

For the Periplasmic Extract (P.E.) binding ELISA, MaxiSorp™ high protein-binding capacity 96 well ELISA plates, were coated with 1 µg/ml of PD-L1-Fc proteins, diluted in PBS, overnight at 42° C. The next day, plates were washed 3× with CPA Tween 0.05% (pH 6.0) or PBS Tween 0.05% pH 7.4 and blocked for 1 hour at room temperature with 250 µl/well of 4% Marvel/CPA (pH6.0) or 4% Marvel/PBS pH 7.4.

After blocking, plates were washed 3× with CPA Tween 0.05% (pH 6.0) or PBS Tween 0.05% (pH 7.4) and incubated per well with 20 µl of P.E+80 µl 1% Marvel/CPA (pH6.0) or 1% Marvel/PBS (pH 7.4), for 1 hour at RT with shaking. Plates were then washed 3× with CPA Tween 0.05% (pH 6.0) or with PBS Tween 0.05% (pH7.4) and incubated per well with 100 µl of anti-c-Myc-HRP (Bethyl cat. no. A190-105P) in 1% Marvel/CPA (pH 6.0) or in 1% Marvel/PBS (pH7.4) for 1 hour at RT with shaking. Plates were then washed 3× with CPA Tween 0.05% (pH 6.0) or with PBS Tween 0.05% (pH 7.4) and the substrate solution (TMB solution) was added to the plates. Reaction was stopped with H2SO4 and the absorbance read at 450 nm. For most of the clones, binding at both pH's was observed. The positive binders to human PD-L1 were sequenced and clones were classified by families according to the different HCDR3 sequence.

Clones from a family having a histidine in the CDR3, gave higher OD values at pH 6.0 than at pH 7.4 and a panel of family representative clones that bind in ELISA to human, cynomolgus and or mouse PD-L1 were selected for screening for binding to human, cynomolgus and mouse PD-L1 transfected HEK293FF cells.

Screening of Selected Clones in Cells:

Transfection of HEK293FF cells with human, cynomolgus and mouse PD-L1. HEK293FF cells were cultured in Freestyle™293 expression medium and seeded at 0.8E+06 cells/ml on the day of transfection. A Mix of (Lipofectamine 2000+70 µg of DNA of human, cynomolgus or mouse plasmid) was prepared and added to the cells. (The mammalian expression plasmids were obtained from Sino Biological). Cells were incubated at 37° C., 5% CO2 for 18 h and QCed for human, cynomolgus and mouse PD-L expression by flow cytometry. Briefly, 2.0E+05 of HEK293FF WT, human PD-L1, cynomolgus PD-L1 and mouse PD-L1 cells were incubated with 2.5 µg/ml of anti-human/mouse/cynomolgus (R&D Systems) PD-L1 (goat IgG) in a final volume of 50 µl/well for 30 min, at 49° C. with gentle shaking. Cells were washed 3 times with 150 µl of FACS Buffer (PBS/0.5% FBS) at 300 g for 3 minutes and incubated with the secondary anti-goat Alexa Fluor 647 (ThermoFisher), in a final volume of 50 µl per well, for 30 min at 42° C. with gentle shaking, in the dark. Cells were then washed 3× with 150 µl/well of FACS Buffer and resuspended in 75 µl/well of FACS buffer to be measured in a FACS machine (Accuri C6) in the FL-4 channel (APC channel) and a total of 10000 cells were acquired per sample.

Periplasmic Extract (P.E) Binding to PD-L1 Transfected Cells:

Periplasmic Extract (P.E) from the selected clones were incubated with anti-c-myc antibody, specific to the c-myc tag present in the soluble Fab, for 30 minutes with agitation at room temperature (RT). The mix (P.E+anti-c-myc antibody) was added to the WT or human, cynomolgus and mouse PD-L1 HEK293FF transfected cells and incubated for 60 min at 42° C. with gentle shaking. Cells were then washed 3× with 150 µl/well of FACS buffer and then incubated with 50 µl/well of the secondary antibody goat anti-mouse-APC (ThermoFisher) for 30 min at 4° C., protected from the light, with shaking. Cells were again washed and centrifuged 3× with 150 µl/well of FACS buffer and then resuspended in 75 µl/well of FACS buffer to be measured in the FACS machine (Accuri C6) in the FL-4 channel (APC channel) and a total of 10000 cells were acquired per sample. Several clones bound to human and cynomolgus PD-L1 cells. No mouse PD-L1 binders were found.

Screening of the Selected Clones for PD-1:PD-L1 Inhibition:

PD-L1 cell binding clones were screened for PD-1:PD-L1 inhibition at pH6.0, by ELISA. MaxiSorp™ high protein-binding capacity 96 well ELISA plates, were coated with 1 µg/ml of human PD-1 Fc protein (R&D Systems), diluted in PBS, overnight at 42° C. The next day, plates were washed 3× with CPA Tween 0.05% (pH 6.0) and blocked for 1 hour at room temperature with 250 µl/well of 1% Casein/CPA (pH6.0). After blocking the plates were washed 3× with CPA Tween 0.05% (pH 6.0) and incubated with 50 µl of biotinylated-PD-L1 (2 µg/ml, R&D Systems) in CPA/0.1% Casein+50 µl P.E (1:2.5) in CPA/0.1% Casein for competition, in a final volume of 100 µl, for 1 hour at RT with shaking. Plates were washed 3× with CPA Tween 0.05% (pH 6.0) and 50 µl of Extravidin-HRP (Sigma-Aldrich), diluted 1:2000, in 0.1% casein/CPA (pH 6.0) was added to the wells for detection of the biotinylated human PD-L1 binding to coated PD-1 Fc in the presence of the P.E. Plates were incubated for 1 hour at room temperature. Plates were then washed 3× with CPA Tween 0.05% (pH 6.0) and the substrate solution (TMB) was added to the plates and the reaction was stopped with H2SO4 and the plates read at 450 nm. The ability of the clones to block PD1:PD-L1 interaction was evaluated by comparison of the OD values of the wells having biotinylated-PD-L1 in the presence of relevant and irrelevant P.E. As a control and also for comparison of P.E inhibition effect, neutralising anti PD-L1 antibody was also used in the assay. Four clones; 1E08, 1A06, 2A09 and 2C11 were able to inhibit by 40% to 80% the PD1:PD-L1 interaction. These clones were utilised for BIAcore analysis at pH 6.0 and pH 7.4 after IgG formatting.

Formatting IgG, Production and Purification:

The synthetic genes codifying to the VH, V® and VI antibody variable domains were purchased from invitrogen. Each DNA were reconstituted according to the manufacture instructions. 200 ng of DNA were transformed into E. coli TOP10 chemically competent cells. The DNA purification was performed with the QIAprep Spin Miniprep kit from QIAGEN. Each DNA construct was restriction enzyme digested, the insert was gel purified, and each variable domain insert was ligated with a mammalian expression vector containing the antibody heavy chain constant domains for the VH insert, or the light chain constant domain for the V☐ or V☐ insert. ExpiCHO-S cells were transfected with the clones according to the manufacturer's (ThermoFisher) instructions; 40 µg of total DNA plasmid constructs containing VH and Vk chains were used in a 50 mL total volume of cells, for 4-10 days of protein production (32° C., 5% CO2). Quality Control by SDS-Page after 4 and 10 days of protein production was performed, by analysing the presence of bands at 150 kDa in the non-reduced conditions, and bands at 50 kDa and 25 kDa, corresponding to IgG molecular weights in reducing conditions. The antibodies were purified using Hitrap MabSelect Sure columns on an ÄKTA Pure 25 system. The IgG was subsequently eluted using 0.1 M glycine at pH 2.7 and 1.0 ml fractions were collected in tubes containing 0.1 ml Tris-HCl pH 9.0 for neutralization. Antibody containing fractions were pooled and desalting was performed using a HiTrap desalting column on an ÄKTA Pure and buffer exchanged into 1×PBS (phosphate buffered saline pH 7.4) solution. Preparative size exclusion chromatography was employed to remove aggregates from the protein A fractions. Protein concentration was determined by measuring the absorbance at 280 nm.

Binding of purified antibodies to WT, human, cynomolgus and mouse PD-L1 transfected HEK293FF Transfection of HEK293FF cells with human, cynomolgus and mouse PD-L1 was performed as described above. Briefly, 2×105 HEK293FF WT, human PD-L1, cynomolgus PD-L1 and mouse PD-L1 cells were incubated with the purified anti-PD-L1 IgG1 clones (500 nM to 0.69 nM) in FACS buffer (PBS/0.5% FBS) and incubated with 2×105 of WT or human, cynomolgus and mouse HEK293FF transfected cells in a final volume of 100 µl/well, for 1 hour at 4° C. with gentle shaking. As a control for specificity, an irrelevant antibody was used. After incubation, cells were washed 3 times with 150 µl of FACS buffer and 50 µl/well of anti-human IgG-Fc FITC labelled antibody (ThermoFisher) was added to the cells for 1 hour at 4° C. with gentle shaking. After the cells were washed, they were resuspended in 75 µl/well of FACS buffer and measured in the FACS machine (Accuri C6) in the FL-1 channel (FITC channel) and a total of 10000 cells were acquired per sample.

ELISA Binding to PD-L1 at Different pHs:

Purified anti-PD-L1 IgG1 clones were tested for binding to human PD-L1 at pH 6.0 versus pH 7.4, via binding ELISA. MaxiSorp™ high protein-binding capacity 96 well ELISA plates, were coated with 1 µg/ml of human PD-L1-Fc protein, diluted in PBS, overnight at 49° C. The next day, plates were washed 3× with CPA Tween 0.05% (pH 6.0) or PBS Tween 0.05% (pH7.4) and blocked for 1 hour at room temperature with 250 µl/well of 4% Marvel/CPA (pH6.0) or PBS (pH7.4). After blocking, plates were washed 3× with CPA Tween 0.05% (pH 6.0) or PBS Tween 0.05% (pH7.4) and incubated with 100 µl of serial dilutions of the antibodies (3-fold dilutions; 100 nM-0.137 nM) prepared in 1% Marvel CPA (pH 6.0) or PBS (pH 7.4) and incubated for 2 hours at room temperature (RT) with shaking. Plates were then washed 3× with CPA Tween 0.05% (pH 6.0) or PBS Tween 0.05% (pH 7.4) and 100 µl/well of secondary antibody, anti-human-CH1 specific-HRP (BD Pharmingen cat. no. 555788) prepared in 1% Marvel CPA (pH 6.0) or PBS (pH 7.4) was added and incubated for 1 h at RT with shaking. Plates were washed 3× with CPA Tween 0.05% (pH 6.0) or PBS Tween 0.05% (pH 7.4) and the substrate solution (TMB) added and the reaction stopped with H2SO4 and the plates read at 450 nm. In final screening assays a Krebs ringer bicarbonate buffer (KRB, Amsbio catalog number KRB-1000) with 1 mM lactic acid (Sigma catalog number 252476-500G) for pH 7.4; KRB plus 15 mM lactic acid for pH 6.5 and KRB plus 20 mM lactic acid for pH 6.0) was also used.

Screening Antibodies for PD-1:PD-L2 Inhibition:

Antibodies were screened for PD-1: PD-1 Inhibition at pH 6.0, by ELISA.

MaxiSorp™ high protein-binding capacity 96 well ELISA plates, were coated with 1 µg/ml of human PD-1-Fc protein, diluted in PBS, overnight at 4° C. The next day, plates were washed 3× with CPA Tween 0.05% (pH 6.0) and blocked for 1 hour at room temperature with 250 µl/well of 1% Casein/CPA (pH 6.0). After blocking, plates were washed 3× with CPA Tween 0.05% (pH 6.0) and 3-fold dilutions of the anti-PD-L1 IgG1 clones, starting at 100 nM to 0.05 nM, were incubated for 1 h (RT) with 1 g/ml human PD-L1 biotin in 0.1% casein/CPA (pH 6.0), in a total volume of 100 µl/well. Plates were washed 3× with CPA Tween 0.05% (pH 6.0) and Extravidin-HRP (diluted 1:2000) in 0.1% casein/CPA (pH 6.0) was added to the wells, for detection of the biotinylated human PD-L1 that can bind to coated PD-1-Fc, in the presence of the antibodies. Plates were incubated for 1 hour at room temperature then washed 3× with CPA Tween 0.05% (pH 6.0) and substrate solution (TMB) added and the reaction stopped with H2504 and plates read at 450 nm. The ability of the antibodies to block PD1:PD-L1 interaction was evaluated by comparison of the OD values of the wells having biotinylated-PD-L1 in the presence of an anti-PD-L1 antibody versus an irrelevant antibody. This assay was also performed at pH 6.5 and pH 7.4 substituting PBS for CPA in the above buffers. In final screening assays a Krebs ringer bicarbonate buffer (KRB, Amsbio catalog number KRB-1000) with 1 mM lactic acid (Sigma catalog number 252476-500G) for pH 7.4; KRB plus 15 mM lactic acid for pH 6.5 and KRB plus 20 mM lactic acid for pH 6.0) was also used.

Screening Antibodies for CD80:PDL1 Inhibition

The ELISA assay is the same as the above "Screening antibodies for PD-1:PD-L1 inhibition" except the coating antigen is 1 µg/ml human B7-1-Fc (CD80) (R&D Systems cat. no. 140-B1).

BIAcore Analysis:

To assess the affinity of selected IgG formatted purified clones to human PD-L1 at pH6.0 and at pH7.4, human PD-L1-Fc protein was coated by amine coupling. Surface plasmon resonance (SPR) (BIAcore 3000, GE Healthcare) was used to determine the binding kinetics of selected IgG formatted purified clones to human PD-L1 at pH6.0 and at pH 7.4. Approximately 3000 RU of human PD-L1 Fc (R&D Systems) at 50 µg/ml in Acetate buffer pH 5.0 was immobilized onto a CM5 chip using the standard amine coupling procedure. QC of the PD-L1 immobilization was performed using an anti-PD-L1 commercial antibody (R&D systems cat. no. AF156) at 2.0 µg/ml. 1×HBS-EP pH 7.4 or HBS-EP pH 7.0 or HBS-EP 10 nM citrate buffer pH 6.5 or HBS-EP 10 nM citrate buffer pH 6.0, were utilized as running buffers during binding kinetic measurements. Antibody gradients were comprised of 3-fold dilutions, starting from 50 nM to 0.13 nM in relevant pH buffers and were injected for 120 s at a flow rate of 30 µl/min. After dissociation, regeneration of the PD-L1-Fc surface was achieved with 10 mM NaOH in 1 M NaCl (30 s injection at 20 µl/min) followed by a single 30 s injection at 20 µl/min of 10 mM glycine pH 1.5. Fitting 1:1 binding with mass transfer was applied to the curves using the BIAevaluation software to calculate the kinetic constants of the antibody-antigen interactions including association rate (ka), dissociation rate (kd) and affinity ($K_D$).

Affinity Maturation Library Generation:

The construction of the phage display libraries was generated by gene assembly. Overlapping oligonucleotides and/ or trimers containing specific mutations at certain positions as defined in the library design were used to synthetically generate the V-genes via PCR. The oligonucleotides were designed to assemble the complete VH and Vλ sequence, with primers specific for the HCDR1, HCDR2, HCDR3 or LCDR1, LCDR2, LCDR3 regions containing either the parental nucleotides or the degenerate codon to allow the construction of the different variants. Coning restriction sites were introduced into the VH and Vλ genes, for further insertion into a phagemid vector. All gene assembly PCRs were performed using three different annealing temperatures and PCR products pooled if no difference between the different annealing temperature PCR products was observed. The gel-purified Vλ genes were cloned into the pCB13_2A09VH_WT phagemid vector that contains the constant human heavy and Light genes (CH and CL) and the parental VH chain domain, for construction of the AFF2A09_LCDR1, AFF2A09_LCDR2 and AFF2A09_LCDR3 affinity maturation libraries. The gel-purified VH randomized genes, were cloned into the pCB13_2A09Vλ_WT phagemid vector that contains the CH and CL human constant regions and the parental Vλ domains, for construction of the AFF2A09_HCDR1, AFF2A09_HCDR2 and AFF2A09_HCDR3 affinity maturation libraries. All Fab phage display libraries had more than 80% of transformants containing full Fab insert and 48 transformants per library were sent for sequencing and analyzed for amino-acid frequency introduction in the target Heavy and Light CDR, as compared to the WT sequences of the parental clone 2A09.

Affinity Maturation Phage Display Selections:

Round I: panning selections. A first round of panning selections using 2A09 affinity maturation sub-libraries to select Fabs against human PD-L1, at pH 6.0 was performed. Plates were coated with 10 μg/ml human PD-L1 in 1×PBS, 100 μl/well, O/N, 4 C, followed by blocking with 250 μl/well 4% Skimmed Milk (Marvel, cat no. 928964) in PBS for 2 h, at RT. Phages from the 2A09 affinity maturation sub-libraries were blocked in 4% Skimmed Milk/CPA pH 6.0 per selection condition, for 30 min at RT, with rotation. 50 μl of phage from the affinity maturation sub-libraries in 4% Skimmed Milk/1×PBS per selection condition, were incubated in the plates coated with antigen, for 2 h, RT; 100 μl/well. After incubation, wells were washed 15 times with 1×CPA-Tween 0.05% including 5 min shaking incubations every fifth wash plus 5 times wash with 1×CPA pH 6.0; 250 μl/well. 1 mg/ml of trypsin (Sigma, cat. no. T1426-5G), was used to perform total elution of the phages bounded to PD-L1. 150 μl per well of Trypsin was added and incubated for 20 min, RT. Inhibition of trypsin protease activity was performed with 10 μl AEBSF (Sigma, cat. no. A8456). Serial dilutions of the eluted phages were performed and used to infect exponentially growing TG1. Infected TG1 was plated on LBCarb100Glu2% plates and enrichments were calculated as the ratio between the number of phages eluted from the antigen selection conditions over the number of phage eluted from no antigen selection condition. Good enrichments were observed for all sub libraries and outputs were taken for a second round in solution.

Round II: affinity-driven in solution selections. A second round was performed, using biotinylated PD-L1 and streptavidin-coated magnetic beads for selection of affinity matured Fab against PD-L1 that recognize the antigen in solution. Antigen blocking: biotinylated PD-L1 at 10 nM and 1 nM was blocked with 2% Marvel CPA buffer pH6.0, for 30 minutes, RT, with rotation. Phage blocking: 10 μl of input phage from outputs coming from the 1st round were blocked with 4% Marvel CPA buffer (per condition) for 30 minutes, at RT with rotation. Phage+antigen mix: 100 μl blocked antigen (bio-PD-L1)+100 μl blocked phage (per condition) were incubated for 2 hours, RT, with rotation. Beads wash/blocking: 30 μl Dynabeads' MyOne™ Streptavidin T1 Magnetic Beads (Invitrogen, cat. no. 65601) per selection condition were washed 3 times with CPA buffer-Tween 0.05% and blocked in 2% Marvel CPA buffer for 30 minutes, RT, with rotation. Mix Phage+Antigen beads capturing: 200 μl of the mix (phage+antigen bio-PD-L1) was added to the magnetic beads, for 15 minutes, at RT, with rotation. After incubation, beads were washed 5 times with CPA buffer-Tween 0.05% plus a 2 times wash with 1 ml CPA buffer. Elution: Total elution of phages bound to PD-L1 was performed using 1 mg/ml of Trypsin, 200 μl/condition; 20 minutes, RT, with rotation. Inhibition of trypsin protease activity was performed with 10 μl AEBSF. Enrichments: Serial dilutions of the eluted phages were performed and used to infect exponentially growing TG1. Infected TG1 was plated on LBCarb100Glu2% plates and enrichments during recombinant protein selections were calculated as the ratio between the number of phages eluted from the antigen selection conditions over the number of phage eluted from no antigen selection condition.

Round 3: affinity-driven in solution selections with off-rate wash of 2 hours or 20 hours. To select Fabs affinity matured against PD-L1 that recognize the antigen in solution were performed using a third round of in-solution selections using streptavidin-coated magnetic beads with off-rate washing using a 100-fold excess of non-biotinylated PD-L1 for 2 hours or 20 hours, in order to select for high affinity clones. Antigen blocking: Biotinylated PD-L1 at 1 nM, 0.1 nM, 0.01 nM and 0 nM was blocked with 2% Marvel i CPA buffer pH6.0, for 30 minutes, RT, with rotation. Phage blocking: 10 μl of input phage from outputs coming from the 2nd round were blocked with 4% Marvel in CPA buffer (per condition); for 30 minutes, at RT with rotation. Phage+Antigen mix: 100 μl blocked antigen (bio-PD-L1)+100 μl blocked phage (per condition) were incubated for 2 hours, RT, with rotation. Beads wash/blocking: 30 μl Dynabeads™ MyOne™ Streptavidin T1 Magnetic Beads (Invitrogen, cat. no. 65601) per selection condition were washed 3 times with CPA buffer-Tween 0.05% and blocked in 2% Marvel CPA buffer, for 30 minutes, RT, with rotation. Mix Phage+Antigen beads capturing: 200 μl of the mix (phage+antigen bio-PD-L1) was added to the magnetic beads, for 15 minutes, at RT, with rotation. After incubation, beads were washed 5 times with CPA buffer-Tween 0.05% plus a 2 times wash with CPA buffer. Off-rate wash: 100-fold excess of non-biotinylated PD-L1 (10 nM, 1 nM and 0.1 nM) or CPA buffer was added to the selection wells and incubated for 2 or 20 hours, at RT, with rotation. Elution: Total elution of phages bound to PD-L1 was performed using 1 mg/ml of Trypsin, 200 μl/condition, for 20 minutes at RT, with rotation. Inhibition of trypsin protease activity was performed with 10 μl AEBSF. Enrichments: Serial dilutions of the eluted phages were performed and used to infect exponentially growing TG1. Infected TG1 was plated on LBCarb100Glu2% plates and enrichments during recombinant protein selections were calculated as the ratio between the number of phages eluted from the antigen selection conditions over the number of phage eluted from no antigen selection condition. Outputs selected with 1 nM of biotinylated PD-L1 and off-rate wash using 100 nM of PD-L1 for 2 h or 20 h, were taken for a round IV selection in cells.

Round 4: cell selections. To select affinity matured Fab against native PD-L1, present in the cell surface, was performed using rounds of selections with MDA-MB-231 cells (endogenous cells expressing PD-L1), at pH 6.0. Cells: Per sublibrary condition, 5.0E+06 MDA-MB-231 cells in 10% FBS/PBS pH6.0 (acidified with 1M HCL) were used. Cells were also QCed for PD-L1 expression, by incubating with 300 nM; 100 nM; 33.3 nM; 11.1 nM; 3.70 nM; 1.23 nM; 0 nM of mAb 2A09 or mAb 12A4 (from U.S. Pat. No. 9,856,320) in FACS Buffer at pH7.4 or pH6.0, for 1 h at 4° C. with shaking and using a secondary antibody (Alexa Fluor™ 488 AffiniPure Mouse Anti-Human IgG; Jackson ImmunoResearch Laboratories cat. No. 209-545-098) for detection. Phage blocking: Per sublibrary, output phages coming from the round 3 selection (off-rate wash, 100 nM PD-L1, for 2 h or 20 h) were pooled and blocked with 10% FBS/PBS pH6.0 for 20 minutes, 4° C., with rotation. Phage+ cells: 5E+06 MDA-MB-231 cells per condition were resuspended with the blocked phage and incubated for 2 hours, 4° C., with rotation. After incubation, cells were washed 4 times with 10% FBS/PBS pH 6.0 plus 1 wash with PBS pH 6.0; 1 ml per wash. Elution: Total elution of phages bound to PD-L1 was performed using 1 mg/ml of Trypsin, 200 µl/condition, for 20 minutes at RT, with rotation and inhibition of trypsin protease activity with 10 µl AEBSF. Enrichments: Serial dilutions of the eluted phages were performed and used to infect exponentially growing TG1. Infected TG1 was plated on LBCarb100Glu2% plates and enrichment values calculated over the background (without antigen for selection).

The HCDR1 and 2 libraries and LCDR3 library produced no significant hits compared to the 2A09 WT. The HCDR3 library produced 1 predominant hit and 3 other unique sequences isolated with improved binding compared to 2A09 while the LCDR1 library produced 36 unique hits and the LCDR2 library 6 unique hits with improved binding.

These hits were further analysed by cell binding assay, BIAcore assay and PD-L1 neutralization assays at pH 6 and pH 7.4 as described above.

Lead Fabs were prepared by Pierce™ Fab Preparation Kit (cat. no. 44985) from purified IgG as described above.

Binding of Anti-PD-L1 mAbs or Fabs to MDA-MB-231 Cells in a Tumor-Like Buffer

In order to mimic an acidic tumor environment milieu with tumor cells expressing PD-L1 (The metabolism of tumors in the body, Warburg et al. J Gen Physiol. 1927; 8:519-30) the following buffers were utilised: Krebs ringer bicarbonate buffer (KRB, Amsbio catalog number KRB-1000) with 1 mM lactic acid (Sigma catalog number 252476-50DG) for pH 7.4; KRB plus 15 mM lactic acid for pH 6.5 and KRB plus 20 mM lactic acid for pH 6.0). 3 fold dilutions (100 nM to 0.0005 nM; 0) of the Fabs or IgG were prepared in the respective pH buffers and incubated with 0.60E05 MDA-MB-231 cells for 60 minutes at 4° C. The cells were then washed 3× with the respective pH buffers, at 300 g for 3 min. The cells were then incubated with 50 µl of anti-human IgG (Fab specific)-FITC (Sigma, catalog number F5512-1ML) at 1:100 dilution in the respective pH buffers. Binding of the IgG or Fab to PD-L1 expressing cells was measured by FACS (Attune Nxt) and a total of 10.000 cells were acquired per sample.

Statistical Analysis

GraphPad Prism 7 software (GraphPad 50 Software, Inc., La Jolla, CA, USA) was used for analysis of IC50, EC50 and statistical analysis.

Results

Figure 1B:
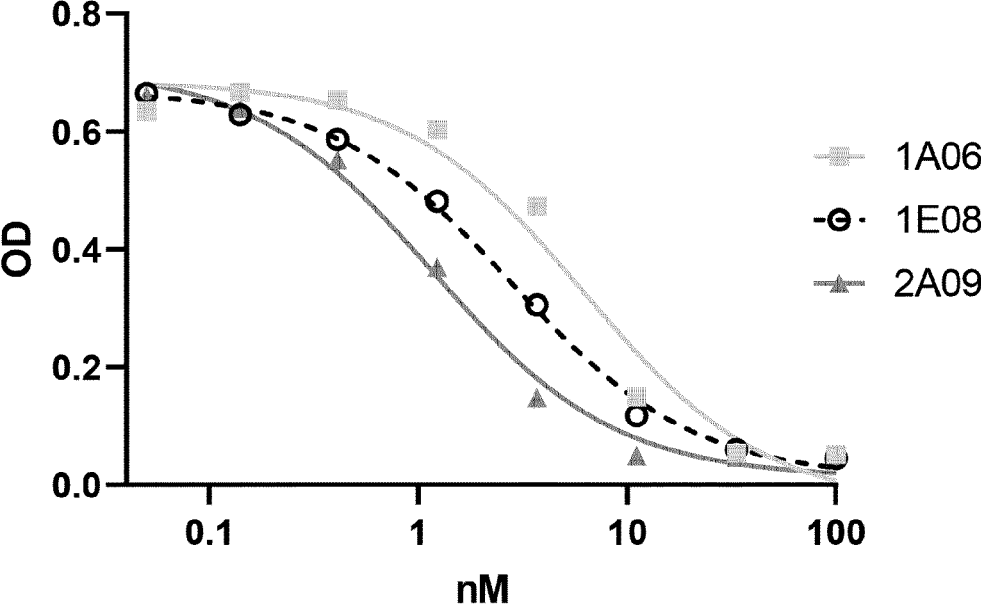
FIG. 1B shows the results of a CD80 neutralising ELISA of the three lead mAbs 1A06, 1E08 and 2A09.

The initial screening cascade of the Fab library were phage ELISAs at pH 6 against human and cynomolgus PD-L1 followed by a PD-L1-PD-1 inhibition ELISA and binding to PD-L1 positive cells (MDA-MB-231). 20 clones from different families that were positive from those assays were rescreened as a P.E. Fab preparations at pH 6 in ELISAs against human and cynomolgus PD-L1 followed by a PD-L1-PD-1 inhibition ELISA and the cell binding assay in MDA-MB-231 cells. From these screens it was found that 16 clones bound both as phage and P.E to human and cynomolgus cells; 7 had weak neutralizing activity and 4 Fabs were selected that had high neutralising activity. Two of these clones had identical CDRs so three Fabs were converted to IgG for further analysis. All three mAbs inhibited PD-L1 binding to PD-1 by ELISA (FIG. 1A) with IC50 values calculated from FIG. 1A for 2A09, 0.4 nM; 1A06, 0.9 nM and 1E08, 1.1 nM. All 3 mAbs also inhibited PD-L1 binding to CD80 by ELISA as shown in FIG. 1B with IC50 values calculated from FIG. 1B for 2A09, 1.2 nM; 1A06, 6.3 nM and 1E08, 2.8 nM. mAb 2A09 also showed equivalent binding to human and cynomolgus PD-L1.

The Fab sequence of 2A09 is shown in Table 4.

TABLE 4

VH and VL sequence of lead Fab 2A09.
The CDRs are underlined.

| Fab | VH |
|---|---|
| 2A09 | QVQLVQSGGGVVQPGRSLRLSCAASGFTFSSYGMYWVRQAPGKG LEWVAVISYDGSNKYYADSVKGRFTISRDNSKNTLNLQMNSLRA EDTAVYYCAKGALTHWGVVIGDGMDVWGQGTTVTVSS (SEQ ID NO: 5) |

| Fab | VL |
|---|---|
| 2A09 | NFMLTQPHSVSESPGKTVTISCTRSSGSIASNYVQWYQQRPGSS PTTVIYEDDQRPSGVPDRFSGSIDSSSNSASLTISGLKTEDEAD YYCQSFDSTNPWVFGGGTKLTVL (SEQ ID NO: 1) |

Figure 2:
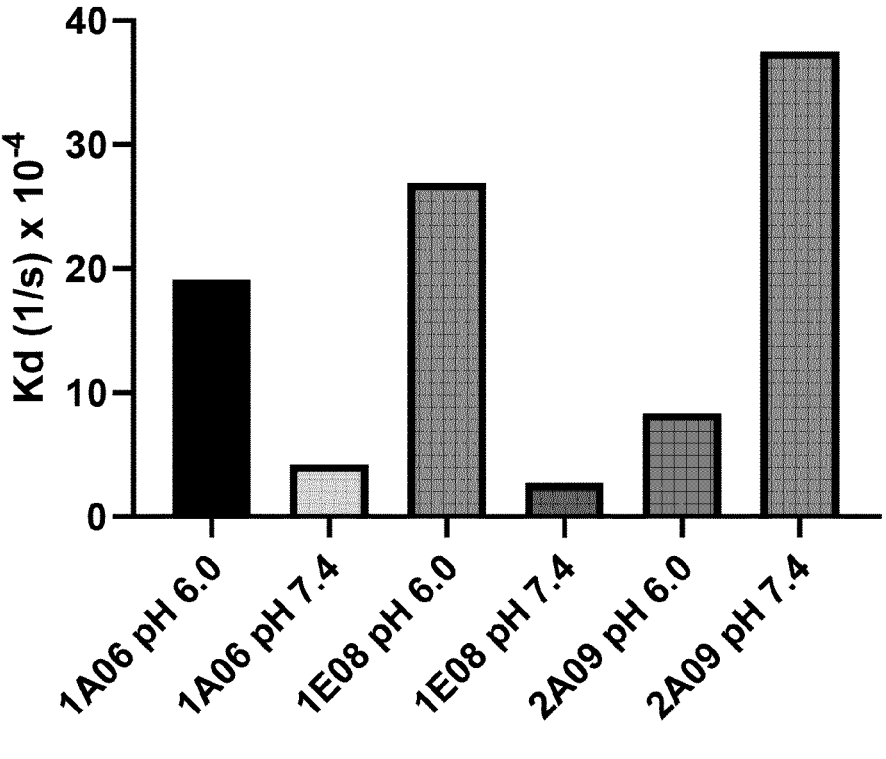
FIG. 2 shows the results of BIAcore analysis of anti-PD-L1 mAbs. Kd (1/s) of mAbs 2A09, 1A06 and 1E08 at pH 6.0 and pH 7.4 binding to PD-L1-Fc.

Initial analysis of the off rate by BIAcore (FIG. 2) revealed that two of the mAbs (1A06 and 1E08) had preferential binding to PD-L1 at pH 7.4 as shown by lower Kd values at this pH compared to pH 5. In complete contrast, mAb 2A09 had better binding to PD-L1 at pH 6.0 with an approximate 5-fold better off rate. The BIAcore analysis was repeated with a wider range of pH's and compared to the anti-PD-L1 mAb 12A4 (from U.S. Pat. No. 9,856,320) and the results depicted in Table 5.

mAb 2A09 showed an approximate 20 fold higher affinity at pH 6 compared to pH 7.4 which is in complete contrast to mAb 12A4, which was not selected for pH specific binding and in fact shows lower affinity at pH 6 compared to pH 7.4.

TABLE 5

BIAcore kinetic analysis of mAb 2A09 binding to PD-L1. Anti-PD-L1 mAbs, 2A09 and 12A4 (positive control) were injected over immobilised PD-L1-Fc and the kinetics determined by BIAevaluation software.

| mAb | pH | Ka (1/Ms) | Kd (1/s) | $K_D$ (nM) |
|---|---|---|---|---|
| 2A09 | 7.4 | $1.05 \times 10^7$ | $2.71 \times 10^{-2}$ | 2.6 |
| 2A09 | 7.0 | $1.25 \times 10^7$ | $7.11 \times 10^{-3}$ | 0.57 |
| 2A09 | 6.5 | $7.36 \times 10^6$ | $1.29 \times 10^{-3}$ | 0.18 |
| 2A09 | 6.0 | $6.77 \times 10^6$ | $8.65 \times 10^{-4}$ | 0.13 |
| 12A04 | 7.4 | $4.02 \times 10^6$ | $2.25 \times 10^{-5}$ | 0.006 |
| 12A04 | 7.0 | $3.72 \times 10^6$ | $2.39 \times 10^{-5}$ | 0.006 |
| 12A04 | 6.5 | $3.95 \times 10^6$ | $4.62 \times 10^{-5}$ | 0.01 |
| 12A04 | 6.0 | $4.76 \times 10^6$ | $1.21 \times 10^{-4}$ | 0.03 |

Figure 3:
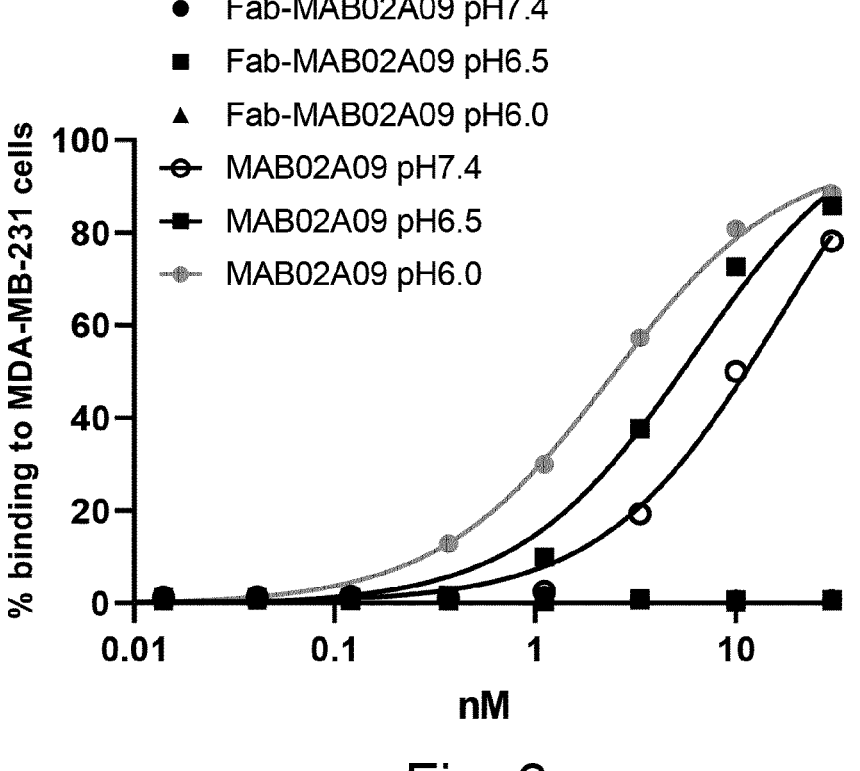
FIG. 3 shows the binding of 2A09 mAbs and Fabs to MDA-MB-231 cells at pH 7.4, 6.5 and 6.0. In Krebs buffer.

Although the data presented in Table 5 does reflect a pH dependence of binding there is an avidity component of binding of the mAb to PD-L1 on the BIAcore surface. In order to circumvent this issue and analyse the binding of 2A09 to cells in a buffer resembling the tumor microenvironment, PD-L1 expressing MDA-MB-231 cells were incubated with 2A09 mAb and Fab at pH 6, 6.5 and 7.4 in a Krebs buffer with lactate (FIG. 3). The EC50 of 2A09 binding to PD-L1 was calculated from FIG. 3 and was 16.3 nM at pH 7.4; 6.1 nM at pH 6.6 and 2.4 nM at pH 6.0. Under these conditions the Fab of 2A09 had very little binding activity (FIG. 3).

As a result of the low affinity of the 2A09 Fab, an affinity maturation campaign of this clone was undertaken. A screening campaign as outlined above for 2A09 was performed and 5 Fab affinity matured leads were selected that showed pH dependence of binding and increased affinity over the parental 2A09 clone, binding to PD-L1 (Table 6). All 5 leads were selected encompassing mutations in CDR1 of the light chain.

TABLE 6

Analysis of unpurified affinity matured anti-PD-L1 Fabs (periplasmic extract) by BIAcore off rate analysis.

| Clone | Library | Kd (s−1) pH 7.4 | Kd (s−1) pH 6 | Ratio pH 6 vs 7.4 |
|---|---|---|---|---|
| 8G08 | LCDR1 | 3.08E−03 | 8.23E−04 | 27 |
| 8D06 | LCDR1 | 3.45E−03 | 6.99E−04 | 20 |
| 8A04 | LCDR1 | 1.50E−02 | 1.31E−03 | 9 |
| 8D04 | LCDR1 | 2.75E−02 | 2.83E−03 | 10 |
| 8B06 | LCDR1 | 1.05E−02 | 1.35E−03 | 13 |
| 2A09 WT | | ND | ND | |

Figure 4:
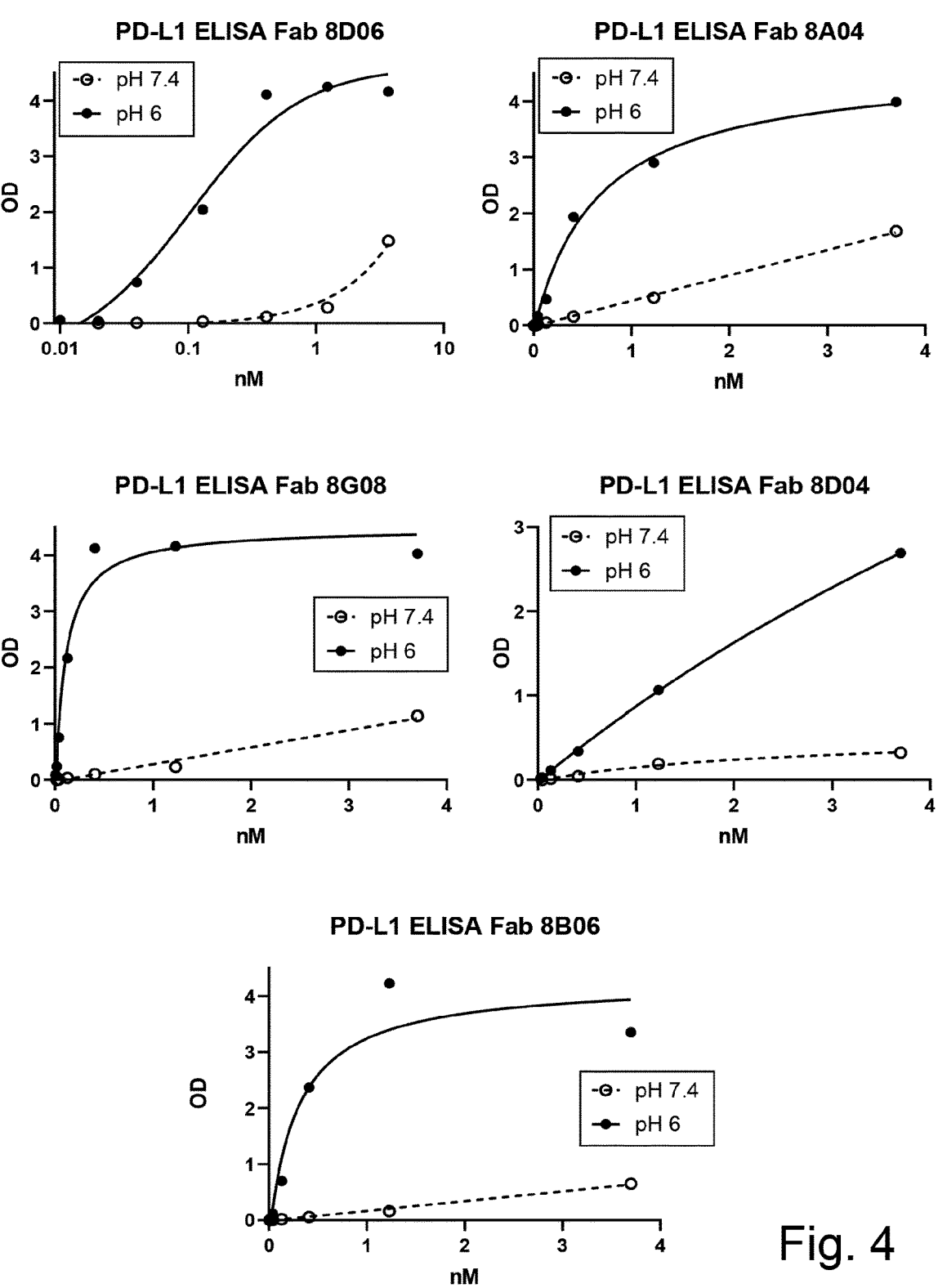
FIG. 4 shows affinity matured anti-PD-L1 Fabs binding to PD-L1 by ELISA at pH 7.4 and pH 6.0 in KRB buffer.

All 5 selected Fabs were purified and initially examined by ELISA (FIG. 4). All Fabs showed pH specific binding and a positive control anti-PD-L1 Fab or mAb 2.7A04OPT (from patent WO2011066389) showed no pH dependence binding. A negative control Fab (2A11, anti-HEL) showed no specific binding. This initial assay demonstrated by ELISA that the Fabs have far greater affinity at pH 6 (Table 7) and weak non-saturable binding at pH 7.4 over the concentrations examined. An EC50 could not be measured accurately by this methodology at pH 7.4, however, a ratio of binding is shown in Table 7 demonstrating that the Fabs bind 9-53 times better at pH 6 when comparing an OD reading that is on both pH curves. At pH 6 all the Fabs reached saturation of binding at 4 nM while none of the 5 Fabs reached saturation at pH 7.4 in this assay (FIG. 4).

TABLE 7

EC50 calculation of affinity matured Fabs binding to PD-L1 by ELISA from FIG. 4.
The ratio of binding was calculated by extrapolating an OD of 0.3 from the standard curve of the Fab at pH 6 versus pH 7.4

| | 8D06 | 8A04 | 8G08 | 8D04 | 8B06 |
|---|---|---|---|---|---|
| pH 6, EC50, nM | 0.11 | 0.54 | 0.10 | 2.63 | 0.31 |
| pH 7.4, EC50, nM | >10 | >10 | >100 | >100 | >100 |
| Ratio pH 6:7.4 | 39 | 11 | 53 | 9 | 38 |

Anti-PD-L1 affinity matured Fabs were tested for their inhibitory activity in a PD-L1 inhibition ELISA at pH 6.0, 6.5 and 7.4 (FIG. 5). In this assay the anti-PD-L1 Fab2.7A040PT was used as a positive control and Fab 2A11 as a negative control. The IC50 was calculated from the curves and depicted in Table 8. The IC50 of inhibition of PD-L1 binding to PD-1 with the anti-PD-L1 Fabs 8D06, 8A04, 8G08 and 8B06 at pH 6 is only approximately 3 times less than the control Fab 2.7A040PT. At pH 6, 6.5 and 7.4 the anti-PD-L1 Fab 2.7A040PT shows no pH preference for inhibition. This is in complete contrast to the Fabs of this invention which show a clear pH dependence of inhibition (FIG. 5 and Table 8). The Fabs 8D06, 8A04, 8G08 and 8B06 have approximately 3 fold less inhibitory activity at pH 6.5 compared to pH 6 and very little activity at pH 7.4. Anti-PD-L1 Fab 8D04 is approximately 3 fold less potent than Fabs 8D06, 8A04, 8G08 and 8B06 by this assay. It is important to note that at 100 nM, none of the Fabs completely inhibited PD-L1 binding to PD-1 at pH 7.4, the best being Fab 8A04 with approximately 60% inhibition (FIG. 5).

TABLE 8

IC50 calculation of affinity matured Fabs inhibiting PD-L1:PD-1 binding by ELISA from FIG. 5.
A negative control Fab (2A11, anti-HEL) showed no inhibition and Fab 2.7A04OPT (from patent WO2011066389) was used as the positive control.

| | 8D06 | 8A04 | 8G08 | 8D04 | 8B06 | 2.7A04OPT |
|---|---|---|---|---|---|---|
| pH 6, IC50 nM | 13.1 | 12.2 | 12.1 | 42.3 | 15.7 | 5.4 |
| pH 6.5, IC50 nM | 40.0 | 29.4 | 41.6 | >100 | 52.7 | 4.9 |
| pH 7.4, IC50 nM | >100 | 81.2 | >100 | >100 | >100 | 6.8 |
| Ratio pH 6:7.4 | >7.63 | 6.66 | >8.26 | >2.36 | >6.37 | 1.26 |

Figure 6:
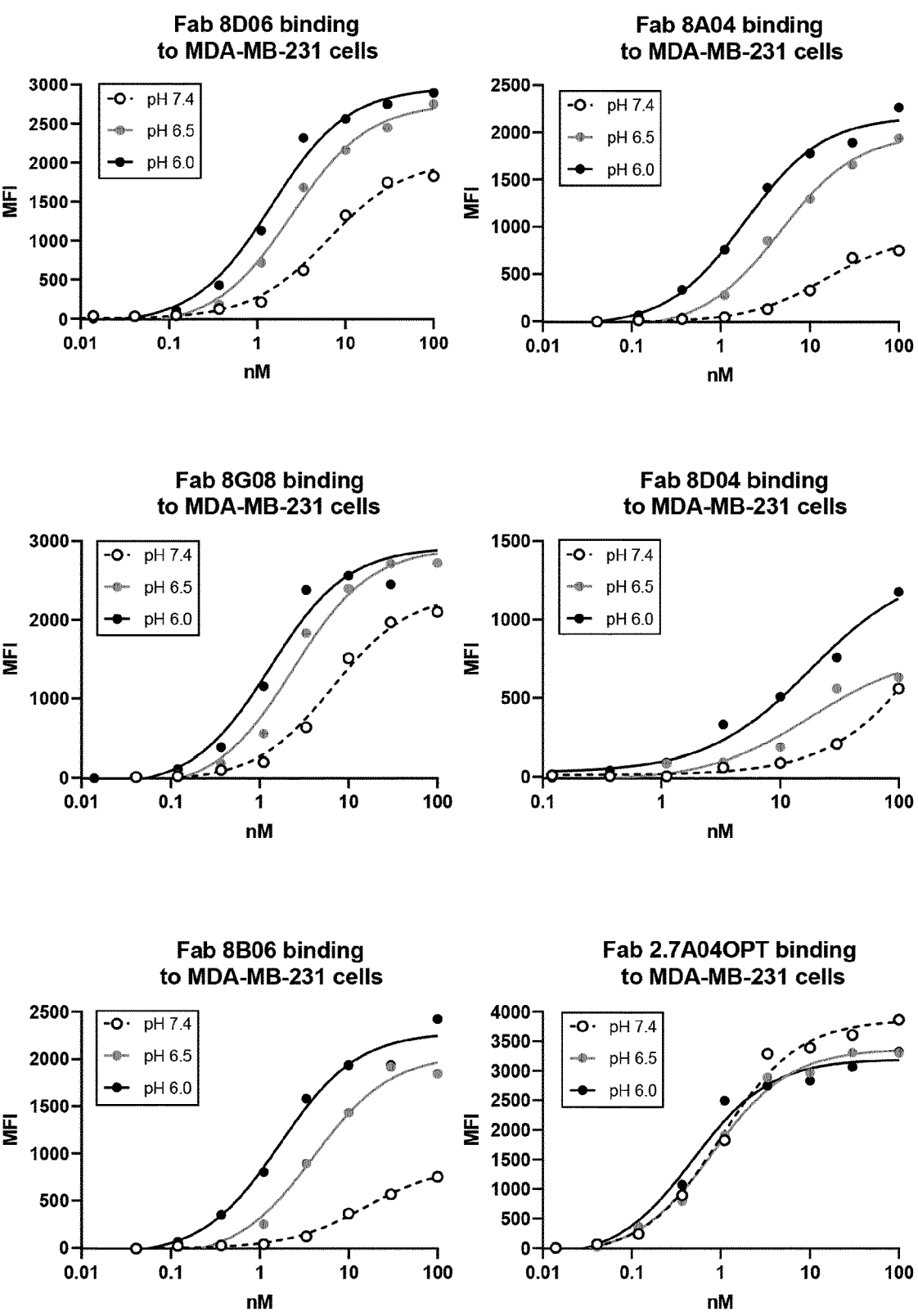
FIG. 6 shows affinity matured anti-PD-L1 Fabs binding to MDA-MB-231 cells at pH 7.4, 6.5 and 6.0. mAb in Krebs buffer. Anti-PD-L1 Fab 2.7A04OPT was used as a positive control.

Anti-PD-L1 affinity matured Fabs were tested for their ability to bind to native PD-L1 in a cell line, (MDA-MB-231 cells) in a buffer resembling the tumor microenvironment (Krebs-lactate). Again, all 5 affinity matured Fabs showed pH dependent binding (FIG. 6 and Table 9A). The positive control anti-PD-L1 Fab 2.7A040PT showed no pH binding preference. The pH binding preference ranged from 8 fold (Fab 8G08) and 11 fold (Fab 8D06) to over 100 fold (Fabs 8A04, 8D04 and 8B06). For all Fabs the total binding (MFI) at pH 7.4 and 100 nM Fab was far less than at pH 6 and did not reach saturation. The Fabs were also formatted into an IgG1 and binding to MDA-MB-231 cells at pH 7.4, 6.5 and 6.0 was investigated (Table 9B). Surprisingly, the mAbs showed no pH dependence of binding (Table 96). The pH dependence of binding is related to the format (Fab, monomeric binder); the affinity, as the EC50 binding of the Fab is approximately 100 fold less than the mAb and introduction of histidine residues into the CDRs (Table 10).

TABLE 9A

Comparison of affinity matured anti-PD-L1 Fabs binding to MDA-MB-231 cells at pH 7.4, 6.5 and 6.0 in Krebs buffer. Anti-PD-L1 Fab 2.7A04OPT (from patent WO2011066389) was used as a positive control and no specific binding was observed for the negative control Fab (2A11, anti-HEL). The EC50 is presented as 50% of the 0 nM Fab MFI readout at pH 6 to compare all curves.

|  | 8D06 Fab | 8A04 Fab | 8G08 Fab | 8D04 Fab | 8B06 Fab | 2.7A04OPT Fab |
|---|---|---|---|---|---|---|
| pH 6, EC50 nM | 1.45 | 2.16 | 1.58 | 13.5 | 2.0 | 0.82 |
| pH 6.5, EC50 nM | 2.92 | 6.62 | 2.95 | 56.4 | 6.4 | 0.86 |
| pH 7.4, EC50 nM | 16.0 | >100 | 13.2 | >100 | >100 | 0.60 |
| Ratio pH 6:7.4 | 11.0 | >46.3 | 8.35 | >7.41 | >50.0 | 0.73 |

TABLE 9B

Comparison of affinity matured anti-PD-L1 mAbs binding to MDA-MB-231 cells at pH 7.4, 6.5 and 6.0. Anti-PD-L1 mAb 2.7A04OPT (from patent WO2011066389) was used as a positive control and no specific binding was observed for the negative control mAb (2A11, anti-HEL). The EC50 was calculated using GraphPad Prism software.

|  | 8D06 mAb | 8A04 mAb | 8G08 mAb | 8D04 mAb | 8B06 mAb | 2.7A04OPT mAb |
|---|---|---|---|---|---|---|
| pH 6, EC50 nM | 0.11 | 0.09 | 0.08 | 0.11 | 0.14 | 0.07 |
| pH 6.5, EC50 nM | 0.11 | 0.11 | 0.07 | 0.13 | 0.17 | 0.09 |
| pH 7.4, EC50 nM | 0.08 | 0.09 | 0.09 | 0.10 | 0.12 | 0.10 |

Proton-linked binding events play an important role in biological regulation, which includes, for example: the Bohr effect in haemoglobin (Perutz M F et al. J Mol Biol. 1980; 138:649-68); the pH-dependent binding of serine protease inhibitors (Ascenzi P. et al. J Mol Recognit. 1991, 4:113-9); human prolactin which is reported to display a large decrease in binding affinity for its receptor, over a small pH drop from pH 8 to 6.7 (Kulkami M V et al. J Biol Chem. 2010; 285:38524-33). A highly pH-dependent binding event would require multiple ionizable residues (e.g. histidine) and that these may be introduced successfully by the screening methodology used in the methodology described herein. Imidazole forms the side chain of histidine and its pK ($\approx$6.0) is within the physiological pH range as well as the protonated and the nonprotonated forms of imidazole are chemically very different. The nonprotonated form has a hydrophobic and aromatic character whereas the protonated form is hydrophilic and positively charged. Therefore, the chemical interactions differ significantly at pH above or below the pK. At pH 7.0 the nonprotonated form is dominant and favours interactions with other hydrophobic groups and at pH 5.0 the imidazole group is protonated and prefers a hydrophilic environment.

The HCDR1, 2 and 3 and LCDR2 and 3 sequences in the five affinity matured anti-PD-L1 Fabs are the same as the wild type 2A09 Fab. There is only 1 His residue in HCDR3, which may explain the poor pH sensitivity of this clone. The five affinity matured anti-PD-L1 Fabs have 1 or 2 additional His residues in the CDR1 sequence (Table 10) and the VL and VH sequences are depicted in Table 11.

The additional pH specificity and affinity may in part be due to the selection of clones with additional His residues in LCDR1 that can interact with the PD-L1 epitope and produce a "pH-switch".

TABLE 10

Comparison of the LCDR1 sequences of the affinity matured anti-PD-L1 Fabs to the WT 2A09 clone.

| Library | Fab clone | LCDR1 |
|---|---|---|
|  | 2A09 WT | TRSSGSIASNYVQ (SEQ ID NO: 2) |
| LCDR1 | 8G08 | ISNDVPASGHYHR (SEQ ID NO: 10) |
| LCDR1 | 8D06 | VLSPRTHAGHYYR (SEQ ID NO: 12) |
| LCDR1 | 8A04 | MRTGTGNKGHYTR (SEQ ID NO: 14) |
| LCDR1 | 8B06 | RETELSRRLHYVR (SEQ ID NO: 16) |
| LCDR1 | 8D04 | RGTGSSFHHKYVR (SEQ ID NO: 18) |

TABLE 11

Comparison of the VH and VL sequences of the affinity matured anti-PD-L1 Fabs. The HCDR1, 2 and 3 and LCDR 1, 2 and 3 regions are underlined.

| Fab clone | VH sequence | VL sequence |
|---|---|---|
| 8G08 | QVQLVQSGGGVQPGRSLRLSCAASGFTFSSYGMYWVR QAPGKGLEWVAVISYDGSNKYYADSVKGRFTISRDNSKNT LNLQMNSLRAEDTAVYYCAKGALTHWGVVIGDGMDVW GQGTTVTVSS (SEQ ID NO: 5) | NFMLTQPHSVSESPGKTVTISCISNDVPASGHYHR WYQQRPGSSPTTVIYEDDQRPSGVPDRFSGSIDSSS NSASLTISGLKTEDEADYYCQSFDSTNPWVFGGGTK LTVL (SEQ ID NO: 9) |
| 8D06 | QVQLVQSGGGVVQPGRSLRLSCAASGFTFSSYGMYWVR QAPGKGLEWVAVISYDGSNKYYADSVKGRFTISRDNSKNT LNLQMNSLRAEDTAVYYCAKGALTHWGVVIGDGMDVW GQGTTVTVSS (SEQ ID NO: 5) | NFMLTQPHSVSESPGKTVTISCVLSPRTHAGHYYR WYQQRPGSSPTTVIYEDDQRPSGVPDRFSGSIDSSS NSASLTISGLKTEDEADYYCQSFDSTNPWVFGGGTK LTVL (SEQ ID NO: 11) |

TABLE 11-continued

Comparison of the VH and VL sequences of the affinity matured anti-PD-L1 Fabs.
The HCDR1, 2 and 3 and LCDR 1, 2 and 3 regions are underlined.

| Fab clone | VH sequence | VL sequence |
|---|---|---|
| 8A04 | QVQLVQSGGGVVQPGRSLRLSCAASGFTFSSYGMYWVR QAPGKGLEWVAVISYDGSNKYYADSVKGRFTISRDNSKNT LNLQMNSLRAEDTAVYYCAKGALTHWGVVIGDGMDVW GQGTTVTVSS (SEQ ID NO: 5) | NFMLTQPHSVSESPGKTVTISCMRTGTGNKGHYTR WYQQRPGSSPTTVIYEDDQRPSGVPDRFSGSIDSSS NSASLTISGLKTEDEADYYCQSFDSTNPWVFGGGTK LTVL (SEQ ID NO: 13) |
| 8B06 | QVQLVQSGGGVVQPGRSLRLSCAASGFTFSSYGMYWVR QAPGKGLEWVAVISYDGSNKYYADSVKGRFTISRDNSKNT LNLQMNSLRAEDTAVYYCAKGALTHWGVVIGDGMDVW GQGTTVTVSS (SEQ ID NO: 5) | NFMLTQPHSVSESPGKTVTISCRETELSRRLHYVRW YQQRPGSSPTTVIYEDDQRPSGVPDRFSGSIDSSSN SASLTISGLKTEDEADYYCQSFDSTNPWVFGGGTKL TVL (SEQ ID NO: 15) |
| 8D04 | QVQLVQSGGGVVQPGRSLRLSCAASGFTFSSYGMYWVR QAPGKGLEWVAVISYDGSNKYYADSVKGRFTISRDNSKNT LNLQMNSLRAEDTAVYYCAKGALTHWGVVIGDGMDVW GQGTTVTVSS (SEQ ID NO: 5) | NFMLTQPHSVSESPGKTVTISCRGTGSSFHHKYVR WYQQRPGSSPTTVIYEDDQRPSGVPDRFSGSIDSSS NSASLTISGLKTEDEADYYCQSFDSTNPWVFGGGTK LTVL (SEQ ID NO: 17) |

Evaluation of Ab-52 and Ab-55 from WO2014055897

WO2014055B97 (DANA FARBER CANCER INST INC) discloses human monoclonal antibodies that bind to PD-L1. The VL sequences of Ab-52 and Ab-55 disclosed in WO2014055897 include the sequence of SEQ ID NO:2. These antibodies were evaluated to see if there was any evidence of pH dependent binding.

Methods

The full-length anti-PD-L1 antibodies of Ab-52 and Ab-55 were prepared from the sequences in WO2014055897 (see page 16 of WO2014055897). The positive control anti-PD-L1 mAb, 2.7A04OPT, was from WO2011066389 (see page 71 of WO2011066389) and the negative control mAb (2A11) is an anti-HEL (hen egg lysozyme).

Fabs were prepared from the intact mAbs using a commercial kit.

PD-L1 Neutralising ELISA

The mAbs or Fabs (100 to 0.14 nM) were added to a 96-well plate coated with 1 μg/ml PD-1 and the inhibition of 1 μg/ml PD-L-biotin was measured to determine the neutralising ability of each mAb or Fab. The PD-L1 interaction with PD-L1-biotin was detected with Extravidin-HRP. The buffer utilised was 0.1% casein/Krebs/lactate at pH6.0 or pH7.4).

The full methodologies of the assays conducted are provided in the Examples section of this application under the headings "ELISA binding to PD-L1 at different pHs" and "Screening antibodies for PD-1:PD-L1 inhibition".

Results

In the first experiment (FIG. 8) Fabs of Ab-52 and Ab-55 were compared in their ability to neutralise PD-L1 at pH 6 or pH 7.4 versus each of the 5 Fabs of the present invention (8B06, 8D06, 8G08, 8A04, 8D04). Fab 2.7A04OPT from WO2011066389 was used as a positive control.

The positive control comparator mAb 2.7A040PT inhibited PD-L1 binding to PD-1 equally at pH 6 compared to pH 7.4.

The five Fabs of the present invention (8D06, 8A04, 8G08, 8D04, 8B06) inhibited PD-L1 binding to PD-L1 at pH 6 with very little inhibition observed at pH 7.4 as expected. In contrast no inhibition of binding was observed at either pH with the Fabs of Ab-52 and Ab-55. This could be due to a lower affinity of neutralisation of Fabs Ab-52 and Ab-55 compared to the other Fabs used in FIG. 8.

For this reason, Ab-52 and Ab-55 mAbs were utilised. In the second experiment to determine if they possessed any pH dependence neutralising activity (FIG. 9).

Two of the Fabs of the present invention (8G08 and 8B06) were used in this assay and again showed pH dependent neutralisation at pH 6 and pH 6.5 with little activity at pH 7.4. In complete contrast the mAbs Ab52 and Ab55 showed no pH dependence neutralisation of PD-L1 binding to PD-1. The data being comparable to the positive control Fab 2.7A040PT.

Therefore, despite the small overlap in sequence, Ab-52 and Ab-55 do not share the novel properties of the anti-PD-L1 antigen binding molecules of the invention. Specifically, Ab-52 and Ab-55 do not share the higher affinity for PD-L1 at pH 6.0 than pH 7.4, which is demonstrated by the anti-PD-L1 antigen binding molecules of the invention.

EMBODIMENTS OF THE INVENTION

The present invention provides at least the following embodiments, listed as numbered clauses:

1. An anti-PD-L1 antigen binding molecule comprising:
a VLCDR1 having at least 80% identity to the amino acid sequence of any one of SEQ ID NOs 16, 12, 10, 14, 18, or 2.

2. The anti-PD-L1 antigen binding molecule of clause 1 comprising:
a VLCDR1 having at least 85%, 90%, 91%, 92%, 93%, 94%, 95%, 96%, 97%, 98% or 99% identity to the amino acid sequence of any one of SEQ ID NOs 16, 12, 10, 14, 18, and 2.

3. The anti-PD-L1 antigen binding molecule of clause 1 comprising:
a VLCDR1 comprising the amino acid sequence of any one of SEQ ID NOs 16, 12, 10, 14, 18, or 2.

4. The anti-PD-L1 antigen binding molecule of any one of clauses 1 to 3 comprising:
    a VHCDR1 having at least 80% identity to the amino acid sequence of SEQ ID NO 6
    a VHCDR2 having at least 80% identity to the amino acid sequence of SEQ ID NO 7; and
    a VHCDR3 having at least 80% identity to the amino acid sequence of SEQ ID NO 8 and/or
    a VLCDR1 having at least 80% identity to the amino acid sequence of any one of SEQ ID NOs; 16, 12, 10, 14, 18, and 2;

a VLCDR2 having at least 80% identity to the amino acid sequence of SEQ ID NO 3;

a VLCDR3 having at least 80% identity to the amino acid sequence of SEQ ID NO 4.

5. The anti-PD-L1 antigen binding molecule of any one of clauses 1 to 4 comprising:

a VHCDR1 having at least 85%, 90%, 91%, 92%, 93%, 94%, 95%, 96%, 97%, 98% or 99% identity to the amino acid sequence of SEQ ID NO 6;

a VHCDR2 having at least 85%, 90%, 91%, 92%, 93%, 94%, 95%, 96%, 97%, 98% or 99% identity to the amino acid sequence of SEQ ID NO 7; and a VHCDR3 having at least 85%, 90%, 91%, 92%, 93%, 94%, 95%, 96%, 97%, 98% or 99% Identity to the amino acid sequence of SEQ ID NO 8;

and/or a VLCDR1 having at least 85%, 90%, 91%, 92%, 93%, 94%, 95%, 96%, 97%, 98% or 99% identity to the amino acid sequence of any one of SEQ ID NOs; 16, 12, 10, 14, 18, and 2;

a VLCDR2 having at least 85%, 90%, 91%, 92%, 93%, 94%, 95%, 96%, 97%, 98% or 99% identity to the amino acid sequence of SEQ ID NO 3; and a VLCDR3 having at least 85%, 90%, 91%, 92%, 93%, 94%, 95%, 96%, 97%, 98% or 99% identity to the amino acid sequence of SEQ ID NO 4.

6. The anti-PD-L1 antigen binding molecule of any one of clauses 1 to 5 comprising:

a VHCDR1 comprising the amino acid sequence of SEQ ID NO 6 a VHCDR2 comprising the amino acid sequence of SEQ ID NO 7; and a VHCDR3 comprising the amino acid sequence of SEQ ID NO 8 and/or a VLCDR1 comprising the amino acid sequence of any one of SEQ ID NOs; 16, 12, 10, 14, 18, or 2;

a VLCDR2 comprising the amino acid sequence of SEQ ID NO 3; and a VLCDR3 comprising the amino acid sequence of SEQ ID NO 4.

7. The anti-PD-L1 antigen binding molecule of any one of clauses 1 to 6 comprising:

a heavy chain variable region having at least 80% identity to the amino acid sequence SEQ ID NO: 5;

and/or a light chain variable region having at least 80% identity to the amino acid sequence selected from the group consisting of SEQ ID NO: 15, SEQ ID NO: 11, SEQ ID NO: 9, SEQ ID NO: 13, SEQ ID NO: 17, SEQ ID NO: 1.

8. The anti-PD-L1 antigen binding molecule of any one of clauses 1 to 7 comprising:

a heavy chain variable region having at least 85%, 90%, 91%, 92%, 93%, 94%, 95%, 96%, 97%, 98% or 99% identity to the amino acid sequence SEQ ID NO: 5;

and/or a light chain variable region having at least 85%, 90%, 91%, 92%, 93%, 94%, 95%, 96%, 97%, 98% or 99% identity to the amino acid sequence selected from the group consisting of SEQ ID NO: 15, SEQ ID NO: 11, SEQ ID NO: 9, SEQ ID NO: 13, SEQ ID NO: 17, SEQ ID NO: 1.

9. The anti-PD-11 antigen binding molecule of any one of clauses 1 to 8 comprising:

a heavy chain variable region comprising the amino acid sequence SEQ ID NO: 5;

and/or a light chain variable region comprising the amino acid sequence selected from the group consisting of SEQ ID NO:

15, SEQ ID NO: 11, SEQ ID NO: 9, SEQ ID NO: 13, SEQ ID NO: 17 and SEQ ID NO: 1.

10. The anti-PD-L1 antigen binding molecule of any preceding clause, wherein the antigen binding molecule is selected from the group consisting of:

(a) an anti-PD-L1 antigen binding molecule comprising a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and a light chain variable region comprising a VLCDR1 comprising the amino acid sequence RETELSRRLHYVR (SEQ ID NO: 16), a VLCDR2 comprising the amino acid sequence EDDQRPS (SEQ ID NO: 3) and a VLCDR3 comprising the amino acid sequence QNVLTTPWT (SEQ ID NO: 4);

or comprising VHCDR and VLCDR sequences that are at least 90%, at least 95%, at least 98% or at least 99% identical thereof;

(b) an anti-PD-L1 antigen binding molecule comprising a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and a light chain variable region comprising a VLCDR1 comprising the amino acid sequence VLSPRTHAGHYYR (SEQ ID NO: 12), a VLCDR2 comprising the amino acid sequence EDDQRPS (SEQ ID NO: 3) and a VLCDR3 comprising the amino acid sequence QNVLTTPWT (SEQ ID NO: 4);

or comprising VHCDR and VLCDR sequences that are at least 90%, at least 95%, at least 98% or at least 99% identical thereof;

(c) an anti-PD-L1 antigen binding molecule comprising a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and a light chain variable region comprising a VLCDR1 comprising the amino acid sequence ISNDVPASGHYHR (SEQ ID NO: 10), a VLCDR2 comprising the amino acid sequence EDDQRPS (SEQ ID NO: 3) and a VLCDR3 comprising the amino acid sequence QNVLTTPWT (SEQ ID NO: 4);

or comprising VHCDR and VLCDR sequences that are at least 90%, at least 95%, at least 98% or at least 99% identical thereof;

(d) an anti-PD-L1 antigen binding molecule comprising a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and a light chain variable region comprising a VLCDR1 comprising the amino acid sequence MRTGTGNKGHYTR (SEQ ID NO: 14), a VLCDR2 comprising the amino acid sequence EDDQRPS (SEQ ID NO: 3) and a VLCDR3 comprising the amino acid sequence QNVLTTPWT (SEQ ID NO: 4); or comprising VHCDR and VLCDR sequences that are at least 90%, at least 95%, at least 98% or at least 99% identical thereof;

(e) an anti-PD-L1 antigen binding molecule comprising a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and a light chain variable region comprising a VLCDR1 comprising the amino acid sequence RGTGSSFHHKYVR (SEQ ID NO: 18), a VLCDR2 comprising the amino acid sequence EDDQRPS (SEQ ID NO: 3) and a VLCDR3 comprising the amino acid sequence QNVLTTPWT (SEQ ID NO: 4);

or comprising VHCDR and VLCDR sequences that are at least 90%, at least 95%, at least 98% or at least 99% identical thereof.

(f) an anti-PD-L1 antigen binding molecule comprising a heavy chain variable region comprising a VHCDR1 comprising the amino acid sequence SYGMY (SEQ ID NO: 6), a VHCDR2 comprising the amino acid sequence VISYDGSNKYYADSVKG (SEQ ID NO: 7), a VHCDR3 comprising the amino acid sequence GALTHWGVVIGDGMDV (SEQ ID NO: 8); and a light chain variable region comprising a VLCDR1 comprising the amino acid sequence TRSSG-SIASNYVQ (SEQ ID NO: 2), a VLCDR2 comprising the amino acid sequence EDDQRPS (SEQ ID NO: 3) and a VLCDR3 comprising the amino acid sequence QNVLTTPWT (SEQ ID NO: 4);

or comprising VHCDR and VLCDR sequences that are at least 90%, at least 95%, at least 98% or at least 99% identical thereof;

11. The anti-PD-L1 antigen binding molecule of any preceding clause, wherein the antigen-binding molecule comprises a heavy chain variable region and a light chain variable region selected from the group consisting of:

(a) a VH comprising the amino acid sequence of SEQ ID NO: 5 and a VL comprising the amino acid sequence of SEQ ID NO: 15 or comprising VH and VL sequences that are at least 90%, at least 95%, at least 98% or at least 99% identical to SEQ ID NO: 5 and SEQ ID NO: 15, respectively;

(b) a VH comprising the amino acid sequence of SEQ ID NO: 5 and a VL comprising the amino acid sequence of SEQ ID NO: 11 or comprising VH and VL sequences that are at least 90%, at least 95%, at least 98% or at least 99% identical to SEQ ID NO: 5 and SEQ ID NO: 11, respectively;

(c) a VH comprising the amino acid sequence of SEQ ID NO: 5 and a VL comprising the amino acid sequence of SEQ ID NO: 9 or comprising VH and VL sequences that are at least 90%, at least 95%, at least 98% or at least 99% identical to SEQ ID NO: 5 and SEQ ID NO: 9, respectively;

(d) a VH comprising the amino acid sequence of SEQ ID NO: 5 and a VL comprising the amino acid sequence of SEQ ID NO: 13 or comprising VH and VL sequences that are at least 90%, at least 95%, at least 98% or at least 99% identical to SEQ ID NO: 5 and SEQ ID NO: 13, respectively;

(e) a VH comprising the amino acid sequence of SEQ ID NO: 5 and a VL comprising the amino acid sequence of SEQ ID NO: 17 or comprising VH and VL sequences that are at least 90%, at least 95%, at least 98% or at least 99% identical to SEQ ID NO: 5 and SEQ ID NO: 17, respectively;

(f) a VH comprising the amino acid sequence of SEQ ID NO: 5 and a VL comprising the amino acid sequence of SEQ ID NO: 1 or comprising VH and VL sequences that are at least 90%, at least 95%, at least 98% or at least 99% identical to SEQ ID NO: 5 and SEQ ID NO: 1, respectively;

12. The anti-PDL1 antigen binding molecule of any preceding clause wherein the anti-PD-L1 antigen binding molecule is an antibody selected from the group consisting of 8506, 8D06, 8G08, 8A04, 8D04, 2A09.

13. The anti-PD-L1 antigen binding molecule of clause 12, wherein the antibody comprises 1 to 10, 1 to 5 or 1 to 2 conservative amino acid substitutions across all 6 CDR regions.

14. The anti-PD-L1 antigen binding molecule of clause 12, wherein the antibody comprises 1 to 10, 1 to 5 or 1 to 2 conservative amino acid substitutions in one or both of the variable heavy and light regions.

15. The anti-PD-L1 antigen binding molecule clause 12, wherein the antibody comprises 1 to 10, 1 to 5, or 1 to 2 conservative amino acid substitutions in the framework regions.

16. An antigen-binding molecule that specifically binds to PD-L1 and inhibits the binding of PD-L1 to an antigen-binding molecule of any one of clauses 1 to 15.

17. The antigen-binding molecule of clause 16 wherein the antigen-binding molecule specifically binds to PD-L1 and inhibits the binding of PD-L1 to an antibody selected from the group consisting of 8B06, 8D06, 8G08, 8A04, 8D04, 2A09.

18. An antigen-binding molecule that specifically binds to an epitope of PD-L1 that is bound by an antigen-binding molecule of any one of clauses 1 to 15.

19. The antigen-binding molecule of clause 18 wherein the antigen-binding molecule specifically binds to an epitope of PD-L1 that is bound by an antibody selected from the group consisting of 8B06, 8D06, 8G08, 8A04, 8D04, 2A09.

20. An antigen-binding molecule that specifically binds to an epitope of human PD-L1 wherein the epitope is comprised in SEQ ID NO:19.

21. An antigen-binding molecule that specifically binds to an epitope of cynomolgus PD-L1.

22. The antigen-binding molecule of clause 20 wherein the antigen binding molecule is selected from the group consisting of 8B06, 8D06, 8G08, 8A04, 8D04, 2A09, and fragments and variants thereof.

23. The antigen-binding molecule of clause 20 wherein the antigen-binding molecule is 8B06.

24. The antigen-binding molecule of clause 20 wherein the antigen-binding molecule is 8A04.

25. An antigen-binding molecule that specifically binds to PD-L1 and competes with binding to PD-L1 with an antigen-binding molecule of any one of clauses 1 to 15.

26. The antigen-binding molecule of clause 25 wherein the antigen-binding molecule specifically binds to PD-L1 and competes with binding to PD-L1 with an antibody selected from the group consisting of 8B06, 8D06, 8G08, 8A04, 8D04, 2A09.

27. An anti-PD-L1 antigen binding molecule according to any one of clauses 1 to 15, comprising 1 to 10 amino acid substitutions in the specified sequence or sequences.

28. The anti-PD-L1 antigen binding molecule according to clause 27, comprising 1 to 5 amino acid substitutions in the specified sequence or sequences.

29. The anti-PD-L1 antigen binding molecule according to clause 27, comprising 1 to 2 amino acid substitutions in the specified sequence or sequences.

30. The anti-PD-L1 antigen binding molecule according to any one of clauses 27 to 29, wherein the 1 to 10, 1 to 5 or 1 to 2 amino acid substitutions are in the CDR region or CDR regions of the antigen binding molecule.

31. The anti-PD-L1 antigen binding molecule according to any one of clauses 27 to 29, wherein the 1 to 10, 1 to 5 or 1 to 2 amino acid substitutions are in one or both of the variable regions of the antigen binding molecule.

32. The anti-PD-L1 antigen binding molecule according to any one of clauses 27 to 29, wherein the 1 to 10, 1 to 5 or 1 to 2 amino acid substitutions are in the framework regions of the antigen binding molecule.

33. The anti-PD-L1 antigen binding molecule according to any one of clauses 27 to 29, wherein the antigen-binding molecule is a variant derived from an antibody selected from the group consisting of 8B06, 8D06, 8G08, 8A04, 8D04, 2A09.

34. The anti-PD-L1 antigen binding molecule according to any one of clauses 13 to 15 or 27 to 29, wherein the amino acid substitutions are conservative amino acid substitutions.

35. The anti-PD-L1 antigen binding molecule of any preceding clause wherein the antigen binding molecule is an antibody or antigen-binding fragment or derivative thereof.

36. The anti-PD-L1 antigen binding molecule of clause 35, wherein the antigen-binding antibody fragment or derivative is Fab, F(ab')2, Fv, scFv, dAb, Fd, or a diabody.

37. The anti-PD-L1 antigen binding molecule of clause 35, wherein the antigen-binding antibody fragment is a Fab.

38. The anti-PD-L1 antigen binding molecule of clause 35 wherein the antibody or antigen-binding fragment or derivative thereof is monovalent.

39. The anti-PD-L1 antibody of clause 35 wherein the antibody or antigen-binding fragment or derivative thereof is fully human.

40. The anti-PD-L1 antibody or antigen-binding antibody fragment or derivative thereof of any one of clauses 35 to 39, wherein the antibody or antigen-binding antibody fragment or derivative is an IgA, IgD, IgE, IgG, IgM or IgY antibody or antigen-binding antibody fragment or derivative.

41. The anti-PD-L1 antibody or antibody fragment of any one of clauses 35 to 39 wherein the antibody or antigen-binding fragment or derivative thereof is an IgG antibody or antigen-binding fragment of derivative thereof.

42. The anti-PD-L1 antibody or antigen-binding antibody fragment or derivative of clause 41, wherein the IgG antibody or antigen-binding antibody fragment or derivative is an IgG1 antibody or antigen-binding antibody fragment or derivative thereof.

43. An anti-PD-L1 antigen binding molecule, wherein the anti-PD-L1 antigen binding molecule is an affinity matured mutant of the antibody 2A09.

44. The anti-PD-L1 antigen binding molecule of clause 43, wherein the affinity matured mutant is selected from the group consisting of 8B06, 8D06, 8G08, 8A04 and 8D04.

45. The antigen binding molecule of any preceding clause, wherein the antigen binding molecule specifically binds to human or cynomolgus PD-L1.

46. The antigen binding molecule of any preceding clause, wherein the antigen binding molecule specifically binds to PD-L1 in a pH dependant manner.

47. The antigen binding molecule of any preceding clause, wherein the antigen binding molecule specifically binds to PD-L1 at an acidic pH.

48. The antigen binding molecule of any preceding clause, wherein the antigen binding molecule specifically binds to PD-L1 at a pH of from about pH 6 to about pH 6.5.

49. The antigen binding molecule of any preceding clause, wherein the antigen binding molecule has a higher affinity for PD-L1 at an acidic pH than at a physiological pH.

50. The antigen binding molecule of any preceding clause, wherein the antigen binding molecule has a higher affinity for PD-L1 at about pH 6.0 than at about pH 7.4.

51. The antigen binding molecule clause 49, wherein the acidic pH is equal to or less than about pH 6.5.

52. The antigen binding molecule of clause 49, wherein the physiological pH is about pH 7.4

53. The antigen binding molecule of any preceding clause, wherein the antigen binding molecule has at least about 5 times higher affinity for PD-L1 at about pH 6.0 than at a pH of about 7.4.

54. The antigen binding molecule of any preceding clause, wherein the antigen binding molecule has a EC50 value for PD-L1 at pH 6.0 of less than about 15 nM 55. The antigen binding molecule of any preceding clause, wherein the antigen binding molecule has a EC50 value for PD-L1 at pH 6.0 of from about 1.45 nM to about 15 nM 56. The antigen binding molecule of any preceding clause, wherein the antigen binding molecule has a EC50 value for PD-L1 at pH 7.4 of at least about 10 nM 57. The antigen binding molecule of any preceding clause, wherein the antigen binding molecule has a EC50 value for PD-L1 at pH 7.4 of from about 13.2 nM to about 100 nM 58. The antigen binding molecule of any preceding clause, wherein the antigen binding molecule has a pH 6.0:7.4 binding ratio of at least about 5.

59. The antigen binding molecule of any preceding clause, wherein the antigen binding molecule has an EC50 value for PD-L1 at pH 6.0 of less than about 15 nM and a EC50 value for PD-L1 at pH 7.4 of at least about 10 nM, wherein the antigen binding molecule has a pH 6.0:7.4 binding ratio of at least 5.

60. The antigen binding molecule of any preceding clause, wherein the antigen binding molecule inhibits the binding of PD-L1 to PD-1 and/or CD80, or the binding of PD-L1 expressing cells to PD-1 and/or CD80.

61. The antigen binding molecule of clause 60, wherein the antigen binding molecule inhibits the binding by at least about 40%, at least about 50% or at least about 80%.

62. The antigen binding molecule of any preceding clause, wherein the IC50 inhibition value of PD-L1 binding to PD-1 is higher at about pH 7.4 than at about pH 6.0.

63. The antigen binding molecule of any preceding clause, wherein the IC50 inhibition value of PD-L1 binding to PD-1 at about pH 6.0 is from about 12.1 nM to about 42.3 nM 64. The antigen binding molecule of any preceding clause, wherein the IC50 Inhibition value of PD-L1 binding to PD-1 at about pH 6.0 is less than about 50 nM 65. The antigen binding molecule of any preceding clause, wherein the IC50 inhibition value of PD-L1 binding to PD-1 at about pH 7.4 is from about 81.2 nM to about 100 nM 66. The antigen binding molecule of any preceding clause, wherein the IC50 Inhibition value of PD-L1 binding to PD-1 at pH 7.4 is at least 50 nM 67. The antigen binding molecule of any preceding clause, wherein the IC50 Inhibition value of PD-L1 binding to PD-1 at pH 7.4 is at least 80 nM 68. The antigen binding molecule of any preceding clause, wherein the antigen binding molecule has a pH 6.0:7.4 inhibition ratio of at least about 2.

69. The antigen binding molecule of any preceding clause, wherein the IC50 inhibition value of PD-L1 binding to PD-1 at pH6.0 is less than about 50 nM and the IC50 inhibition value of PD-L1 binding to PD-1 at pH7.4 is at least about 80 nM, wherein the antigen binding molecule has a pH 6.0:7.4 inhibition ratio of at least about 2.

70. The antigen binding molecule of any preceding clause, wherein the PD-L1 is human PD-L1 or cynomolgus PD-L1

71. The antigen binding molecule of any preceding clause, wherein the antigen binding molecule reverses immune suppression when administered In vivo or In vitro.

72. The antigen binding molecule of any preceding clauses, wherein the antigen binding molecule enhances T cell immunity when administered in vivo or in vitro.

73. The antigen binding molecule of any preceding clauses, wherein the antigen binding molecule is an immune checkpoint inhibitor.

74. A pharmaceutical composition comprising an antigen binding molecule of any preceding clause, optionally further comprising one or more pharmaceutically acceptable excipients.

75. A pharmaceutical composition of clause 74, further comprising an additional therapeutically active agent, or wherein the pharmaceutical composition is for use in combination with another therapy or additional therapeutically active agent.

76. The pharmaceutical composition of clause 75, wherein the other therapy or additional therapeutically active agent is selected from the group consisting of: radiation therapy, chemotherapy treatment, targeted therapy, immunotherapy, monoclonal antibody therapy, hormonal therapy, angiogenesis inhibition, cancer vaccines, oncolytic virus, toll like receptor agonists, epigenetic modifications, engineered T cells, T cell co-stimulation agonists, tyrosine kinase inhibitors, other anti-cancer chemical agents, palliative care for cancer therapy, an immune checkpoint inhibitor, an immunosuppressant, an anti-inflammatory, an immune modulators, an immune activator and/or an inhibitor such as an IDO inhibitor, a CSF-1R inhibitor, a TGFB inhibitor, T cell co-stimulation antagonists, Treg inhibitors, macrophage modulators, natural killer cell modulators or a chemokine receptor inhibitor.

77. The pharmaceutical composition of clause 76, wherein the chemotherapy treatment is selected from the group consisting of: gemcitabine, cyclophosphamide, doxorubicin, paclitaxel, cisplatin.

78. The pharmaceutical composition of clause 76, wherein the T cell co-stimulation agonist is selected from the group consisting of 4-1BB, OX40, CD40, GITR, BTLA, CD70 and ICOS.

79. The pharmaceutical composition of clause 76, wherein the immune checkpoint inhibitor acts on a member of the group consisting of PD-1, CTLA-4, TIM-3, LAG-3, VISTA, and TIGIT.

80. The pharmaceutical composition of clause 75, wherein the other therapy or additional therapeutically active agent is another antigen binding molecule 81. The pharmaceutical composition of clause 80, wherein the additional antigen binding molecule is selected from the group consisting of anti-PD-L1 antigen binding molecules, anti-PD-1 antigen binding molecules, anti-CTLA-4 antigen binding molecules, anti-OX40 antigen binding molecules, anti-ICOS antigen binding molecules, anti-GITR antigen binding molecules, optionally wherein the additional antigen binding molecule is an antibody.

82. A kit comprising an antigen binding molecule of any one of clauses 1 to 73 or a pharmaceutical composition according to any one of clauses 74 to 81, further comprising an additional therapeutically active agent.

83. The kit of clause 82 further comprising instructions for use.

84. The kit of clause 82 or 83, wherein the pharmaceutical components are disposed separately in the kit.

85. The kit of any of clauses 82 to 84, wherein the additional therapeutically active agent is selected from a list consisting of an immune checkpoint inhibitor, an immunosuppressant, an anti-inflammatory, an immune modulators, an immune activator and/or an inhibitor such as an IDO inhibitor, a CSF-1R inhibitor, a TGFB inhibitor, a T cell co-stimulation antagonist, a Treg inhibitor, a macrophage modulator, a natural killer cell modulator or a chemokine receptor inhibitor.

86. The kit of any of clauses 82 to 84, wherein the additional therapeutically active agent is an immune checkpoint inhibitor.

87. The kit of any of clauses 82 to 86, wherein the antigen binding molecule or pharmaceutical composition and the additional therapeutically active agent are for separate, sequential or simultaneous administration.

88. An antigen binding molecule of any one of clauses 1 to 73, or a pharmaceutical composition of any one of clauses 74 to 81, for use in medicine.

89. An antigen binding molecule of any one of clauses 1 to 73, or a pharmaceutical composition of any one of clauses 78 to 81, for use in the treatment or prevention of cancer.

90. The antigen binding molecule or pharmaceutical composition for use as in clause 89, wherein the cancer is selected from the group consisting of cardiac, sarcoma, angiosarcoma, fibrosarcoma, rhabdomyosarcoma, liposarcoma, myxoma, metastatic, rhabdomyoma, fibroma, lipoma and teratoma; Lung, bronchogenic carcinoma, squamous cell, undifferentiated small cell, non-small cell undifferentiated large cell, adenocarcinoma, alveolar (bronchiolar) carcinoma, bronchial adenoma, sarcoma, lymphoma, chondromatous hamartoma, mesothelioma; Gastrointestinal: esophagus, squamous cell carcinoma, adenocarcinoma, leiomyosarcoma, lymphoma, stomach, carcinoma, lymphoma, leiomyosarcoma, head and neck, gastric, pancreas, ductal adenocarcinoma, insulinoma, glucagonoma, gastrinoma, carcinoid tumors, vipoma, small bowel, adenocarcinoma, lymphoma, carcinoid tumors, Karposi's sarcoma, leiomyoma, hemangioma, lipoma, neurofibroma, fibroma, large bowel, adenocarcinoma, tubular adenoma, villous adenoma, hamartoma, leiomyoma, colorectal; Genitourinary tract: kidney, adenocarcinoma, Wilm's tumor [nephroblastoma], lymphoma, leukemia, bladder and urethra, squamous cell carcinoma, transitional cell carcinoma, adenocarcinoma, urothelial carcinoma, prostate, adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma; Liver, hepatoma, hepatocellular carcinoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull, osteoma, hemangioma, granuloma, xanthoma, osteltis deformans, meninges, meningloma, meningiosarcoma, gliomatosis, brain, astrocytoma, medulloblastoma, glioma, ependymoma, germinoma [pinealoma], glioblastoma multiform, oligodendroglioma, schwannoma, retinoblastoma, congenital tumors, spinal cord neurofibroma, meningloma, glioma, sarcoma; Gynecological: uterus, endometrial carcinoma, cervix, cervical carcinoma, pre tumor cervical dysplasia, ovaries, ovarian carcinoma, serous cystadenocarcinoma, mucinous cystadenocarcinoma, unclassified carcinoma, granulosa thecal cell tumors, Sertoli-Leydig cell tumors, dysgerminoma, malignant teratoma, vulva, squamous cell carcinoma, intraepithelial carcinoma, adenocarcinoma, fibrosarcoma, melanoma, vaginal, clear cell carcinoma, squamous cell carcinoma, botryoid sarcoma (embryonal rhabdomyosarcoma), fallopian tubes carcinoma, breast; Hematologic: blood, myeloid leukemia [acute and chronic], acute lymphoblastic leukemia, chronic lymphocytic leukemia, myeloproliferative diseases, multiple myeloma, myelodysplastic syndrome), Hodgkin's lymphoma, Hodgkin's disease, non Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

91. The antigen binding molecule, affinity matured mutant or pharmaceutical composition for use as in clause 89 or 90, wherein the cancer is selected from the group consisting of carcinoma, lymphoma, leukemia, blastoma, and sarcoma.

92. The antigen binding molecule or pharmaceutical composition for use as in any of clauses 89 to 91, wherein the cancer is selected from the group consisting of melanoma, metastatic cancer, non-small cell lung cancer, head and neck cancer, Hodgkin's lymphoma, urothelial carcinoma, gastric cancer, cervical cancer, hepatocellular carcinoma and bladder cancer.

93. Use of an antigen binding molecule of any one of clauses 1 to 73 in the manufacture of a medicament for use in the treatment of cancer.

94. Use of an antigen binding molecule according to clause 93, wherein cancer is selected from the group consisting of cardiac, sarcoma, angiosarcoma, fibrosarcoma, rhabdomyosarcoma, liposarcoma, myxoma, metastatic, rhabdomyoma, fibroma, lipoma and teratoma; Lung, bronchogenic carcinoma, squamous cell, undifferentiated small cell, non-small cell undifferentiated large cell, adenocarcinoma, alveolar (bronchiolar) carcinoma, bronchial adenoma, sarcoma, lymphoma, chondromatous hamartoma, mesothelioma; Gastrointestinal: esophagus, squamous cell carcinoma, adenocarcinoma, leiomyosarcoma, lymphoma, stomach, carcinoma, lymphoma, leiomyosarcoma, head and neck, gastric, pancreas, ductal adenocarcinoma, insulinoma, glucagonoma, gastrinoma, carcinoid tumors, vipoma, small bowel, adenocarcinoma, lymphoma, carcinoid tumors, Karposi's sarcoma, leiomyoma, hemangioma, lipoma, neurofibroma, fibroma, large bowel, adenocarcinoma, tubular adenoma, villous adenoma, hamartoma, leiomyoma, colorectal; Genitourinary tract: kidney, adenocarcinoma, Wilm's tumor [nephroblastoma], lymphoma, leukemia, bladder and urethra, squamous cell carcinoma, transitional cell carcinoma, adenocarcinoma, urothelial carcinoma, prostate, adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma; Liver, hepatoma, hepatocellular carcinoma, cholangiocarcinoma, hepatoblastoma, angiosarcoma, hepatocellular adenoma, hemangloma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull, osteoma, hemangioma, granuloma, xanthoma, osteitis deformans, meninges, meningioma, meningiosarcoma, gliomatosis, brain, astrocytoma, medulloblastoma, glioma, ependymoma, germinoma [pinealoma], glioblastoma multiform, oligodendroglioma, schwannoma, retinoblastoma, congenital tumors, spinal cord neurofibroma, meningioma, glioma, sarcoma; Gynecological: uterus, endometrial carcinoma, cervix, cervical carcinoma, pre tumor cervical dysplasia, ovaries, ovarian carcinoma, serous cystadenocarcinoma, mucinous cystadenocarcinoma, unclassified carcinoma, granulosa thecal cell tumors, Sertoli-Leydig cell tumors, dysgerminoma, malignant teratoma, vulva, squamous cell carcinoma, intraepithelial carcinoma, adenocarcinoma, fibrosarcoma, melanoma, vaginal, clear cell carcinoma, squamous cell carcinoma, botryoid sarcoma (embryonal rhabdomyosarcoma), fallopian tubes carcinoma, breast; Hematologic: blood, myeloid leukemia [acute and chronic], acute lymphoblastic leukemia, chronic lymphocytic leukemia, myeloproliferative diseases, multiple myeloma, myelodysplastic syndrome), Hodgkin's lymphoma, Hodgkin's disease, non Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

95. Use of an antigen binding molecule according to clause 93 wherein the cancer is selected from the group consisting of melanoma, metastatic cancer, non-small cell lung cancer, head and neck cancer, Hodgkin's lymphoma, urothelial carcinoma, gastric cancer, cervical cancer, hepatocellular carcinoma and bladder cancer.

96. A method for the treatment or prevention of a PD-L1-mediated disease or disorder comprising administering to the subject an antigen binding molecule of any one of clauses 1 to 73 or a pharmaceutical composition according to any one of clauses 74 to 81.

97. The method of clause 96, wherein the PD-L1-mediated disease or disorder is a cancer.

98. The method of treatment of clause 97, wherein the cancer is cardiac, sarcoma, angiosarcoma, fibrosarcoma, rhabdomyosarcoma, liposarcoma, myxoma, metastatic, rhabdomyoma, fibroma, lipoma and teratoma; Lung, bronchogenic carcinoma, squamous cell, undifferentiated small cell, non-small cell undifferentiated large cell, adenocarcinoma, alveolar (bronchiolar) carcinoma, bronchial adenoma, sarcoma, lymphoma, chondromatous hamartoma, mesothelioma; Gastrointestinal: esophagus, squamous cell carcinoma, adenocarcinoma, leiomyosarcoma, lymphoma, stomach, carcinoma, lymphoma, leiomyosarcoma, head and neck, gastric, pancreas, ductal adenocarcinoma, insulinoma, glucagonoma, gastrinoma, carcinoid tumors, vipoma, small bowel, adenocarcinoma, lymphoma, carcinoid tumors, Karposi's sarcoma, leiomyoma, hemangioma, lipoma, neurofibroma, fibroma, large bowel, adenocarcinoma, tubular adenoma, villous adenoma, hamartoma, leiomyoma, colorectal; Genitourinary tract: kidney, adenocarcinoma, Wilm's tumor [nephroblastoma], lymphoma, leukemia, bladder and urethra, squamous cell carcinoma, transitional cell carcinoma, adenocarcinoma, urothelial carcinoma, prostate, adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma; Liver, hepatoma, hepatocellular carcinoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull, osteoma, hemangloma, granuloma, xanthoma, osteltis deformans, meninges, meningloma, meningiosarcoma, gliomatosis, brain, astrocytoma, medulloblastoma, glioma, ependymoma, germinoma [pinealoma], glioblastoma multiform, oligodendroglioma, schwannoma, retinoblastoma, congenital tumors, spinal cord neurofibroma, meningioma, glioma, sarcoma; Gynecological: uterus, endometrial carcinoma, cervix, cervical carcinoma, pre tumor cervical dysplasia, ovaries, ovarian carcinoma, serous cystadenocarcinoma, mucinous cystadenocarcinoma, unclassified carcinoma, granulosa thecal cell tumors, Sertoli-Leydig cell tumors, dysgerminoma, malignant teratoma, vulva, squamous cell carcinoma, intraepithelial carcinoma, adenocarcinoma, fibrosarcoma, melanoma, vaginal, clear cell carcinoma, squamous cell carcinoma, botryoid sarcoma (embryonal rhabdomyosarcoma), fallopian tubes carcinoma, breast; Hematologic: blood, myeloid leukemia [acute and chronic], acute lymphoblastic leukemia, chronic lymphocytic leukemia, myeloproliferative diseases, multiple myeloma, myelodysplastic syndrome), Hodgkin's lymphoma, Hodgkin's disease, non Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

99. The method of treatment of clause 97, wherein the cancer is selected from the group consisting of melanoma, metastatic cancer, non-small cell lung cancer, head and neck cancer, Hodgkin's lymphoma, urothelial carcinoma, gastric cancer, cervical cancer, hepatocellular carcinoma and bladder cancer.

100. A method of inhibiting the binding of human PD-L1 to PD-1 and/or CD80 or the binding of PD-L1 expressing cells to PD-1 and/or CD80, comprising contacting the human PD-L1 or PD-L1 expressing cell with an antigen-binding molecule according to any one of clauses 1 to 73.

101. The method of clause 100, wherein the method is an in vitro method.

102. The method of clause 100, wherein the method is an in vivo method.

103. A nucleic acid encoding an antigen binding molecule of any one of clauses 1 to 73.

104. A plasmid comprising the nucleic acid of clause 103.

105. A vector comprising the nucleic acid of clause 103.

106. A host cell comprising a plasmid or vector according to clause 104 or clause 105.

107. A method of producing a cell that expresses an anti-PD-L1 antigen binding molecule, comprising transfecting said cell with a plasmid or vector according to clause 104 or 105.

108. A method for the production of an anti-PD-L1 antigen binding molecule, comprising culturing a host cell according to clause 106 in a cell culture medium under conditions to express the encoding nucleic acid sequence of the plasmid or vector inside the cell.

109. The method of clause 108, further comprising obtaining the anti-PD-L1 antigen binding molecule from the cell culture supernatant.

110. The method of clause 109, further comprising formulating the obtained anti-PD-L1 antigen binding molecule into a pharmaceutical composition with one or more pharmaceutically acceptable excipients.

---

The invention claimed is:

1. An anti-PD-L1 antigen binding molecule comprising a heavy chain variable region (VH) and a light chain variable region (VL), wherein:
(a) the VH comprises:
a VHCDR1 comprising the amino acid sequence of SEQ ID NO: 6,
a VHCDR2 comprising the amino acid sequence of SEQ ID NO: 7, and
a VHCDR3 comprising the amino acid sequence of SEQ ID NO: 8; and
(b) the VL comprises:
(i) a VLCDR1 comprising the amino acid sequence of SEQ ID NO: 16,
a VLCDR2 comprising the amino acid sequence of SEQ ID NO: 3, and
a VLCDR3 comprising the amino acid sequence of SEQ ID NO: 4;
(ii) a VLCDR1 comprising the amino acid sequence of SEQ ID NO: 12,
a VLCDR2 comprising the amino acid sequence of SEQ ID NO: 3, and
a VLCDR3 comprising the amino acid sequence of SEQ ID NO: 4;
(iii) a VLCDR1 comprising the amino acid sequence of SEQ ID NO: 10,
a VLCDR2 comprising the amino acid sequence of SEQ ID NO: 3, and
a VLCDR3 comprising the amino acid sequence of SEQ ID NO: 4;
(iv) a VLCDR1 comprising the amino acid sequence of SEQ ID NO: 14,
a VLCDR2 comprising the amino acid sequence of SEQ ID NO: 3, and
a VLCDR3 comprising the amino acid sequence of SEQ ID NO: 4; or
(v) a VLCDR1 comprising the amino acid sequence of SEQ ID NO: 18,
a VLCDR2 comprising the amino acid sequence of SEQ ID NO: 3, and
a VLCDR3 comprising the amino acid sequence of SEQ ID NO: 4.

2. The anti-PD-L1 antigen binding molecule of claim 1, wherein:
the VH comprises an amino acid sequence having at least 80% identity to the amino acid sequence of SEQ ID NO: 5; and
the VL comprises an amino acid sequence having at least 80% identity to an amino acid sequence selected from the group consisting of SEQ ID NO: 15, SEQ ID NO: 11, SEQ ID NO: 9, SEQ ID NO: 13, and SEQ ID NO: 17.

3. The anti-PD-L1 antigen binding molecule of claim 1, wherein:
the VH comprises the amino acid sequence SEQ ID NO: 5;
and
the VL comprises an amino acid sequence selected from the group consisting of SEQ ID NO: 15, SEQ ID NO: 11, SEQ ID NO: 9, SEQ ID NO: 13, and SEQ ID NO: 17.

4. The anti-PD-L1 antigen binding molecule of claim 1, wherein:
(a) the VH comprises the amino acid sequence of SEQ ID NO: 5 and the VL comprises the amino acid sequence of SEQ ID NO: 15;
(b) the VH comprises the amino acid sequence of SEQ ID NO: 5 and the VL comprises the amino acid sequence of SEQ ID NO: 11;
(c) the VH comprises the amino acid sequence of SEQ ID NO: 5 and the VL comprises the amino acid sequence of SEQ ID NO: 9;
(d) the VH comprises the amino acid sequence of SEQ ID NO: 5 and the VL comprises the amino acid sequence of SEQ ID NO: 13; or
(e) the VH comprises the amino acid sequence of SEQ ID NO: 5 and the VL comprises the amino acid sequence of SEQ ID NO: 17.

5. The anti-PD-L1 antigen binding molecule of claim 1, wherein the anti-PD-L1 antigen binding molecule is an antibody or antigen binding fragment or derivative thereof, optionally wherein the antibody, antigen binding fragment or derivative is a Fab, F(ab')2, Fv, scFv, dAb, Fd, or a diabody.

6. The anti-PD-L1 antigen binding molecule of claim 5, wherein the antibody or antigen binding fragment or derivative thereof is an IgA, IgD, IgE, IgG, IgM or IgY antibody.

7. The anti-PD-L1 antigen binding molecule of claim 6, wherein the antibody or antigen binding fragment or derivative thereof is bispecific.

8. The anti-PD-L1 antigen binding molecule of claim 1 wherein the anti-PD-L1 antigen binding molecule specifically binds to PD-L1 in a pH-dependent manner.

9. The anti-PD-L1 antigen binding molecule of claim 1, wherein the anti-PD-L1 antigen binding molecule has a higher affinity for PD-L1 at pH 6.0 than at pH 7.4.

10. The anti-PD-L1 antigen binding molecule of claim 1, wherein the anti-PD-L1 antigen binding molecule
a. reverses immune suppression; or
b. enhances T cell immunity when administered in vivo or in vitro.

11. A pharmaceutical composition comprising the anti-PD-L1 antigen binding molecule of claim 1 and a pharmaceutically acceptable excipient.

12. The pharmaceutical composition of claim 11, further comprising an additional therapeutically active agent.

13. A method of treating cancer in a subject in need thereof comprising:
administering the anti-PD-L1 antigen binding molecule according to claim 1; or administering a pharmaceutical composition comprising the anti-PD-L1 antigen binding molecule according to claim 1; wherein the cancer is selected from the group consisting of melanoma, metastatic cancer, non-small cell lung cancer, head and neck cancer, Hodgkin's lymphoma, urothelial carcinoma, gastric cancer, cervical cancer, hepatocellular carcinoma, and bladder cancer.

* * * * *

SEQUENCE LISTING

```
<160> NUMBER OF SEQ ID NOS: 62

<210> SEQ ID NO 1
<211> LENGTH: 111
<212> TYPE: PRT
<213> ORGANISM: Homo sapiens

<400> SEQUENCE: 1

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Asp Ser
                85                  90                  95

Thr Asn Pro Trp Val Phe Gly Gly Gly Thr Lys Leu Thr Val Leu
                100                 105                 110

<210> SEQ ID NO 2
<211> LENGTH: 13
```

```
<212> TYPE: PRT
<213> ORGANISM: Homo sapiens

<400> SEQUENCE: 2

Thr Arg Ser Ser Gly Ser Ile Ala Ser Asn Tyr Val Gln
1               5                   10

<210> SEQ ID NO 3
<211> LENGTH: 7
<212> TYPE: PRT
<213> ORGANISM: Homo sapiens

<400> SEQUENCE: 3

Glu Asp Asp Gln Arg Pro Ser
1               5

<210> SEQ ID NO 4
<211> LENGTH: 10
<212> TYPE: PRT
<213> ORGANISM: Homo sapiens

<400> SEQUENCE: 4

Gln Ser Phe Asp Ser Thr Asn Pro Trp Val
1               5                   10

<210> SEQ ID NO 5
<211> LENGTH: 125
<212> TYPE: PRT
<213> ORGANISM: Homo sapiens

<400> SEQUENCE: 5

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met Tyr Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Lys Gly Ala Leu Thr His Trp Gly Val Val Ile Gly Asp Gly Met
            100                 105                 110

Asp Val Trp Gly Gln Gly Thr Thr Val Thr Val Ser Ser
        115                 120                 125

<210> SEQ ID NO 6
<211> LENGTH: 5
<212> TYPE: PRT
<213> ORGANISM: Homo sapiens

<400> SEQUENCE: 6

Ser Tyr Gly Met Tyr
1               5

<210> SEQ ID NO 7
<211> LENGTH: 17
<212> TYPE: PRT
<213> ORGANISM: Homo sapiens
```

```
<400> SEQUENCE: 7

Val Ile Ser Tyr Asp Gly Ser Asn Lys Tyr Tyr Ala Asp Ser Val Lys
1               5                   10                  15

Gly

<210> SEQ ID NO 8
<211> LENGTH: 16
<212> TYPE: PRT
<213> ORGANISM: Homo sapiens

<400> SEQUENCE: 8

Gly Ala Leu Thr His Trp Gly Val Val Ile Gly Asp Gly Met Asp Val
1               5                   10                  15

<210> SEQ ID NO 9
<211> LENGTH: 111
<212> TYPE: PRT
<213> ORGANISM: Homo sapiens

<400> SEQUENCE: 9

Asn Phe Met Leu Thr Gln Pro His Ser Val Ser Glu Ser Pro Gly Lys
1               5                   10                  15

Thr Val Thr Ile Ser Cys Ile Ser Asn Asp Val Pro Ala Ser Gly His
                20                  25                  30

Tyr His Arg Trp Tyr Gln Gln Arg Pro Gly Ser Ser Pro Thr Thr Val
            35                  40                  45

Ile Tyr Glu Asp Asp Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Asp Ser
                85                  90                  95

Thr Asn Pro Trp Val Phe Gly Gly Gly Thr Lys Leu Thr Val Leu
            100                 105                 110

<210> SEQ ID NO 10
<211> LENGTH: 13
<212> TYPE: PRT
<213> ORGANISM: Homo sapiens

<400> SEQUENCE: 10

Ile Ser Asn Asp Val Pro Ala Ser Gly His Tyr His Arg
1               5                   10

<210> SEQ ID NO 11
<211> LENGTH: 111
<212> TYPE: PRT
<213> ORGANISM: Homo sapiens

<400> SEQUENCE: 11

Asn Phe Met Leu Thr Gln Pro His Ser Val Ser Glu Ser Pro Gly Lys
1               5                   10                  15

Thr Val Thr Ile Ser Cys Val Leu Ser Pro Arg Thr His Ala Gly His
                20                  25                  30

Tyr Tyr Arg Trp Tyr Gln Gln Arg Pro Gly Ser Ser Pro Thr Thr Val
            35                  40                  45

Ile Tyr Glu Asp Asp Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
```

```
65              70              75              80

Leu Lys Thr Glu Asp Glu Ala Asp Tyr Tyr Cys Gln Ser Phe Asp Ser
                85              90              95

Thr Asn Pro Trp Val Phe Gly Gly Gly Thr Lys Leu Thr Val Leu
            100             105             110

<210> SEQ ID NO 12
<211> LENGTH: 13
<212> TYPE: PRT
<213> ORGANISM: Homo sapiens

<400> SEQUENCE: 12

Val Leu Ser Pro Arg Thr His Ala Gly His Tyr Tyr Arg
1               5               10

<210> SEQ ID NO 13
<211> LENGTH: 111
<212> TYPE: PRT
<213> ORGANISM: Homo sapiens

<400> SEQUENCE: 13

Asn Phe Met Leu Thr Gln Pro His Ser Val Ser Glu Ser Pro Gly Lys
1               5               10              15

Thr Val Thr Ile Ser Cys Met Arg Thr Gly Thr Gly Asn Lys Gly His
                20              25              30

Tyr Thr Arg Trp Tyr Gln Gln Arg Pro Gly Ser Ser Pro Thr Thr Val
            35              40              45

Ile Tyr Glu Asp Asp Gln Arg Pro Ser Gly Val Pro Asp Arg Phe Ser
        50              55              60

Gly Ser Ile Asp Ser Ser Ser Asn Ser Ala Ser Leu Thr Ile Ser Gly
65              70              75              80

Leu Lys Thr Glu Asp Glu Ala Asp Tyr Tyr Cys Gln Ser Phe Asp Ser
                85              90              95

Thr Asn Pro Trp Val Phe Gly Gly Gly Thr Lys Leu Thr Val Leu
            100             105             110

<210> SEQ ID NO 14
<211> LENGTH: 13
<212> TYPE: PRT
<213> ORGANISM: Homo sapiens

<400> SEQUENCE: 14

Met Arg Thr Gly Thr Gly Asn Lys Gly His Tyr Thr Arg
1               5               10

<210> SEQ ID NO 15
<211> LENGTH: 111
<212> TYPE: PRT
<213> ORGANISM: Homo sapiens

<400> SEQUENCE: 15

Asn Phe Met Leu Thr Gln Pro His Ser Val Ser Glu Ser Pro Gly Lys
1               5               10              15

Thr Val Thr Ile Ser Cys Arg Glu Thr Glu Leu Ser Arg Arg Leu His
                20              25              30

Tyr Val Arg Trp Tyr Gln Gln Arg Pro Gly Ser Ser Pro Thr Thr Val
            35              40              45

Ile Tyr Glu Asp Asp Gln Arg Pro Ser Gly Val Pro Asp Arg Phe Ser
        50              55              60
```

-continued

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Asp Ser
                85                  90                  95

Thr Asn Pro Trp Val Phe Gly Gly Gly Thr Lys Leu Thr Val Leu
            100                 105                 110

<210> SEQ ID NO 16
<211> LENGTH: 13
<212> TYPE: PRT
<213> ORGANISM: Homo sapiens

<400> SEQUENCE: 16

Arg Glu Thr Glu Leu Ser Arg Arg Leu His Tyr Val Arg
1               5                   10

<210> SEQ ID NO 17
<211> LENGTH: 111
<212> TYPE: PRT
<213> ORGANISM: Homo sapiens

<400> SEQUENCE: 17

Asn Phe Met Leu Thr Gln Pro His Ser Val Ser Glu Ser Pro Gly Lys
1               5                   10                  15

Thr Val Thr Ile Ser Cys Arg Gly Thr Gly Ser Ser Phe His His Lys
                20                  25                  30

Tyr Val Arg Trp Tyr Gln Gln Arg Pro Gly Ser Ser Pro Thr Thr Val
            35                  40                  45

Ile Tyr Glu Asp Asp Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Asp Ser
                85                  90                  95

Thr Asn Pro Trp Val Phe Gly Gly Gly Thr Lys Leu Thr Val Leu
            100                 105                 110

<210> SEQ ID NO 18
<211> LENGTH: 13
<212> TYPE: PRT
<213> ORGANISM: Homo sapiens

<400> SEQUENCE: 18

Arg Gly Thr Gly Ser Ser Phe His His Lys Tyr Val Arg
1               5                   10

<210> SEQ ID NO 19
<211> LENGTH: 290
<212> TYPE: PRT
<213> ORGANISM: Homo sapiens

<400> SEQUENCE: 19

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

-continued

```
Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 20
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (95)..(95)
<223> OTHER INFORMATION: X is any amino acid

<400> SEQUENCE: 20

Asn Phe Xaa Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
            35                  40                  45

Ile Tyr Glu Asp Asp Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95
```

-continued

```
Thr Asn Pro Trp Val Phe Gly Gly Gly Thr Lys Leu Thr Val Leu
            100                 105                 110

<210> SEQ ID NO 21
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Met or Leu
<220> FEATURE:
<221> NAME/KEY: MISC_FEATURE
<222> LOCATION: (95)..(95)
<223> OTHER INFORMATION: X is Asp, Gln, Glu or Ala

<400> SEQUENCE: 21

Asn Phe Xaa Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 22
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Leu
<220> FEATURE:
<221> NAME/KEY: MISC_FEATURE
<222> LOCATION: (95)..(95)
<223> OTHER INFORMATION: X is Gln, Glu or Ala

<400> SEQUENCE: 22

Asn Phe Xaa Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110
```

```
<210> SEQ ID NO 23
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is any amino acid

<400> SEQUENCE: 23

Gln Ser Phe Xaa Ser Thr Asn Pro Trp Val
1               5                   10

<210> SEQ ID NO 24
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is Asp, Gln, Glu or Ala

<400> SEQUENCE: 24

Gln Ser Phe Xaa Ser Thr Asn Pro Trp Val
1               5                   10

<210> SEQ ID NO 25
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is Gln, Glu or Ala

<400> SEQUENCE: 25

Gln Ser Phe Xaa Ser Thr Asn Pro Trp Val
1               5                   10

<210> SEQ ID NO 26
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: X is any amino acid
<220> FEATURE:
<221> NAME/KEY: MISC_FEATURE
<222> LOCATION: (62)..(62)
<223> OTHER INFORMATION: X is any amino acid
<220> FEATURE:
<221> NAME/KEY: MISC_FEATURE
<222> LOCATION: (110)..(110)
<223> OTHER INFORMATION: X is any amino acid

<400> SEQUENCE: 26

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Val Ile Ser Tyr Xaa Gly Ser Asn Lys Tyr Tyr Ala Xaa Ser Val
    50                  55                  60

Lys Gly Arg Phe Thr Ile Ser Arg Asp Asn Ser Lys Asn Thr Leu Asn
65                  70                  75                  80
```

-continued

```
Leu Gln Met Asn Ser Leu Arg Ala Glu Asp Thr Ala Val Tyr Tyr Cys
                85                  90                  95

Ala Lys Gly Ala Leu Thr His Trp Gly Val Val Ile Gly Xaa Gly Met
            100                 105                 110

Asp Val Trp Gly Gln Gly Thr Thr Val Thr Val Ser Ser
        115                 120                 125

<210> SEQ ID NO 27
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: X is Asp, Gln, Glu or Ala
<220> FEATURE:
<221> NAME/KEY: MISC_FEATURE
<222> LOCATION: (62)..(62)
<223> OTHER INFORMATION: X is Asp, Gln, Glu or Ala
<220> FEATURE:
<221> NAME/KEY: MISC_FEATURE
<222> LOCATION: (110)..(110)
<223> OTHER INFORMATION: X is Asp, Gln, Glu or Ala

<400> SEQUENCE: 27

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Val Ile Ser Tyr Xaa Gly Ser Asn Lys Tyr Tyr Ala Xaa Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Lys Gly Ala Leu Thr His Trp Gly Val Val Ile Gly Xaa Gly Met
            100                 105                 110

Asp Val Trp Gly Gln Gly Thr Thr Val Thr Val Ser Ser
        115                 120                 125

<210> SEQ ID NO 28
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: X is Gln, Glu or Ala
<220> FEATURE:
<221> NAME/KEY: MISC_FEATURE
<222> LOCATION: (62)..(62)
<223> OTHER INFORMATION: X is Gln, Glu or Ala
<220> FEATURE:
<221> NAME/KEY: MISC_FEATURE
<222> LOCATION: (110)..(110)
<223> OTHER INFORMATION: X is Gln, Glu or Ala

<400> SEQUENCE: 28

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

-continued

```
Gly Met Tyr Trp Val Arg Gln Ala Pro Gly Lys Gly Leu Glu Trp Val
        35                  40                  45

Ala Val Ile Ser Tyr Xaa Gly Ser Asn Lys Tyr Tyr Ala Xaa Ser Val
    50                  55                  60

Lys Gly Arg Phe Thr Ile Ser Arg Asp Asn Ser Lys Asn Thr Leu Asn
65                      70                  75                  80

Leu Gln Met Asn Ser Leu Arg Ala Glu Asp Thr Ala Val Tyr Tyr Cys
                85                  90                  95

Ala Lys Gly Ala Leu Thr His Trp Gly Val Val Ile Gly Xaa Gly Met
                100                 105                 110

Asp Val Trp Gly Gln Gly Thr Thr Val Thr Val Ser Ser
        115                 120                 125
```

```
<210> SEQ ID NO 29
<211> LENGTH: 17
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is any amino acid
<220> FEATURE:
<221> NAME/KEY: MISC_FEATURE
<222> LOCATION: (13)..(13)
<223> OTHER INFORMATION: X is any amino acid

<400> SEQUENCE: 29

Val Ile Ser Tyr Xaa Gly Ser Asn Lys Tyr Tyr Ala Xaa Ser Val Lys
1               5                   10                  15

Gly
```

```
<210> SEQ ID NO 30
<211> LENGTH: 17
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is  Asp, Gln, Glu or Ala
<220> FEATURE:
<221> NAME/KEY: MISC_FEATURE
<222> LOCATION: (13)..(13)
<223> OTHER INFORMATION: X is  Asp, Gln, Glu or Ala

<400> SEQUENCE: 30

Val Ile Ser Tyr Xaa Gly Ser Asn Lys Tyr Tyr Ala Xaa Ser Val Lys
1               5                   10                  15

Gly
```

```
<210> SEQ ID NO 31
<211> LENGTH: 17
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is Gln, Glu or Ala
<220> FEATURE:
<221> NAME/KEY: MISC_FEATURE
<222> LOCATION: (13)..(13)
<223> OTHER INFORMATION: X is Gln, Glu or Ala

<400> SEQUENCE: 31

Val Ile Ser Tyr Xaa Gly Ser Asn Lys Tyr Tyr Ala Xaa Ser Val Lys
1               5                   10                  15
```

-continued

Gly

```
<210> SEQ ID NO 32
<211> LENGTH: 16
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: X is any amino acid

<400> SEQUENCE: 32

Gly Ala Leu Thr His Trp Gly Val Val Ile Gly Xaa Gly Met Asp Val
1               5                   10                  15

<210> SEQ ID NO 33
<211> LENGTH: 16
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: X is Asp, Gln, Glu or Ala

<400> SEQUENCE: 33

Gly Ala Leu Thr His Trp Gly Val Val Ile Gly Xaa Gly Met Asp Val
1               5                   10                  15

<210> SEQ ID NO 34
<211> LENGTH: 16
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: X is Gln, Glu or Ala

<400> SEQUENCE: 34

Gly Ala Leu Thr His Trp Gly Val Val Ile Gly Xaa Gly Met Asp Val
1               5                   10                  15

<210> SEQ ID NO 35
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (95)..(95)
<223> OTHER INFORMATION: X is any amino acid

<400> SEQUENCE: 35

Asn Phe Xaa Leu Thr Gln Pro His Ser Val Ser Glu Ser Pro Gly Lys
1               5                   10                  15

Thr Val Thr Ile Ser Cys Ile Ser Asn Asp Val Pro Ala Ser Gly His
            20                  25                  30

Tyr His Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
```

-continued

```
                    85                  90                  95

Thr Asn Pro Trp Val Phe Gly Gly Gly Thr Lys Leu Thr Val Leu
            100                 105                 110

<210> SEQ ID NO 36
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Met or Leu
<220> FEATURE:
<221> NAME/KEY: MISC_FEATURE
<222> LOCATION: (95)..(95)
<223> OTHER INFORMATION: X is Asp, Gln, Glu or Ala

<400> SEQUENCE: 36

Asn Phe Xaa Leu Thr Gln Pro His Ser Val Ser Glu Ser Pro Gly Lys
1               5                   10                  15

Thr Val Thr Ile Ser Cys Ile Ser Asn Asp Val Pro Ala Ser Gly His
            20                  25                  30

Tyr His Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 37
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Leu
<220> FEATURE:
<221> NAME/KEY: MISC_FEATURE
<222> LOCATION: (95)..(95)
<223> OTHER INFORMATION: X is Gln, Glu or Ala

<400> SEQUENCE: 37

Asn Phe Xaa Leu Thr Gln Pro His Ser Val Ser Glu Ser Pro Gly Lys
1               5                   10                  15

Thr Val Thr Ile Ser Cys Ile Ser Asn Asp Val Pro Ala Ser Gly His
            20                  25                  30

Tyr His Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110
```

```
<210> SEQ ID NO 38
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (95)..(95)
<223> OTHER INFORMATION: X is any amino acid

<400> SEQUENCE: 38

Asn Phe Xaa Leu Thr Gln Pro His Ser Val Ser Glu Ser Pro Gly Lys
1               5                   10                  15

Thr Val Thr Ile Ser Cys Val Leu Ser Pro Arg Thr His Ala Gly His
            20                  25                  30

Tyr Tyr Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 39
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Met or Leu
<220> FEATURE:
<221> NAME/KEY: MISC_FEATURE
<222> LOCATION: (95)..(95)
<223> OTHER INFORMATION: X is Asp, Gln, Glu or Ala

<400> SEQUENCE: 39

Asn Phe Xaa Leu Thr Gln Pro His Ser Val Ser Glu Ser Pro Gly Lys
1               5                   10                  15

Thr Val Thr Ile Ser Cys Val Leu Ser Pro Arg Thr His Ala Gly His
            20                  25                  30

Tyr Tyr Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 40
<211> LENGTH: 111
<212> TYPE: PRT
<213> ORGANISM: Homo sapiens
```

```
<220> FEATURE:
<221> NAME/KEY: MISC_FEATURE
<222> LOCATION: (3)..(3)
<223> OTHER INFORMATION: X is Leu
<220> FEATURE:
<221> NAME/KEY: MISC_FEATURE
<222> LOCATION: (95)..(95)
<223> OTHER INFORMATION: X is Gln, Glu or Ala

<400> SEQUENCE: 40

Asn Phe Xaa Leu Thr Gln Pro His Ser Val Ser Glu Ser Pro Gly Lys
1               5                   10                  15

Thr Val Thr Ile Ser Cys Val Leu Ser Pro Arg Thr His Ala Gly His
            20                  25                  30

Tyr Tyr Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 41
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (23)..(23)
<223> OTHER INFORMATION: X is any amino acid
<220> FEATURE:
<221> NAME/KEY: MISC_FEATURE
<222> LOCATION: (95)..(95)
<223> OTHER INFORMATION: X is any amino acid

<400> SEQUENCE: 41

Asn Phe Xaa Leu Thr Gln Pro His Ser Val Ser Glu Ser Pro Gly Lys
1               5                   10                  15

Thr Val Thr Ile Ser Cys Xaa Arg Thr Gly Thr Gly Asn Lys Gly His
            20                  25                  30

Tyr Thr Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 42
<211> LENGTH: 111
<212> TYPE: PRT
<213> ORGANISM: Homo sapiens
<220> FEATURE:
```

<221> NAME/KEY: MISC_FEATURE
<222> LOCATION: (3)..(3)
<223> OTHER INFORMATION: X is Met or Leu
<220> FEATURE:
<221> NAME/KEY: MISC_FEATURE
<222> LOCATION: (23)..(23)
<223> OTHER INFORMATION: X is Met, Ala or Leu
<220> FEATURE:
<221> NAME/KEY: MISC_FEATURE
<222> LOCATION: (95)..(95)
<223> OTHER INFORMATION: X is Asp, Gln, Glu or Ala

<400> SEQUENCE: 42

Asn Phe Xaa Leu Thr Gln Pro His Ser Val Ser Glu Ser Pro Gly Lys
1               5                   10                  15

Thr Val Thr Ile Ser Cys Xaa Arg Thr Gly Thr Gly Asn Lys Gly His
            20                  25                  30

Tyr Thr Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 43
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Leu
<220> FEATURE:
<221> NAME/KEY: MISC_FEATURE
<222> LOCATION: (23)..(23)
<223> OTHER INFORMATION: X is Ala or Leu
<220> FEATURE:
<221> NAME/KEY: MISC_FEATURE
<222> LOCATION: (95)..(95)
<223> OTHER INFORMATION: X is Gln, Glu or Ala

<400> SEQUENCE: 43

Asn Phe Xaa Leu Thr Gln Pro His Ser Val Ser Glu Ser Pro Gly Lys
1               5                   10                  15

Thr Val Thr Ile Ser Cys Xaa Arg Thr Gly Thr Gly Asn Lys Gly His
            20                  25                  30

Tyr Thr Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 44
<211> LENGTH: 13

```
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any amino acid

<400> SEQUENCE: 44

Xaa Arg Thr Gly Thr Gly Asn Lys Gly His Tyr Thr Arg
1               5                   10

<210> SEQ ID NO 45
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is Met, Ala or Leu

<400> SEQUENCE: 45

Xaa Arg Thr Gly Thr Gly Asn Lys Gly His Tyr Thr Arg
1               5                   10

<210> SEQ ID NO 46
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is Ala or Leu

<400> SEQUENCE: 46

Xaa Arg Thr Gly Thr Gly Asn Lys Gly His Tyr Thr Arg
1               5                   10

<210> SEQ ID NO 47
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (95)..(95)
<223> OTHER INFORMATION: X is any amino acid

<400> SEQUENCE: 47

Asn Phe Xaa Leu Thr Gln Pro His Ser Val Ser Glu Ser Pro Gly Lys
1               5                   10                  15

Thr Val Thr Ile Ser Cys Arg Glu Thr Glu Leu Ser Arg Arg Leu His
                20                  25                  30

Tyr Val Arg Trp Tyr Gln Gln Arg Pro Gly Ser Ser Pro Thr Thr Val
            35                  40                  45

Ile Tyr Glu Asp Asp Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
                100                 105                 110
```

<210> SEQ ID NO 48
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Met or Leu
<220> FEATURE:
<221> NAME/KEY: MISC_FEATURE
<222> LOCATION: (95)..(95)
<223> OTHER INFORMATION: X is Asp, Gln, Glu or Ala

<400> SEQUENCE: 48

Asn Phe Xaa Leu Thr Gln Pro His Ser Val Ser Glu Ser Pro Gly Lys
1               5                   10                  15

Thr Val Thr Ile Ser Cys Arg Glu Thr Glu Leu Ser Arg Arg Leu His
            20                  25                  30

Tyr Val Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 49
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Leu
<220> FEATURE:
<221> NAME/KEY: MISC_FEATURE
<222> LOCATION: (95)..(95)
<223> OTHER INFORMATION: X is Gln, Glu or Ala

<400> SEQUENCE: 49

Asn Phe Xaa Leu Thr Gln Pro His Ser Val Ser Glu Ser Pro Gly Lys
1               5                   10                  15

Thr Val Thr Ile Ser Cys Arg Glu Thr Glu Leu Ser Arg Arg Leu His
            20                  25                  30

Tyr Val Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 50
<211> LENGTH: 111
<212> TYPE: PRT
<213> ORGANISM: Homo sapiens

```
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (95)..(95)
<223> OTHER INFORMATION: X is any amino acid

<400> SEQUENCE: 50

Asn Phe Xaa Leu Thr Gln Pro His Ser Val Ser Glu Ser Pro Gly Lys
1               5                   10                  15

Thr Val Thr Ile Ser Cys Arg Gly Thr Gly Ser Ser Phe His His Lys
            20                  25                  30

Tyr Val Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 51
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Met or Leu
<220> FEATURE:
<221> NAME/KEY: MISC_FEATURE
<222> LOCATION: (95)..(95)
<223> OTHER INFORMATION: X is Asp, Gln, Glu or Ala

<400> SEQUENCE: 51

Asn Phe Xaa Leu Thr Gln Pro His Ser Val Ser Glu Ser Pro Gly Lys
1               5                   10                  15

Thr Val Thr Ile Ser Cys Arg Gly Thr Gly Ser Ser Phe His His Lys
            20                  25                  30

Tyr Val Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 52
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Leu
<220> FEATURE:
```

```
<221> NAME/KEY: MISC_FEATURE
<222> LOCATION: (95)..(95)
<223> OTHER INFORMATION: X is Gln, Glu or Ala

<400> SEQUENCE: 52

Asn Phe Xaa Leu Thr Gln Pro His Ser Val Ser Glu Ser Pro Gly Lys
1               5                   10                  15

Thr Val Thr Ile Ser Cys Arg Gly Thr Gly Ser Ser Phe His His Lys
            20                  25                  30

Tyr Val Arg Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 53
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: X is any amino acid
<220> FEATURE:
<221> NAME/KEY: MISC_FEATURE
<222> LOCATION: (62)..(62)
<223> OTHER INFORMATION: X is any amino acid
<220> FEATURE:
<221> NAME/KEY: MISC_FEATURE
<222> LOCATION: (110)..(110)
<223> OTHER INFORMATION: X is any amino acid

<400> SEQUENCE: 53

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Val Ile Ser Tyr Xaa Gly Ser Asn Lys Tyr Tyr Ala Xaa Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Lys Gly Ala Leu Thr His Trp Gly Val Val Ile Gly Xaa Gly Met
            100                 105                 110

Asp Val Trp Gly Gln Gly Thr Thr Val Thr Val Ser Ser
            115                 120                 125

<210> SEQ ID NO 54
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
```

<223> OTHER INFORMATION: X is Thr, Ile, Val, Met, Arg, Ser, Leu, Glu,
      Gly, Asn, Asp, Phe, Ala, His, Phe, Lys, Tyr or Gln
<220> FEATURE:
<221> NAME/KEY: MISC_FEATURE
<222> LOCATION: (62)..(62)
<223> OTHER INFORMATION: X is Thr, Ile, Val, Met, Arg, Ser, Leu, Glu,
      Gly, Asn, Asp, Phe, Ala, His, Phe, Lys, Tyr or Gln
<220> FEATURE:
<221> NAME/KEY: MISC_FEATURE
<222> LOCATION: (110)..(110)
<223> OTHER INFORMATION: X is Thr, Ile, Val, Met, Arg, Ser, Leu, Glu,
      Gly, Asn, Asp, Phe, Ala, His, Phe, Lys, Tyr or Gln

<400> SEQUENCE: 54

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Val Ile Ser Tyr Xaa Gly Ser Asn Lys Tyr Tyr Ala Xaa Ser Val
        50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Lys Gly Ala Leu Thr His Trp Gly Val Val Ile Gly Xaa Gly Met
            100                 105                 110

Asp Val Trp Gly Gln Gly Thr Thr Val Thr Val Ser Ser
            115                 120                 125

<210> SEQ ID NO 55
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: X is Asp, Gln, Glu, Ala or a conservative amino
      acid substitution thereof
<220> FEATURE:
<221> NAME/KEY: MISC_FEATURE
<222> LOCATION: (62)..(62)
<223> OTHER INFORMATION: X is Asp, Gln, Glu, Ala or a conservative amino
      acid substitution thereof
<220> FEATURE:
<221> NAME/KEY: MISC_FEATURE
<222> LOCATION: (110)..(110)
<223> OTHER INFORMATION: X is Asp, Gln, Glu, Ala or a conservative amino
      acid substitution thereof

<400> SEQUENCE: 55

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Val Ile Ser Tyr Xaa Gly Ser Asn Lys Tyr Tyr Ala Xaa Ser Val
        50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

-continued

```
Ala Lys Gly Ala Leu Thr His Trp Gly Val Val Ile Gly Xaa Gly Met
            100                 105                 110

Asp Val Trp Gly Gln Gly Thr Thr Val Thr Val Ser Ser
            115                 120                 125

<210> SEQ ID NO 56
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: X is Asp, Gln, Glu and Ala
<220> FEATURE:
<221> NAME/KEY: MISC_FEATURE
<222> LOCATION: (62)..(62)
<223> OTHER INFORMATION: X is Asp, Gln, Glu and Ala
<220> FEATURE:
<221> NAME/KEY: MISC_FEATURE
<222> LOCATION: (110)..(110)
<223> OTHER INFORMATION: X is Asp, Gln, Glu and Ala

<400> SEQUENCE: 56

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Val Ile Ser Tyr Xaa Gly Ser Asn Lys Tyr Tyr Ala Xaa Ser Val
            50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                    85                  90                  95

Ala Lys Gly Ala Leu Thr His Trp Gly Val Val Ile Gly Xaa Gly Met
            100                 105                 110

Asp Val Trp Gly Gln Gly Thr Thr Val Thr Val Ser Ser
            115                 120                 125

<210> SEQ ID NO 57
<211> LENGTH: 125
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: X is Gln, Glu or Ala
<220> FEATURE:
<221> NAME/KEY: MISC_FEATURE
<222> LOCATION: (62)..(62)
<223> OTHER INFORMATION: X is Gln, Glu or Ala
<220> FEATURE:
<221> NAME/KEY: MISC_FEATURE
<222> LOCATION: (110)..(110)
<223> OTHER INFORMATION: X is Gln, Glu or Ala

<400> SEQUENCE: 57

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45
```

-continued

```
Ala Val Ile Ser Tyr Xaa Gly Ser Asn Lys Tyr Tyr Ala Xaa Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Lys Gly Ala Leu Thr His Trp Gly Val Val Ile Gly Xaa Gly Met
            100                 105                 110

Asp Val Trp Gly Gln Gly Thr Thr Val Thr Val Ser Ser
            115                 120                 125
```

```
<210> SEQ ID NO 58
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (23)..(23)
<223> OTHER INFORMATION: X is any amino acid
<220> FEATURE:
<221> NAME/KEY: MISC_FEATURE
<222> LOCATION: (24)..(24)
<223> OTHER INFORMATION: X is any amino acid
<220> FEATURE:
<221> NAME/KEY: MISC_FEATURE
<222> LOCATION: (25)..(25)
<223> OTHER INFORMATION: X is any amino acid
<220> FEATURE:
<221> NAME/KEY: MISC_FEATURE
<222> LOCATION: (26)..(26)
<223> OTHER INFORMATION: X is any amino acid
<220> FEATURE:
<221> NAME/KEY: MISC_FEATURE
<222> LOCATION: (27)..(27)
<223> OTHER INFORMATION: X is any amino acid
<220> FEATURE:
<221> NAME/KEY: MISC_FEATURE
<222> LOCATION: (28)..(28)
<223> OTHER INFORMATION: X is any amino acid
<220> FEATURE:
<221> NAME/KEY: MISC_FEATURE
<222> LOCATION: (29)..(29)
<223> OTHER INFORMATION: X is any amino acid
<220> FEATURE:
<221> NAME/KEY: MISC_FEATURE
<222> LOCATION: (30)..(30)
<223> OTHER INFORMATION: X is any amino acid
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: MISC_FEATURE
<222> LOCATION: (32)..(32)
<223> OTHER INFORMATION: X is any amino acid
<220> FEATURE:
<221> NAME/KEY: MISC_FEATURE
<222> LOCATION: (34)..(34)
<223> OTHER INFORMATION: X is any amino acid
<220> FEATURE:
<221> NAME/KEY: MISC_FEATURE
<222> LOCATION: (35)..(35)
<223> OTHER INFORMATION: X is any amino acid
<220> FEATURE:
<221> NAME/KEY: MISC_FEATURE
<222> LOCATION: (95)..(95)
<223> OTHER INFORMATION: X is any amino acid

<400> SEQUENCE: 58
```

-continued

Asn Phe Xaa Leu Thr Gln Pro His Ser Val Ser Glu Ser Pro Gly Lys
1               5                   10                  15

Thr Val Thr Ile Ser Cys Xaa Xaa Xaa Xaa Xaa Xaa Xaa Xaa Xaa
                20                  25                  30

Tyr Xaa Xaa Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
                100                 105                 110

<210> SEQ ID NO 59
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (23)..(23)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (24)..(24)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (25)..(25)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (26)..(26)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (27)..(27)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (28)..(28)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (29)..(29)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (30)..(30)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (31)..(31)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE

```
<222> LOCATION: (32)..(32)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (34)..(34)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (35)..(35)
<223> OTHER INFORMATION: X is Thr, Ile, Val, Met, Arg, Ser, Leu, Glu,
      Gly, Asn, Asp, Pro, Ala, His, Phe, Lys, Tyr or Gln
<220> FEATURE:
<221> NAME/KEY: MISC_FEATURE
<222> LOCATION: (95)..(95)
<223> OTHER INFORMATION: X is Thr, Ile, Val, Met, Arg, Ser, Leu, Glu,
      Gly, Asn, Asp, Pro, Ala, His, Phe, Lys, Tyr or Gln

<400> SEQUENCE: 59

Asn Phe Xaa Leu Thr Gln Pro His Ser Val Ser Glu Ser Pro Gly Lys
1               5                   10                  15

Thr Val Thr Ile Ser Cys Xaa Xaa Xaa Xaa Xaa Xaa Xaa Xaa Xaa
            20                  25                  30

Tyr Xaa Xaa Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 60
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Met, Leu or a conservative amino acid
      substitution thereof
<220> FEATURE:
<221> NAME/KEY: MISC_FEATURE
<222> LOCATION: (23)..(23)
<223> OTHER INFORMATION: X is Ala, Leu, Thr, Ile, Val, Met, Arg or a
      conservative amino acid substitution thereof
<220> FEATURE:
<221> NAME/KEY: MISC_FEATURE
<222> LOCATION: (24)..(24)
<223> OTHER INFORMATION: X is Arg, Ser, Leu, Glu, Gly or a conservative
      amino acid substitution thereof
<220> FEATURE:
<221> NAME/KEY: MISC_FEATURE
<222> LOCATION: (25)..(25)
<223> OTHER INFORMATION: X is Ser, Asn, Thr or a conservative amino acid
      substitution thereof
<220> FEATURE:
<221> NAME/KEY: MISC_FEATURE
<222> LOCATION: (26)..(26)
<223> OTHER INFORMATION: X is Ser, Asp, Pro, Gly, Glu or a conservative
      amino acid substitution thereof
<220> FEATURE:
<221> NAME/KEY: MISC_FEATURE
<222> LOCATION: (27)..(27)
<223> OTHER INFORMATION: X is Gly, Val, Arg, Thr, Leu, Ser or a
      conservative amino acid substitution thereof
<220> FEATURE:
<221> NAME/KEY: MISC_FEATURE
```

```
<222> LOCATION: (28)..(28)
<223> OTHER INFORMATION: X is Ser, Pro, Thr, Gly or a conservative amino
      acid substitution thereof
<220> FEATURE:
<221> NAME/KEY: MISC_FEATURE
<222> LOCATION: (29)..(29)
<223> OTHER INFORMATION: X is Ile, Ala, His, Asn, Arg, Phe or a
      conservative amino acid substitution thereof
<220> FEATURE:
<221> NAME/KEY: MISC_FEATURE
<222> LOCATION: (30)..(30)
<223> OTHER INFORMATION: X is Ala, Ser, Lys, Arg, His or a conservative
      amino acid substitution thereof
<220> FEATURE:
<221> NAME/KEY: MISC_FEATURE
<222> LOCATION: (31)..(31)
<223> OTHER INFORMATION: X is Ser, Gly, Leu, His or a conservative amino
      acid substitution thereof
<220> FEATURE:
<221> NAME/KEY: MISC_FEATURE
<222> LOCATION: (32)..(32)
<223> OTHER INFORMATION: X is Asn, His, Lys or a conservative amino acid
      substitution thereof
<220> FEATURE:
<221> NAME/KEY: MISC_FEATURE
<222> LOCATION: (34)..(34)
<223> OTHER INFORMATION: X is Val, His, Tyr, Thr or a conservative amino
      acid substitution thereof
<220> FEATURE:
<221> NAME/KEY: MISC_FEATURE
<222> LOCATION: (35)..(35)
<223> OTHER INFORMATION: X is Gln, Arg or a conservative amino acid
      substitution thereof
<220> FEATURE:
<221> NAME/KEY: MISC_FEATURE
<222> LOCATION: (95)..(95)
<223> OTHER INFORMATION: X is Asp, Gln, Glu, Ala or a conservative amino
      acid substitution thereof

<400> SEQUENCE: 60

Asn Phe Xaa Leu Thr Gln Pro His Ser Val Ser Glu Ser Pro Gly Lys
1               5                   10                  15

Thr Val Thr Ile Ser Cys Xaa Xaa Xaa Xaa Xaa Xaa Xaa Xaa Xaa Xaa
            20                  25                  30

Tyr Xaa Xaa Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 61
<211> LENGTH: 111
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Met or Leu
<220> FEATURE:
<221> NAME/KEY: MISC_FEATURE
<222> LOCATION: (23)..(23)
<223> OTHER INFORMATION: X is Ala, Leu, Thr, Ile, Val, Met or Arg
<220> FEATURE:
<221> NAME/KEY: MISC_FEATURE
<222> LOCATION: (24)..(24)
<223> OTHER INFORMATION: X is Arg, Ser, Leu, Glu or Gly
```

-continued

```
<220> FEATURE:
<221> NAME/KEY: MISC_FEATURE
<222> LOCATION: (25)..(25)
<223> OTHER INFORMATION: X is Ser, Asn or Thr
<220> FEATURE:
<221> NAME/KEY: MISC_FEATURE
<222> LOCATION: (26)..(26)
<223> OTHER INFORMATION: X is Ser, Asp, Pro, Gly or Glu
<220> FEATURE:
<221> NAME/KEY: MISC_FEATURE
<222> LOCATION: (27)..(27)
<223> OTHER INFORMATION: X is Gly, Val, Arg, Thr, Leu or Ser
<220> FEATURE:
<221> NAME/KEY: MISC_FEATURE
<222> LOCATION: (28)..(28)
<223> OTHER INFORMATION: X is Ser, Pro, Thr or Gly
<220> FEATURE:
<221> NAME/KEY: MISC_FEATURE
<222> LOCATION: (29)..(29)
<223> OTHER INFORMATION: X is Ile, Ala, His, Asn, Arg or Phe
<220> FEATURE:
<221> NAME/KEY: MISC_FEATURE
<222> LOCATION: (30)..(30)
<223> OTHER INFORMATION: X is Ala, Ser, Lys, Arg or His
<220> FEATURE:
<221> NAME/KEY: MISC_FEATURE
<222> LOCATION: (31)..(31)
<223> OTHER INFORMATION: X is Ser, Gly, Leu or His
<220> FEATURE:
<221> NAME/KEY: MISC_FEATURE
<222> LOCATION: (32)..(32)
<223> OTHER INFORMATION: X is Asn, His or Lys
<220> FEATURE:
<221> NAME/KEY: MISC_FEATURE
<222> LOCATION: (34)..(34)
<223> OTHER INFORMATION: X is Val, His, Tyr or Thr
<220> FEATURE:
<221> NAME/KEY: MISC_FEATURE
<222> LOCATION: (35)..(35)
<223> OTHER INFORMATION: X is Gln or Arg
<220> FEATURE:
<221> NAME/KEY: MISC_FEATURE
<222> LOCATION: (95)..(95)
<223> OTHER INFORMATION: X is Asp, Gln, Glu or Ala

<400> SEQUENCE: 61

Asn Phe Xaa Leu Thr Gln Pro His Ser Val Ser Glu Ser Pro Gly Lys
1               5                   10                  15

Thr Val Thr Ile Ser Cys Xaa Xaa Xaa Xaa Xaa Xaa Xaa Xaa Xaa Xaa
            20                  25                  30

Tyr Xaa Xaa Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
            100                 105                 110

<210> SEQ ID NO 62
<211> LENGTH: 111
<212> TYPE: PRT
<213> ORGANISM: Homo sapiens
<220> FEATURE:
<221> NAME/KEY: MISC_FEATURE
```

```
<222> LOCATION: (3)..(3)
<223> OTHER INFORMATION: X is Leu
<220> FEATURE:
<221> NAME/KEY: MISC_FEATURE
<222> LOCATION: (23)..(23)
<223> OTHER INFORMATION: X is Leu, Thr, Ile, Val, Met and Arg
<220> FEATURE:
<221> NAME/KEY: MISC_FEATURE
<222> LOCATION: (24)..(24)
<223> OTHER INFORMATION: X is Ser, Leu, Glu and Gly
<220> FEATURE:
<221> NAME/KEY: MISC_FEATURE
<222> LOCATION: (25)..(25)
<223> OTHER INFORMATION: X is Asn and Thr
<220> FEATURE:
<221> NAME/KEY: MISC_FEATURE
<222> LOCATION: (26)..(26)
<223> OTHER INFORMATION: X is Asp, Pro, Gly and Glu
<220> FEATURE:
<221> NAME/KEY: MISC_FEATURE
<222> LOCATION: (27)..(27)
<223> OTHER INFORMATION: X is Val, Arg, Thr, Leu and Ser
<220> FEATURE:
<221> NAME/KEY: MISC_FEATURE
<222> LOCATION: (28)..(28)
<223> OTHER INFORMATION: X is Pro, Thr and Gly
<220> FEATURE:
<221> NAME/KEY: MISC_FEATURE
<222> LOCATION: (29)..(29)
<223> OTHER INFORMATION: X is Ala, His, Asn, Arg and Phe
<220> FEATURE:
<221> NAME/KEY: MISC_FEATURE
<222> LOCATION: (30)..(30)
<223> OTHER INFORMATION: X is Ser, Lys, Arg and His
<220> FEATURE:
<221> NAME/KEY: MISC_FEATURE
<222> LOCATION: (31)..(31)
<223> OTHER INFORMATION: X is Gly, Leu and His
<220> FEATURE:
<221> NAME/KEY: MISC_FEATURE
<222> LOCATION: (32)..(32)
<223> OTHER INFORMATION: X is His and Lys
<220> FEATURE:
<221> NAME/KEY: MISC_FEATURE
<222> LOCATION: (34)..(34)
<223> OTHER INFORMATION: X is His, Tyr and Thr
<220> FEATURE:
<221> NAME/KEY: MISC_FEATURE
<222> LOCATION: (35)..(35)
<223> OTHER INFORMATION: X is Arg
<220> FEATURE:
<221> NAME/KEY: MISC_FEATURE
<222> LOCATION: (95)..(95)
<223> OTHER INFORMATION: X is Gln, Glu and Ala

<400> SEQUENCE: 62

Asn Phe Xaa Leu Thr Gln Pro His Ser Val Ser Glu Ser Pro Gly Lys
1               5                   10                  15

Thr Val Thr Ile Ser Cys Xaa Xaa Xaa Xaa Xaa Xaa Xaa Xaa Xaa Xaa
            20                  25                  30

Tyr Xaa Xaa Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Xaa Ser
                85                  90                  95

Thr Asn Pro Trp Val Phe Gly Gly Gly Thr Lys Leu Thr Val Leu
                100                 105                 110
```